US011053484B2

(12) United States Patent
Jantz et al.

(10) Patent No.: US 11,053,484 B2
(45) Date of Patent: Jul. 6, 2021

(54) GENETICALLY-MODIFIED T CELLS COMPRISING A MODIFIED INTRON IN THE T CELL RECEPTOR ALPHA GENE

(71) Applicant: Precision BioSciences, Inc., Durham, NC (US)

(72) Inventors: Derek Jantz, Durham, NC (US); James Jefferson Smith, Morrisville, NC (US); Clayton Beard, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 16/627,052

(22) PCT Filed: Jun. 27, 2018

(86) PCT No.: PCT/US2018/039740
§ 371 (c)(1),
(2) Date: Dec. 27, 2019

(87) PCT Pub. No.: WO2019/005957
PCT Pub. Date: Jan. 3, 2019

(65) Prior Publication Data
US 2020/0123516 A1    Apr. 23, 2020

Related U.S. Application Data

(60) Provisional application No. 62/579,473, filed on Oct. 31, 2017, provisional application No. 62/527,845, filed on Jun. 30, 2017.

(51) Int. Cl.
*A61K 35/17* (2015.01)
*C12N 5/0783* (2010.01)
*C12N 9/22* (2006.01)
*C07K 14/725* (2006.01)
*C12N 15/86* (2006.01)
*C12N 15/90* (2006.01)

(52) U.S. Cl.
CPC ............... *C12N 9/22* (2013.01); *A61K 35/17* (2013.01); *C07K 14/7051* (2013.01); *C12N 5/0636* (2013.01); *C12N 15/86* (2013.01); *C12N 15/907* (2013.01); *C12N 2750/14143* (2013.01); *C12N 2800/60* (2013.01); *C12N 2800/80* (2013.01); *C12N 2840/20* (2013.01)

(58) Field of Classification Search
CPC .... C12N 15/1051; C12N 9/22; C12N 5/0636; C12N 2510/00; C12N 15/907; A61K 35/17
See application file for complete search history.

(56) References Cited

U.S. PATENT DOCUMENTS

| | | | |
|---|---|---|---|
| 4,873,192 A | 10/1989 | Kunkel | |
| 6,015,832 A | 1/2000 | Baker, Jr. et al. | |
| 6,506,803 B1 | 1/2003 | Baker, Jr. et al. | |
| 6,559,189 B2 | 5/2003 | Baker, Jr. et al. | |
| 6,635,676 B2 | 10/2003 | Baker, Jr. et al. | |
| 8,021,867 B2 | 9/2011 | Smith et al. | |
| 8,445,251 B2 | 5/2013 | Smith et al. | |
| 8,697,359 B1* | 4/2014 | Zhang | C12N 15/85 435/6.1 |
| 8,822,647 B2 | 9/2014 | Jensen et al. | |
| 8,956,828 B2 | 2/2015 | Bonini et al. | |
| 9,889,160 B2 | 2/2018 | Jantz et al. | |
| 9,889,161 B2 | 2/2018 | Jantz et al. | |
| 9,950,010 B1 | 4/2018 | Jantz et al. | |
| 9,950,011 B1 | 4/2018 | Jantz et al. | |
| 9,969,975 B1 | 5/2018 | Jantz et al. | |
| 9,993,501 B2 | 6/2018 | Jantz et al. | |
| 9,993,502 B1 | 6/2018 | Jantz et al. | |
| 10,093,899 B1 | 10/2018 | Jantz et al. | |

(Continued)

FOREIGN PATENT DOCUMENTS

| | | |
|---|---|---|
| EP | 3 004 337 A1 | 4/2016 |
| JP | 2009-511085 A | 3/2009 |

(Continued)

OTHER PUBLICATIONS

Taylor et al. Apoptosis: controlled demolition at the cellular level. Nature Reviews: Molecular Cell Biology, vol. 9, pp. 231-241, 2008, published online Dec. 12, 2007. (Year: 2007).*

Shao et al. Mechanisms for U2AF to define 3' splice sites and regulate alternative splicing in the human genome. Nature Structural & Molecular Biology, vol. 21, No. 11, pp. 997-1005, Nov. 2014, including p. 1/1 of Online Methods, and 1/11-11/11 of Supplementary Text and Figures. (Year: 2014).*

(Continued)

*Primary Examiner* — Jennifer Dunston
(74) *Attorney, Agent, or Firm* — Wolf, Greenfield & Sacks, P.C.

(57) ABSTRACT

The present invention provides a genetically-modified T cell comprising in its genome a modified human T cell receptor alpha gene. The modified T cell receptor alpha gene comprises an exogenous sequence of interest inserted into an intron within the T cell receptor alpha gene that is positioned 5' upstream of TRAC exon 1. The exogenous sequence of interest can comprise an exogenous splice acceptor site and/or a poly A signal, which disrupts expression of the T cell receptor alpha subunit. The sequence of interest can also include a coding sequence for a polypeptide, such as a chimeric antigen receptor. Additionally, the endogenous splice donor site and the endogenous splice acceptor site flanking the intron are unmodified and/or remain functional. The invention further provides compositions and methods for producing the genetically-modified cell, and populations of the cell, and methods for the treatment of a disease, such as cancer, using such cells.

10 Claims, 23 Drawing Sheets
Specification includes a Sequence Listing.

(56) References Cited

U.S. PATENT DOCUMENTS

| | | | |
|---|---|---|---|
| 10,093,900 | B2 | 10/2018 | Jantz et al. |
| 10,799,535 | B2 | 10/2020 | Nicholson et al. |
| 2002/0045667 | A1 | 4/2002 | Baker et al. |
| 2004/0043041 | A1 | 3/2004 | Baker et al. |
| 2012/0321667 | A1 | 12/2012 | Sentman |
| 2013/0315884 | A1 | 11/2013 | Galetto et al. |
| 2014/0034902 | A1 | 2/2014 | Hwang et al. |
| 2014/0301990 | A1 | 10/2014 | Gregory et al. |
| 2014/0349402 | A1 | 11/2014 | Cooper et al. |
| 2015/0376650 | A1 | 12/2015 | Auerbach et al. |
| 2016/0081314 | A1 | 3/2016 | Thurston et al. |
| 2016/0120906 | A1 | 5/2016 | Galetto et al. |
| 2016/0208243 | A1* | 7/2016 | Zhang ............ C12N 9/22 |
| 2017/0016027 | A1 | 1/2017 | Lee et al. |
| 2017/0333481 | A1 | 11/2017 | Jantz et al. |
| 2017/0335010 | A1 | 11/2017 | Jantz et al. |
| 2018/0289741 | A1 | 10/2018 | Nicholson et al. |
| 2018/0360883 | A1 | 12/2018 | Galetto et al. |
| 2019/0017075 | A1 | 1/2019 | Bartsevich et al. |
| 2019/0194616 | A1 | 6/2019 | Jantz et al. |

FOREIGN PATENT DOCUMENTS

| | | |
|---|---|---|
| JP | 2011-501971 A | 1/2011 |
| JP | 2013-538562 A | 10/2013 |
| WO | WO 2002/012514 A2 | 2/2002 |
| WO | WO 2007/047859 A2 | 4/2007 |
| WO | WO 2008/102199 A1 | 8/2008 |
| WO | WO 2008/102274 A2 | 8/2008 |
| WO | WO 2009/059195 A2 | 5/2009 |
| WO | WO 2010/015899 A2 | 2/2010 |
| WO | WO 2012/167192 A2 | 12/2012 |
| WO | WO 2013/074916 A1 | 5/2013 |
| WO | WO 2013/153391 A1 | 10/2013 |
| WO | WO 2013/176915 A1 | 11/2013 |
| WO | WO 2014/153470 A2 | 9/2014 |
| WO | WO 2014/191128 A1 | 12/2014 |
| WO | WO 2014/191525 A1 | 12/2014 |
| WO | WO 2014/191527 A1 | 12/2014 |
| WO | WO 2015/057980 A1 | 4/2015 |
| WO | WO 2015/121454 A1 | 8/2015 |
| WO | WO 2015/136001 A1 | 9/2015 |
| WO | WO 2015/167766 A1 | 11/2015 |
| WO | WO 2016/069282 A1 | 5/2016 |
| WO | WO 2016/069283 A1 | 5/2016 |
| WO | WO 2016/160721 A1 | 10/2016 |
| WO | WO 2017/011519 A1 | 1/2017 |
| WO | WO 2017/023801 A1 | 2/2017 |
| WO | WO 2017/062439 A1 | 4/2017 |
| WO | WO 2017/062451 A1 | 4/2017 |
| WO | WO 2017/070429 A1 | 4/2017 |
| WO | WO 2017/112859 A1 | 6/2017 |
| WO | WO 2017/156484 A1 | 9/2017 |
| WO | WO 2017/180989 A2 | 10/2017 |

OTHER PUBLICATIONS

Brickman et al. A wider context for gene trap mutagenesis. Methods in Enzymology, vol. 477, pp. 271-295, 2010. (Year: 2010).*

Koonin et al. Diversity, classification and evolution of CRISPR-Cas systems. Current Opinion in Microbiology, vol. 37, pp. 67-78, Jun. 9, 2017. (Year: 2017).*

International Search Report and Written Opinion dated Sep. 24, 2018 in connection with Application No. PCT/US2018/039740.

International Preliminary Report on Patentability dated Jan. 9, 2020 in connection with Application No. PCT/US2018/039740.

Airenne et al., "Baculovirus: an insect-derived vector for diverse gene transfer applications," Mol. Ther. 21(4), 739-749 (2013).

Altschul et al., "Basic local alignment search tool," J. Mol. Biol. 215, pp. 403-410 (1990).

Altschul et al., "Gapped BLAST and PSI-BLAST: a new generation of protein database search programs," Nucleic Acids Res. 25, pp. 3389-3402 (1997).

Arnould et al., "Engineering of large numbers of highly specific homing endonucleases that induce recombination on novel DNA targets," J. Mol. Biol. 355, pp. 443-458 (2006).

Baxter et al., "Engineering domain fusion chimeras from I-OnuI family LAGLIDADG homing endonucleases," Nucleic Acids Research, 40(16), pp. 7985-8000 (2012).

Benoist et al., "In vivo sequence requirements of the SV40 early promotor region," Nature 290(5804), pp. 304-310 (1981).

Beurdeley et al., "Compact designer TALENs for efficient genome engineering," Nat. Commun. 4, p. 1762 (2013).

Boissel et al., "megaTALs: a rare-cleaving nuclease architecture for therapeutic genome engineering," Nucleic Acid Research 42(4), pp. 2591-2601 (2014).

Cahill et al., "Mechanisms of eukaryotic DNA double strand break repair," Front. Biosci. 11, pp. 1958-1976 (2006).

Cartellieri et al., Chimeric antigen receptor-engineered T cells for immunotherapy of cancer. J Biomed Biotechnol. 2010;2010:956304. doi: 10.1155/2010/956304. Epub May 5, 2010.

Chames et al., "In vivo selection of engineered homing endonucleases using double-strand break induced homologous recombination," Nucleic Acids Res. 33, p. e178 (2005).

Chang et al., "Inducible retroviral vectors regulated by lac repressor in mammalian cells," Gene 183, pp. 137-142 (1996).

Chen et al., "A novel adenoviral vector carrying an all-in-one Tet-On system with an autoregulatory loop for tight, inducible transgene expression," BMC Biotechnol. 15, 8 pages (2015).

Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).

Cheng et al., "Dendrimers as drug carriers: applications in different routes of drug administration," J. Pharm. Sci. 97(1): 123-143 (2008).

Chevalier and Stoddard, "Homing endonucleases: structural and functional insight into the catalysts of intron/intein mobility," Nucleic Acids Res. 29(18), pp. 3757-3774 (2001).

Cots et al., "Helper dependent adenovirus vectors: progress and future prospects," Curr. Gene Ther. 13(5) pp. 370-381 (2013).

Declaration of Interference filed Aug. 19, 2019 before the USPTO Patent Trial and Appeal Board on behalf of Derek Jantz (U.S. Pat. No. 10,093,899; U.S. Pat. No. 9,993,501; U.S. Pat. No. 9,950,010) against Roman Galetto (U.S. Appl. No. 16/027,629). Patent Interference No. 106,118. 8 pages.

Declaration of Interference filed Aug. 19, 2019 before the USPTO Patent Trial and Appeal Board on behalf of Derek Jantz (U.S. Pat. No. 10,093,900; U.S. Pat. No. 9,993,502; U.S. Pat. No. 9,969,975; U.S. Pat. No. 9,950,011; U.S. Pat. No. 9,889,161; U.S. Pat. No. 9,889,160) against Roman Galetto (U.S. Appl. No. 16/027,629). Patent Interference No. 106,117. 10 pages.

Deshayes et al., "Cell-penetrating peptides: tools for intracellular delivery of therapeutics," Cell Mol. Life Sci. 62, pp. 1839-1849 (2005).

Deshayes et al., "Primary amphipathic cell-penetrating peptides: structural requirements and interactions with model membranes," Biochemistry 43, pp. 7698-7706 (2004).

Dinda et al., "Nanobiotechnology-based drug delivery in brain targeting," Curr. Pharm. Biotechnol. 14, pp. 1264-1274 (2013).

Dingermann et al., "Establishment of a system for conditional gene expression using an inducible tRNA suppressor gene," Mol. Cell Biol. 12(9), pp. 4038-4045 (1992).

Durai et al., "Zinc finger nucleases: custom-designed molecular scissors for genome engineering of plant and mammalian cells," Nucleic Acids Res. 33, pp. 5978-5990 (2005).

Ellebrecht et al., "Reengineering chimeric antigen receptor T cells for targeted therapy of autoimmune disease," Science. Jul. 8, 2016;353(6295):179-84. doi: 10.1126/science.aaf6756. Epub Jun. 30, 2016. Author manuscript.

Eyquem et al., Targeting a CAR to the TRAC locus with CRISPR/Cas9 enhances tumour rejection. Nature. Mar. 2, 2017;543(7643):113-117. doi: 10.1038/nature21405. Epub Feb. 22, 2017.

Fu et al., "High-frequency off-target mutagenesis induced by CRISPR-Cas nucleases in human cells," Nat. Biotechnol. 31, pp. 822-826 (2013).

(56) References Cited

OTHER PUBLICATIONS

Gao et al., "Efficient gene delivery into mammalian cells mediated by a recombinant baculovirus containing a whispovirus iel promoter, a novel shuttle promoter between insect cells and mammalian cells," J. Biotechnol. 131(2), pp. 138-143 (2007).
Gish et al., "Identification of protein coding regions by database similarity search," Nature Genet. 3, pp. 266-272 (1993).
Grizot et al., "Efficient targeting of a SCID gene by an engineered single-chain homing endonuclease," Nucleic Acids Res. 37, pp. 5405-5419 (2009).
Haase, et al., "Generation of a tumor- and tissue-specific episomal non-viral vector system," BMC Biotechnol. 13, pp. 49-54 (2013).
Hale et al., "Homology-Directed Recombination for Enhanced Engineering of Chimeric Antigen Receptor T Cells," Molecular Therapy 4, pp. 192-203 (2017).
Hegde et al., "Current status of chimeric antigen receptor engineered T cell-based and immune checkpoint blockade-based cancer immunotherapies," Cancer Immunol Immunother 66, pp. 1113-1121 (2017).
Hudecz et al., "Medium-sized peptides as built in carriers for biologically active compounds," Med. Res. Rev. 25, pp. 679-736 (2005).
Ibarra et al., "Efficient Targeted Gene Modification in Primary Human Hematopoietic Cells Using Co-Delivery of Nuclease mRNA and AAV Donors," Mol. Ther., 23(suppl. 1), p. S273 (2015).
Imai et al., Chimeric receptors with 4-1BB signaling capacity provoke potent cytotoxicity against acute lymphoblastic leukemia. Leukemia. Apr. 2004;18(4):676-84.
Jacox et al., "Tissue-specific and ubiquitous expression patterns from alternative promoters of human genes," PLoS One 5(8), p. e12274 (2010).
Jearawiriyapaisam et al., "Sustained dystrophin expression induced by peptide-conjugated morpholino oligomers in the muscles of mdx mice," Mol. Ther. 16, pp. 1624-1629 (2008).
Jiang et al., "Cationic core-shell liponanoparticles for ocular gene delivery," Biomaterials. 33(30), pp. 7621-7630 (2012).
Kang et al., "Harnessing the capacity of cell-penetrating peptides for drug delivery to the central nervous system," Curr. Pharm. Biotechnol. 15(3), pp. 220-230 (2014).
Karlin et al., Applications and statistics for multiple high-scoring segments in molecular sequences. Proc Natl Acad Sci U S A. Jun. 15, 1993;90(12):5873-7.
Kramer et al., "In vitro and in vivo comparative study of chimeric liver-specific promoters," Mol. Ther. 7, pp. 375-385 (2003).
Kunkel, Rapid and efficient site-specific mutagenesis without phenotypic selection. Proc Natl Acad Sci U S A. Jan. 1985;82(2):488-92.
Lee et al., "Efficient Generation of CART Cells by Homology Directed Transgene Integration into the TCR-Alpha Locus," Molecular Therapy, vol. 24, Supplement 1, S130 (May 2016).
Lentz, et al., "Viral vectors for gene delivery to the central nervous system," Neurobiol. Dis. 48, pp. 179-188 (2012).
Li et al., "Generation of single-chain LAGLIDADG homing endonucleases from native homodimeric precursor proteins," Nucleic Acids• Res. 37, pp. 1650-1662 (2009).
Liu et al., "Therapeutic levels of factor IX expression using a muscle-specific promoter and adeno-associated virus serotype 1 vector," Hum. Gene Ther. 15, pp. 783-792 (2004).
Macleod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 1, 2016;24(S1):S156. Abstract.
Macleod et al., Integration of a CD19 CAR into the TCR Alpha Chain Locus Streamlines Production of Allogeneic Gene-Edited CAR T Cells. Molecular Therapy. Apr. 2017;25(4):949-961.
Madden et al., "Applications of network BLAST server," Meth. Enzymol. 266, pp. 131-141 (1996).
Mak et al., "TAL effectors: function, structure, engineering and applications," Curr. Opin. Struct. Biol. 23, pp. 93-99 (2013).

Mali et al., "Cas9 as a versatile tool for engineering biology," Nat. Methods 10, pp. 957-963 (2013).
Mao et al., "Comparison of nonhomologous end joining and homologous recombination in human cells," DNA Repair 7(10), pp. 1765-1771 (2008). Author's manuscript.
Martin et al., "Gene delivery to the eye using adeno-associated viral vectors," Methods 28, pp. 267-275 (2002).
Mastorakos et al., "Hydroxyl PAMAM dendrimer-based gene vectors for transgene delivery to human retinal pigment epithelial cells," Nanoscale 7(9), pp. 3845-3856 (2015).
McCall et al., "Pathogen-inspired drug delivery to the central nervous system," Tissue Barriers. 2(4), e944449; 12 pages (2014).
McCarty et al., "Self-complementary recombinant adeno-associated virus (scAAV) vectors promote efficient transduction independently of DNA synthesis," Gene Ther. 8, pp. 1248-1254 (2001).
Mishra et al., "Recent applications of liposomes in ophthalmic drug delivery," J. Drug Deliv. 2011, pp. 1-14 (2011).
Mombaerts et al., Mutations in T-cell antigen receptor genes alpha and beta block thymocyte development at different stages. Nature. Nov. 19, 1992;360(6401):225-31. Erratum in Nature Dec. 3, 1992;360(6403):491.
Morgan et al., "Genetic Modification of T Cells," Biomedicines 4, pp. 1-14 (2016).
Papapetrou et al., "Gene Insertion Into Genomic Safe Harbors for Human Gene Therapy," Molecular Therapy 24(4), pp. 678-684 (2016).
Pham et al., "Generation of CAR-T Cells Lacking T Cell Receptor and Human Leukocyte Antigen Using Engineered Meganucleases" Molecular Therapy, 24(suppl. 1), p. S78 (2016).
Poirot et al., "Multiplex Genome-Edited T-cell Manufacturing Platform for "Off-the-Shelf" Adoptive T-cell Immunotherapies," Cancer Research, 75(18), pp. 3853-3864 (2015).
Qasim et al., "First Clinical Application of Talen Engineered Universal CAR19 T Cells in B-ALL," Blood 126(2046), pp. 1-3 (2015). Abstract only.
Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.
Ran et al., "Genome engineering using the CRISPR-Cas9 system," Nat. Protoc. 8, pp. 2281-2308 (2013).
Reyon et al., "FLASH assembly of TALENs for high-throughput genome editing," Nat Biotechnol. May 2012;30(5):460-5. doi: 10.1038/nbt.2170. Author manuscript.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Sather et al., "Efficient modification of CCR5 in primary human hematopoietic cells using a megaTAL nuclease and AAV donor template," Science Translation Medicine. 7(307), pp. 1-14 (2015).
Seffernick et al., Melamine deaminase and atrazine chlorohydrolase: 98 percent identical but functionally different. J Bacteriol. Apr. 2001;183(8):2405-10.
Seligman et al., "Mutations altering the cleavage specificity of a homing endonuclease," Nucleic Acids Res. 30, pp. 3870-3879 (2002).
Sha et al., "Chimaeric antigen receptor T-cell therapy for tumour immunotherapy," Bioscience Reports 37, pp. 1-12 (2017).
Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.
Sharma et al., "Next generation delivery system for proteins and genes of therapeutic purpose: why and how?" Biomed Res Int. 2014;2014:327950. doi: 10.1155/2014/327950. Epub Jul. 15, 2014.
Simeoni et al., "Insight into the mechanism of the peptide-based gene delivery system MPG: implications for delivery of siRNA into mammalian cells," Nucleic Acids Res. 31, pp. 2717-2724 (2003).
Smith et al., A combinatorial approach to create artificial homing endonucleases cleaving chosen sequences. Nucleic Acids Res. 2006;34(22):e149. Epub Nov. 27, 2006.

(56) References Cited

OTHER PUBLICATIONS

Sowa et al., "In vitro and in vivo testing of a novel regulatory system for gene therapy for intervertebral disc degeneration," Spine, 36(10), pp. E623-E628 (2011).
Spear et al., "Strategies to genetically engineer T cells for cancer immunotherapy," Cancer Immunol Immunother. Jun. 2016;65(6):631-49. doi: 10.1007/s00262-016-1842-5. Epub May 2, 2016. Author manuscript.
Stoddard, Homing endonuclease structure and function. Q Rev Biophys. Feb. 2005;38(1):49-95. Epub Dec. 9, 2005.
Sussman et al., "Isolation and characterization of new homing endonuclease specificities at individual target site positions," J. Mol. Biol. 342, pp. 31-41 (2004).
Tamboli et al. Polymeric vectors for ocular gene delivery. Ther Deliv. Apr. 2011;2(4):523-36. doi: 10.4155/tde.11.20. Author manuscript.
Tammana et al., 4-1BB and CD28 signaling plays a synergistic role in redirecting umbilical cord blood T cells against B-cell malignancies. Hum Gene Ther. Jan. 2010;21(1):75-86. doi: 10.1089/hum.2009.122.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):Mar. 18, 2012. doi: 10.1098/rstb.2012.0318.
Thomsen et al., "Promoter-regulatory region of the major immediate early gene of human cytomegalovirus," Proc. Natl. Acad. Sci. USA 81(3), pp. 659-663 (1984).
Tong et al., "Eye drop delivery of nano-polymeric micelle formulated genes with cornea-specific promoters," J. Gene Med. 9(11), pp. 956-966 (2007).
Torikai et al., "A foundation for universal T-cell based immunotherapy: T cells engineered to express a CD19-specific chimeric-antigen-receptor and eliminate expression of endogenous TCR," Blood 119(24), pp. 5697-5705 (2012).
Torikai et al., Toward eliminating HLA class I expression to generate universal cells from allogeneic donors. Blood. Aug. 22, 2013;122(8):1341-9. doi: 10.1182/blood-2013-03-478255. Epub Jun. 5, 2013.
Vannucci et al., "Viral vectors: a look back and ahead on gene transfer technology," New Microbiol. 36, pp. 1-22 (2013).
Witkowski et al., Conversion of a beta-ketoacyl synthase to a malonyl decarboxylase by replacement of the active-site cysteine with glutamine. Biochemistry. Sep. 7, 1999;38(36):11643-50.
Yoshikai et al., "Organization and sequences of the variable joining and constant region genes of the human t cell receptor alpha-chain," Nature, 316(6031), pp. 837-840 (1985).
Yuasa et al., "Adeno-associated virus vector-mediated gene transfer into dystrophin-deficient skeletal muscles evokes enhanced immune response against the transgene product," Gene Ther. 9, pp. 1576-1588 (2002).

Zhang et al., "A greedy algorithm for aligning DNA sequences," J. Comput. Biol. 7(1-2), pp. 203-214 (2000).
Zhang et al., "Engineering CAR-T cells," Biomarker Research 5(22), pp. 1-6 (2017).
Zuris et al., "Efficient Delivery of Genome-Editing Proteins In Vitro and In Vivo," Nat. Biotechnol. 33, pp. 73-80 (2015). Author's manuscript. Published online Oct. 30, 2014. doi: 10.1038/nbt.3081.
Extended European Search Report dated Jun. 6, 2020 in connection with Application No. EP 19212310.7.
International Search Report and Written Opinion dated Dec. 19, 2016 for Application No. PCT/US2016/055472.
International Preliminary Report on Patentability dated Apr. 19, 2018 for Application No. PCT/US2016/055472.
Extended European Search Report dated Nov. 26, 2020 in connection with Application No. EP 20172471.3.
International Search Report and Written Opinion for Application No. PCT/US2016/055492 dated Feb. 3, 2017.
International Preliminary Report on Patentability dated Apr. 19, 2018 for Application No. PCT/US2016/055492.
International Search Report and Written Opinion for Application No. PCT/US2016/068289 dated Jun. 8, 2017.
International Preliminary Report on Patentability for Application No. PCT/US2016/068289 dated Jul. 5, 2018.
International Search Report and Written Opinion for Application No. PCT/US2019/0270190 dated Jun. 27, 2019.
International Preliminary Report on Patentability for Application No. PCT/US2019/0270190 dated Oct. 22, 2020.
[No Author Listed], Genbank Accession No. BDV42890. TRC 1-2x.87 EE meganuclease, SEQ ID 8. Jun. 1, 2017; 1 page.
[No Author Listed], Genbank Accession No. BDV42894. TRC 1-2x.6 meganuclease, SEQ ID 12. Jun. 1, 2017; 1 page.
[No Author Listed], Genbank Accession No. BDV42944. TRC 1-2x.6 meganuclease 7-153, SEQ ID 62. Jun. 1, 2017; 1 page.
[No Author Listed], Genbank Accession No. BDV43178. Chlamydomonas reinhardtii CreI meganuclease, SEQ ID 8. Jun. 15, 2017; 1 page.
[No Author Listed], Genbank Accession No. BDV43182. Chlamydomonas reinhardtii CreI meganuclease, SEQ ID 12. Jun. 15, 2017; 1 page.
[No Author Listed], Genbank Accession No. BDV43232. Chlamydomonas reinhardtii CreI meganuclease, SEQ ID 62. Jun. 15, 2017; 1 page.
[No Author Listed], Genbank Accession No. BEA51599. TRC 1-2x.87 EE meganuclease, SEQ ID 131. Aug. 10, 2017; 1 page.
Provasi et al., Editing T cell specificity towards leukemia by zinc finger nucleases and lentiviral gene transfer. Nat Med. May 2012;18(5):807-815. doi: 10.1038/nm.2700.
Van De Loo et al., An oleate 12-hydroxylase from *Ricinus communis* L. is a fatty acyl desaturase homolog. Proc Natl Acad Sci U S A. Jul. 18, 1995;92(15):6743-7. doi: 10.1073/pnas.92.15.6743.

\* cited by examiner

```
                        TRC11         TRC12
                      Half-Site     Half-Site TRC 11-12             TGATAGCTTGTGCTGTCCCTG    SEQ ID NO:4
Recognition Sequence  ACTATCGAACACGGACAGGGAC   SEQ ID NO:5

TRC15         TRC16
                      Half-Site     Half-Site

TRC 15-16             CAGTTTGCTTTGCTGGGCCTTT   SEQ ID NO:6
Recognition Sequence  GTCAAACGAAACGACCCGGAAA   SEQ ID NO:7

TRC17         TRC18
                      Half-Site     Half-Site

TRC 17-18             TGCTGTGACTTGCTCAAGGCCT   SEQ ID NO:8
Recognition Sequence  ACGACACTGAACGAGTTCCGGA   SEQ ID NO:9

TRC19         TRC20
                      Half-Site     Half-Site

TRC 19-20             TGGGTTGGGGCAAAGAGGGAAA   SEQ ID NO:10
Recognition Sequence  ACCCAACCCCGTTTCTCCCTTT   SEQ ID NO:11
```

FIGURE 2

A.
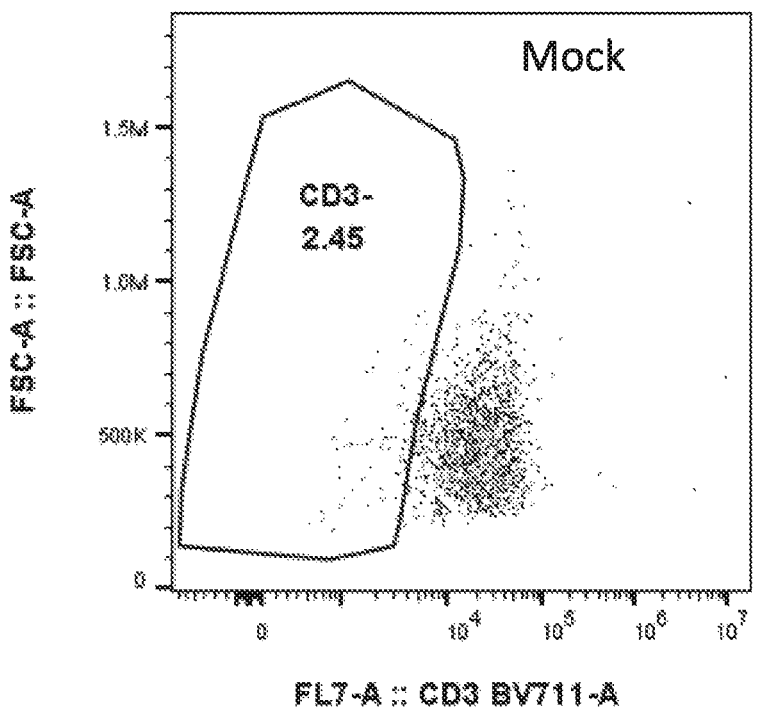
B.
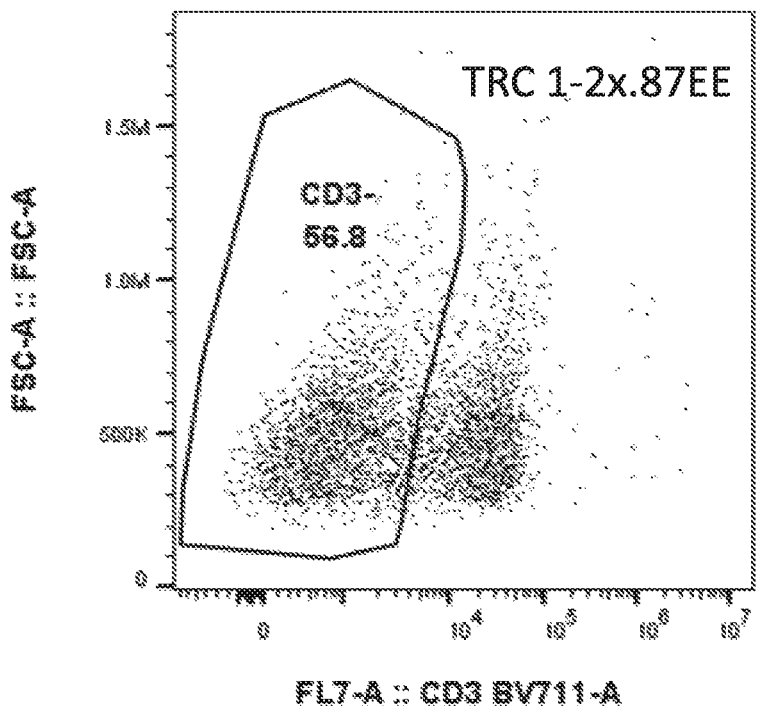
FIGURE 8

C.
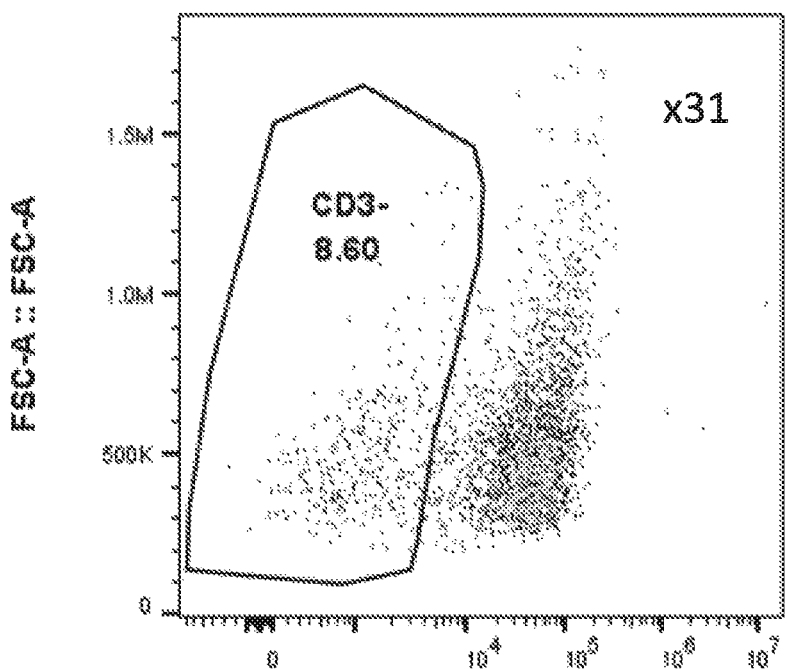
D.
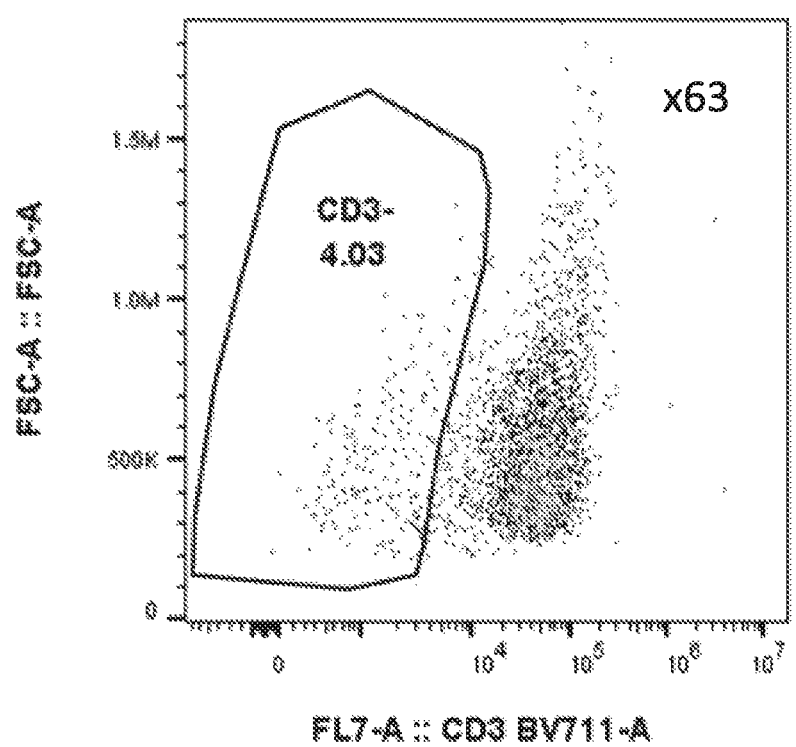
FIGURE 8 (cont.)

E.
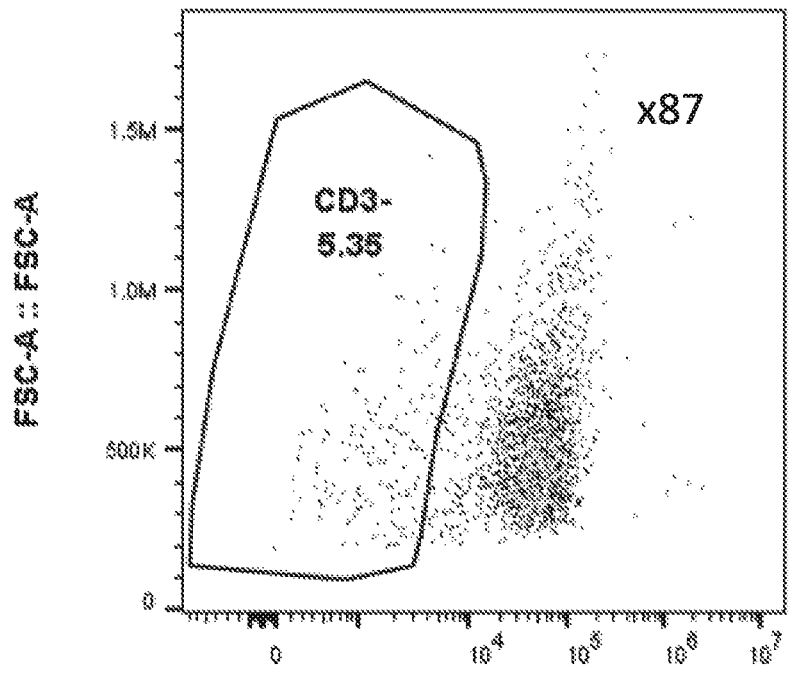
F.
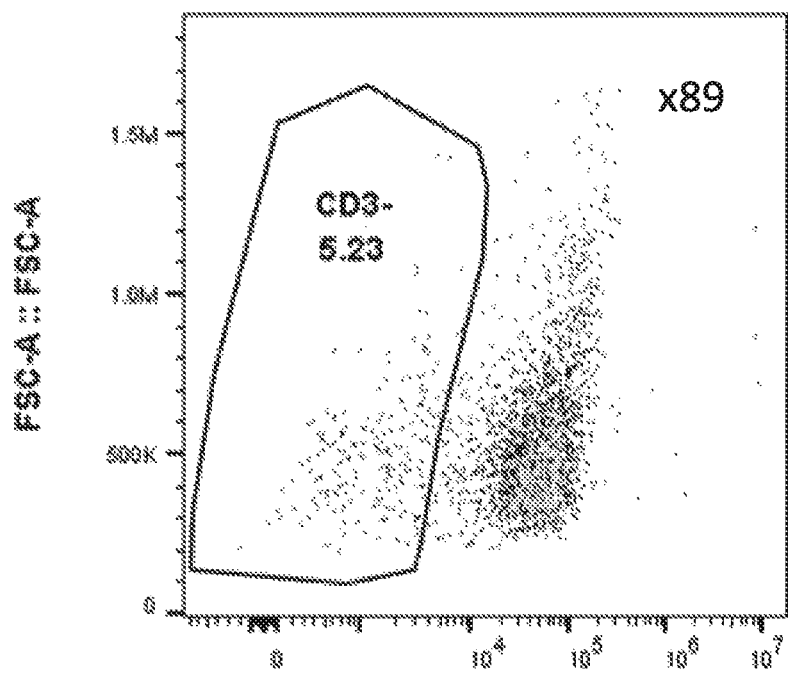
FIGURE 8 (cont.)

TRC 11-12 site
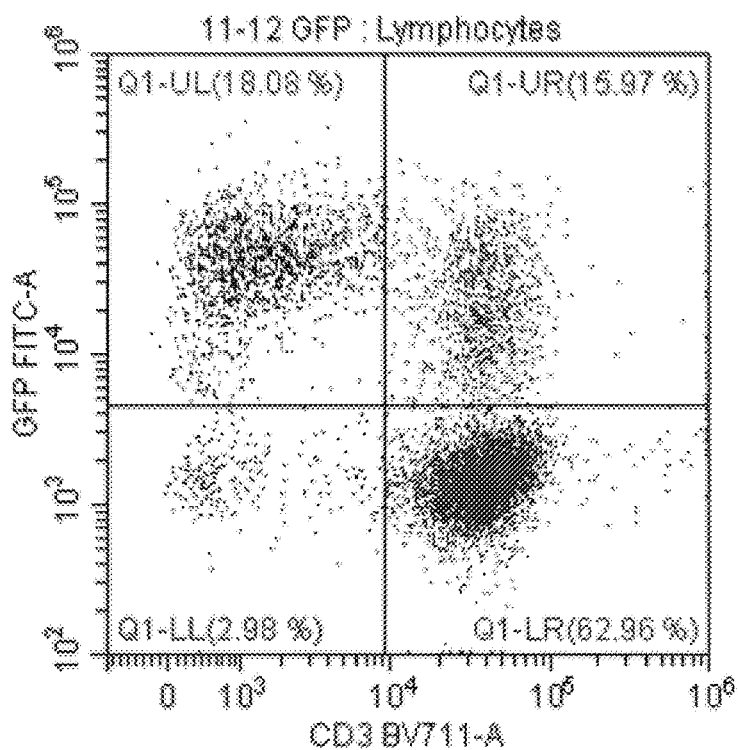
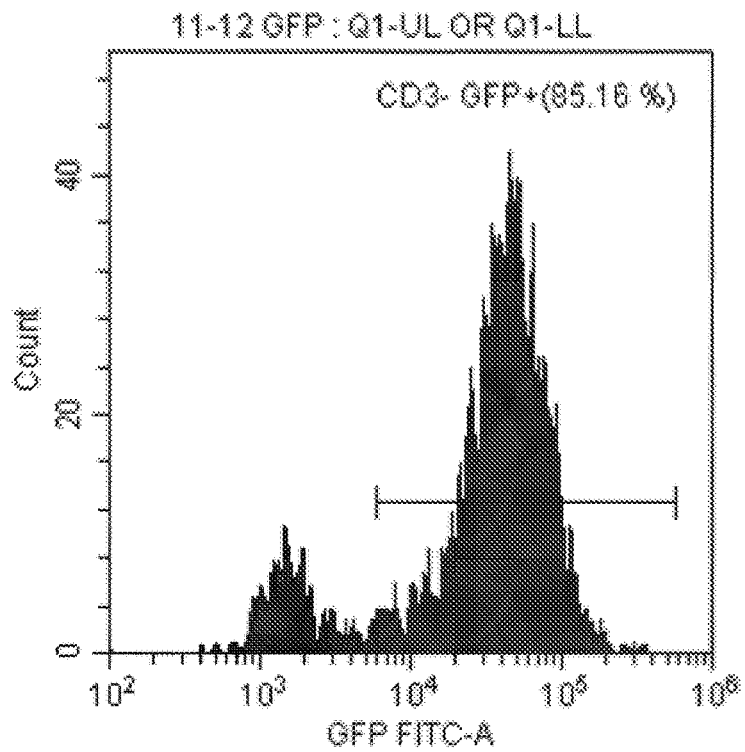
FIGURE 10

TRC 15-16 site
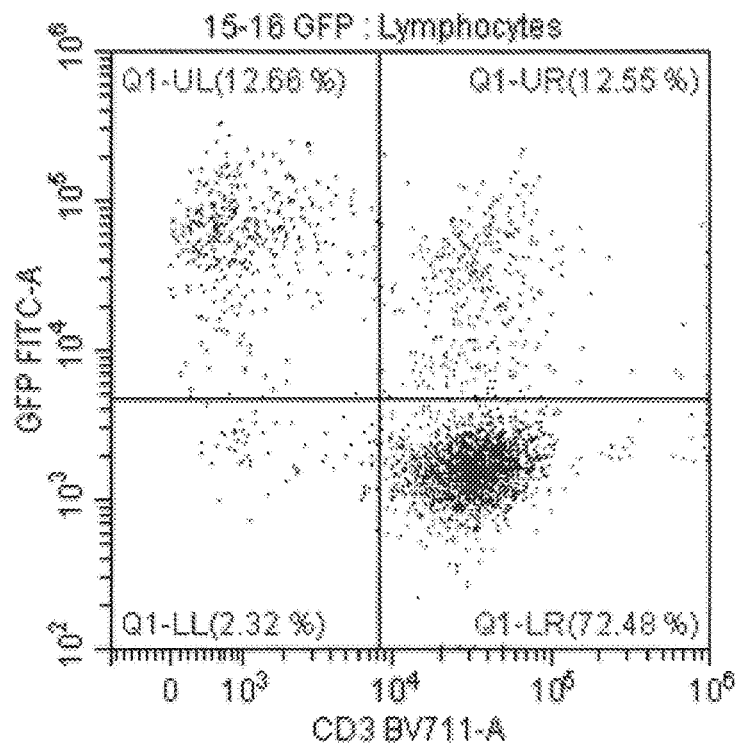
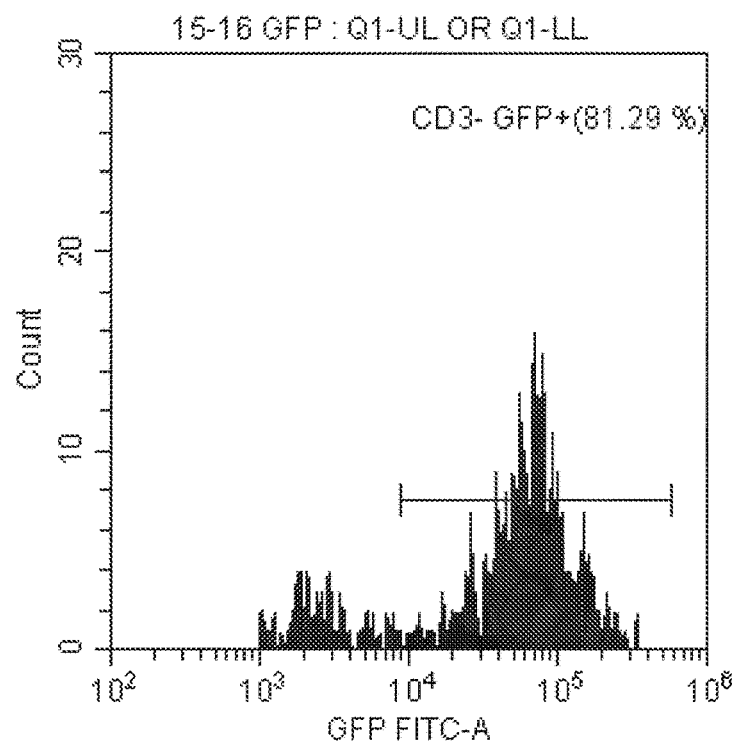
FIGURE 10 (cont.)

C.

US 11,053,484 B2

GENETICALLY-MODIFIED T CELLS COMPRISING A MODIFIED INTRON IN THE T CELL RECEPTOR ALPHA GENE

RELATED APPLICATIONS

This application is a national stage filing under 35 U.S.C. § 371 of international application number PCT/US2018/039740, filed Jun. 27, 2018, which claims the benefit of U.S. provisional application No. 62/527,845, filed Jun. 30, 2017 and U.S. provisional application No. 62/579,473, filed Oct. 31, 2017, each of which is herein incorporated by reference in its entirety.

FIELD OF THE INVENTION

The invention relates to the fields of oncology, cancer immunotherapy, molecular biology and recombinant nucleic acid technology. In particular, the invention relates to genetically-modified T cells comprising a modified intron in the T cell receptor alpha gene that is 5' upstream of TRAC exon 1, as well as compositions and methods for making the same. The invention further relates to methods of using such cells for treating a disease, including cancer, in a subject.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 30, 2019, is named P109070024US02-SEQ-MJT, and is 121 kilobytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor or an exogenous T cell receptor to graft antigen specificity onto the T cell. By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CAR T cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, it would be advantageous to develop "off the shelf" CAR T cells, prepared using T cells from a third party, healthy donor, that have reduced expression of the endogenous T cell receptor and do not initiate GVHD upon administration. Such products could be generated and validated in advance of diagnosis, and could be made available to patients as soon as necessary. Therefore, a need exists for the development of allogeneic CAR T cells that lack an endogenous T cell receptor in order to prevent the occurrence of GVHD.

Genetic modification of genomic DNA can be performed using site-specific, rare-cutting endonucleases that are engineered to recognize DNA sequences in the locus of interest. Methods for producing engineered, site-specific endonucleases are known in the art. For example, zinc-finger nucleases (ZFNs) can be engineered to recognize and cut pre-determined sites in a genome. ZFNs are chimeric proteins comprising a zinc finger DNA-binding domain fused to the nuclease domain of the FokI restriction enzyme. The zinc finger domain can be redesigned through rational or experimental means to produce a protein that binds to a pre-determined DNA sequence ~18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in Durai et al. (2005), Nucleic Acids Res 33, 5978). Likewise, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak et al. (2013), Curr Opin Struct Biol. 23:93-9). In this case, however, the DNA binding domain comprises a tandem array of TAL-effector domains, each of which specifically recognizes a single DNA basepair. A limitation that ZFNs and TALENs have for the practice of the current invention is that they are heterodimeric, so that the production of a single functional nuclease in a cell requires co-expression of two protein monomers.

Compact TALENs have an alternative endonuclease architecture that avoids the need for dimerization (Beurdeley et al. (2013), Nat Commun. 4:1762). A Compact TALEN comprises an engineered, site-specific TAL-effector DNA-binding domain fused to the nuclease domain from the I-TevI homing endonuclease. Unlike FokI, I-TevI does not need to dimerize to produce a double-strand DNA break so a Compact TALEN is functional as a monomer.

Engineered endonucleases based on the CRISPR system are also known in the art (Ran et al. (2013), Nat Protoc. 8:2281-2308; Mali et al. (2013), Nat Methods 10:957-63). A CRISPR endonuclease comprises two components: (1) a Cas effector nuclease, typically microbial Cas9, Cpf1, or another suitable nuclease; and (2) a short "guide RNA" comprising a ~20 nucleotide targeting sequence that directs the nuclease to a location of interest in the genome. By expressing multiple guide RNAs in the same cell, each having a different targeting sequence, it is possible to target DNA breaks simultaneously to multiple sites in the genome. Thus, CRISPR nucleases are suitable for the present invention. The primary drawback of the CRISPR system is its reported high frequency of off-target DNA breaks, which could limit the utility of the system for treating human patients (Fu et al. (2013), Nat Biotechnol. 31:822-6).

Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), Nucleic Acids Res. 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers.

I-CreI (SEQ ID NO: 1) is a member of the LAGLIDADG (SEQ ID NO: 2) family of homing endonucleases that recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J. Mol. Biol. 342: 31-41; Chames et al. (2005), Nucleic Acids Res. 33: e178; Seligman et al. (2002), Nucleic Acids Res. 30: 3870-9, Arnould et al. (2006), J. Mol. Biol. 355: 443-58). More recently, a method of rationally-designing mono-LAGLIDADG (SEQ ID NO:2) homing endonucleases was described that is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), Nucleic Acids Res. 37:1650-62; Grizot et al. (2009), Nucleic Acids Res. 37:5405-19). Thus, a functional "single-chain" meganuclease can be expressed from a single transcript.

The use of engineered meganucleases for cleaving DNA targets in the human T cell receptor alpha gene has been previously disclosed. For example, in International Publication Nos. WO 2017/062439 and WO 2017/062451, Applicants disclosed engineered meganucleases having specificity for recognition sequences in the T cell receptor alpha constant region (TRAC) gene exon 1. The '439 and '451 publications also disclosed methods for targeted insertion of a CAR coding sequence into the meganuclease cleavage sites. Further, International Publication No. WO 2014/191527 disclosed variants of the I-OnuI meganuclease that were also engineered to target a recognition sequence (SEQ ID NO: 3 of the '527 publication) within TRAC exon 1. Although the '527 publication discusses that a chimeric antigen receptor can be expressed in TCR knockout cells, the authors did not disclose the insertion of the CAR coding sequence into the meganuclease cleavage site.

The use of other nucleases and mechanisms for disrupting expression of the endogenous TCR have also been disclosed, including small-hairpin RNAs, zinc finger nucleases (ZFNs), transcription activator-like effector nucleases (TALENs), megaTALs, and CRISPR systems (e.g., Osborn et al. (2016), Molecular Therapy 24(3): 570-581; U.S. Pat. No. 8,956,828; U.S. Publication No. US2014/0301990; U.S. Publication No. US2012/0321667).

Additionally, Eyquem et al. ((2017), Nature 543: 113-117) disclosed the use of a CRISPR/Cas9 system to target insertion of a CAR coding sequence into a site that spans both the 5' end of TRAC exon 1 and the endogenous splice acceptor site that is positioned immediately 5' upstream of TRAC exon 1. The authors describe that the expected double-strand cleavage site of the Cas9 nuclease is within the splice acceptor site (see, Eyquem, Supplementary FIG. 1A). This splice acceptor site is necessary for TCR expression, as evidenced by the fact that disruption of the site by Cas9, in the absence of a donor template, results in TCR knockout in 70% of T cells (see, Eyquem, Supplemental FIG. 1C, second panel).

Notably, nucleases and CRISPR systems disclosed in the prior art each target recognition sequences in T cell receptor genes at sites or loci that are critical for expression of the gene and formation of a functional T cell receptor; e.g., TRAC exons, or the endogenous splice acceptor site. Although insertion of a CAR coding sequence into these cleavage sites can result in T cell receptor negative (TCR−) cells which are CAR positive (CAR+), a significant disadvantage to this approach is that TCR expression can be knocked out by error-prone non-homologous end-joining (NHEJ) at the cleavage site when no donor template is inserted.

As a result, previous methods for producing CAR T cells result in mixed populations of TCR−/CAR+ and TCR−/CAR− cells that would require further enrichment for pre-clinical and clinical use. For example, as previously discussed, Supplemental FIG. 1C of Eyquem shows that ~70% of cells were TCR−/CAR− when Cas9 disrupted the splice acceptor site 5' upstream of TRAC exon 1 when no donor template is present. However, even in the presence of a CAR donor template (1e6 AAV6), mixed populations of TCR−/CAR− and TCR−/CAR+ cells were produced. Specifically, when template DNA was provided by an AAV6 MOI of 1e6, 45.6% of T cells were TCR−/CAR+, but a substantial percentage of cells (30.7%) were TCR−/CAR− due to cleavage within the splice acceptor site by Cas9 and subsequent error-prone repair by NHEJ.

By contrast, the present invention takes a counter-intuitive approach for modifying T genes and inserting sequences of interest, such as CAR coding sequences. Rather than targeting elements of TCR genes that are essential for TCR expression, the present invention targets the intron in the TCR alpha gene that is 5' upstream of TRAC exon 1. As long as the endogenous splice donor site and the endogenous splice acceptor site which flank the intron are not modified, double-strand cleavage by a nuclease within this non-coding intron would have no substantive effect on TCR expression, even if NHEJ produced an indel at the cleavage site.

By going against convention and targeting recognition sequences in the intron, TCR expression is only disrupted when a sequence of interest, comprising at least an exogenous splice acceptor site and/or a poly A signal, is inserted into the cleavage site, for example, by homologous recombination. As a result, TCR− cells produced according to the invention will comprise the sequence of interest inserted into the intron cleavage site. By extension, in cases where the inserted sequence of interest further includes a CAR coding sequence, most or all of the TCR– cells in the resulting population of cells will be TCR–/CAR+, which stands in stark contrast to previous methods in which the resulting population would also include a substantial percentage of cells that are TRC–/CAR–. Thus, the invention significantly advances the field by eliminating the burdensome need for enrichment of CAR+ cells from a mixed population of TRC– cells.

Further, in some embodiments of the invention, the sequence of interest inserted into the intron comprises a 2A element (see, FIG. 1) 5' upstream of a coding sequence (e.g., a CAR coding sequence). The inclusion of this 2A element allows for expression of the coding sequence to be driven by the endogenous T cell receptor alpha gene promoter, rather than by an exogenous promoter. In this manner, expression of a polypeptide such as a CAR can be regulated by the T cell feedback mechanisms normally associated with TCR expression.

SUMMARY OF THE INVENTION

The present invention provides a genetically-modified human T cell, or a cell derived therefrom, comprising in its genome a modified human T cell receptor alpha gene. The modified human T cell receptor alpha gene can comprise an exogenous sequence of interest inserted into an intron within the T cell receptor alpha gene that is positioned 5' upstream of TRAC exon 1. The exogenous sequence of interest inserted into the intron can comprise an exogenous splice acceptor site and/or a poly A signal, which disrupts expression of the T cell receptor alpha subunit. In some embodiments, the sequence of interest can also include a coding sequence for a polypeptide (e.g., a CAR coding sequence). Additionally, the endogenous splice donor site and the endogenous splice acceptor site flanking the intron are unmodified and/or remain functional in the cell. Further, cell surface expression of an endogenous T cell receptor is reduced when compared to an unmodified control cell.

The present invention also provides compositions and methods for producing the genetically-modified T cell, as well as populations of T cells. The present invention further provides a method of immunotherapy for treating cancer by administering the genetically-modified T cell, wherein the T cell expresses a receptor for a tumor-specific antigen (e.g. a CAR).

Thus, in one aspect, the invention provides an engineered meganuclease that recognizes and cleaves a recognition sequence within an intron in the human T cell receptor alpha gene that is positioned 5' upstream of TRAC exon 1, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region. In some embodiments, the intron comprises SEQ ID NO: 3, and the engineered meganuclease does not have a recognition sequence within the endogenous splice donor site or the endogenous splice acceptor site flanking said intron.

In certain embodiments, the recognition sequence comprises SEQ ID NO: 4 (i.e., the TRC 11-12 recognition sequence).

In some such embodiments, the HVR1 region comprises an amino acid sequence having at least 80%, at least 85%, at least 90%, at least 95%, or more, sequence identity to an amino acid sequence corresponding to residues 215-270 of any one of SEQ ID NOs: 12-15.

In some such embodiments, the HVR1 region comprises residues corresponding to residues 215, 217, 219, 221, 223, 224, 229, 231, 233, 235, 237, 259, 261, 266, and 268 of any one of SEQ ID NOs: 12-15.

In some such embodiments, the HVR1 region comprises residues 215-270 of any one of SEQ ID NOs: 12-15.

In some such embodiments, the HVR2 region comprises an amino acid sequence having at least 80%, at least 85%, at least 90%, at least 95%, or more, sequence identity to an amino acid sequence corresponding to residues 24-79 of any one of SEQ ID NOs: 12-15.

In some such embodiments, the HVR2 region comprises residues corresponding to residues 24, 26, 28, 30, 32, 33, 38, 40, 42, 44, 46, 68, 70, 75, and 77 of any one of SEQ ID NOs: 12-15.

In some such embodiments, the HVR2 region comprises residues 24-79 of any one of SEQ ID NOs: 12-15.

In some such embodiments, the first subunit comprises an amino acid sequence having at least 80%, at least 85%, at least 90%, at least 95%, or more, sequence identity to residues 198-344 of any one of SEQ ID NOs: 12-15, and wherein the second subunit comprises an amino acid sequence having at least 80%, at least 85%, at least 90%, at least 95%, or more, sequence identity to residues 7-153 of any one of SEQ ID NOs: 12-15.

In some such embodiments, the first subunit comprises residues 198-344 of any one of SEQ ID NOs: 12-15. In some such embodiments, the second subunit comprises residues 7-153 of any one of SEQ ID NOs: 12-15.

In some such embodiments, the engineered meganuclease comprises a linker, wherein the linker covalently joins the first subunit and the second subunit.

In some such embodiments, the engineered meganuclease comprises the amino acid sequence of any one of SEQ ID NOs: 12-15.

In certain embodiments, the recognition sequence comprises SEQ ID NO: 6 (i.e., the TRC 15-16 recognition sequence).

In some such embodiments, the HVR1 region comprises an amino acid sequence having at least 80%, at least 85%, at least 90%, at least 95%, or more, sequence identity to an amino acid sequence corresponding to residues 24-79 of any one of SEQ ID NOs: 16-19.

In some such embodiments, the HVR1 region comprises residues corresponding to residues 24, 26, 28, 30, 32, 33, 38, 40, 42, 44, 46, 68, 70, 75, and 77 of any one of SEQ ID NOs: 16-19.

In some such embodiments, the HVR1 region comprises a residue corresponding to residue 64 of any one of SEQ ID NOs: 16-19.

In some such embodiments, the HVR1 region comprises residues 24-79 of any one of SEQ ID NOs: 16-19.

In some such embodiments, the HVR2 region comprises an amino acid sequence having at least 80%, at least 85%, at least 90%, at least 95%, or more, sequence identity to an amino acid sequence corresponding to residues 215-270 of any one of SEQ ID NOs: 16-19.

In some such embodiments, the HVR2 region comprises residues corresponding to residues 215, 217, 219, 221, 223, 224, 229, 231, 233, 235, 237, 259, 261, 266, and 268 of any one of SEQ ID NOs: 16-19.

In some such embodiments, the HVR2 region comprises residues 215-270 of any one of SEQ ID NOs: 16-19.

In some such embodiments, the first subunit comprises an amino acid sequence having at least 80%, at least 85%, at least 90%, at least 95%, or more, sequence identity to residues 7-153 of any one of SEQ ID NOs: 16-19, and wherein the second subunit comprises an amino acid sequence having at least 80%, at least 85%, at least 90%, at least 95%, or more, sequence identity to residues 198-344 of any one of SEQ ID NOs: 16-19.

In some such embodiments, the first subunit comprises residues 7-153 of any one of SEQ ID NOs: 16-19.

In some such embodiments, the second subunit comprises residues 198-344 of any one of SEQ ID NOs: 16-19.

In some such embodiments, the engineered meganuclease comprises a linker, wherein the linker covalently joins the first subunit and the second subunit.

In some such embodiments, the engineered meganuclease comprises the amino acid sequence of any one of SEQ ID NOs: 16-19.

In certain embodiments, the recognition sequence comprises SEQ ID NO: 8 (i.e., the TRC 17-18 recognition sequence).

In some such embodiments, the HVR1 region comprises an amino acid sequence having at least 80%, at least 85%, at least 90%, at least 95%, or more, sequence identity to an amino acid sequence corresponding to residues 24-79 of any one of SEQ ID NOs: 20-23.

In some such embodiments, the HVR1 region comprises residues corresponding to residues 24, 26, 28, 30, 32, 33, 38, 40, 42, 44, 46, 68, 70, 75, and 77 of any one of SEQ ID NOs: 20-23.

In some such embodiments, the HVR1 region comprises a residue corresponding to residue 66 of any one of SEQ ID NOs: 20-23.

In some such embodiments, the HVR1 region comprises residues 24-79 of any one of SEQ ID NOs: 20-23.

In some such embodiments, the HVR2 region comprises an amino acid sequence having at least 80%, at least 85%, at least 90%, at least 95%, or more, sequence identity to an amino acid sequence corresponding to residues 215-270 of any one of SEQ ID NOs: 20-23.

In some such embodiments, the HVR2 region comprises residues corresponding to residues 215, 217, 219, 221, 223, 224, 229, 231, 233, 235, 237, 259, 261, 266, and 268 of any one of SEQ ID NOs: 20-23.

In some such embodiments, the HVR2 region comprises residues 215-270 of any one of SEQ ID NOs: 20-23.

In some such embodiments, the first subunit comprises an amino acid sequence having at least 80%, at least 85%, at least 90%, at least 95%, or more, sequence identity to residues 7-153 of any one of SEQ ID NOs: 20-23, and wherein the second subunit comprises an amino acid sequence having at least 80%, at least 85%, at least 90%, at least 95%, or more, sequence identity to residues 198-344 of any one of SEQ ID NOs: 20-23.

In some such embodiments, the first subunit comprises residues 7-153 of any one of SEQ ID NOs: 20-23.

In some such embodiments, the second subunit comprises residues 198-344 of any one of SEQ ID NOs: 20-23.

In some such embodiments, the engineered meganuclease comprises a linker, wherein the linker covalently joins the first subunit and the second subunit.

In some such embodiments, the engineered meganuclease comprises the amino acid sequence of any one of SEQ ID NOs: 20-23.

In certain embodiments, the recognition sequence comprises SEQ ID NO: 10 (i.e., the TRC 19-20 recognition sequence).

In some such embodiments, the HVR1 region comprises an amino acid sequence having at least 80%, at least 85%, at least 90%, at least 95%, or more, sequence identity to an amino acid sequence corresponding to residues 24-79 of any one of SEQ ID NOs: 24-27.

In some such embodiments, the HVR1 region comprises residues corresponding to residues 24, 26, 28, 30, 32, 33, 38, 40, 42, 44, 46, 68, 70, 75, and 77 of any one of SEQ ID NOs: 24-27.

In some such embodiments, the HVR1 region comprises residues 24-79 of any one of SEQ ID NOs: 24-27.

In some such embodiments, the HVR2 region comprises an amino acid sequence having at least 80%, at least 85%, at least 90%, at least 95%, or more, sequence identity to an amino acid sequence corresponding to residues 215-270 of any one of SEQ ID NOs: 24-27.

In some such embodiments, the HVR2 region comprises residues corresponding to residues 215, 217, 219, 221, 223, 224, 229, 231, 233, 235, 237, 259, 261, 266, and 268 of any one of SEQ ID NOs: 24-27.

In some such embodiments, the HVR2 region comprises residues 215-270 of any one of SEQ ID NOs: 24-27.

In some such embodiments, the first subunit comprises an amino acid sequence having at least 80%, at least 85%, at least 90%, at least 95%, or more, sequence identity to residues 7-153 of any one of SEQ ID NOs: 24-27, and wherein the second subunit comprises an amino acid sequence having at least 80%, at least 85%, at least 90%, at least 95%, or more, sequence identity to residues 198-344 of any one of SEQ ID NOs: 24-27.

In some such embodiments, the first subunit comprises residues 7-153 of any one of SEQ ID NOs: 24-27.

In some such embodiments, the second subunit comprises residues 198-344 of any one of SEQ ID NOs: 24-27.

In some such embodiments, the engineered meganuclease comprises a linker, wherein the linker covalently joins the first subunit and the second subunit.

In some such embodiments, the engineered meganuclease comprises the amino acid sequence of any one of SEQ ID NOs: 24-27.

In another aspect, the invention provides a polynucleotide comprising a nucleic acid sequence encoding an engineered meganuclease described herein.

In certain embodiments, the polynucleotide is an mRNA.

In further embodiments, the mRNA is a polycistronic mRNA encoding an engineered meganuclease described herein and at least one additional polypeptide or nucleic acid.

In another aspect, the invention provides a recombinant DNA construct comprising the polynucleotide described herein.

In certain embodiments, the recombinant DNA construct encodes a viral vector. In particular embodiments, the viral vector is an adenoviral vector, a lentiviral vector, a retroviral vector, or an adeno-associated viral (AAV) vector. In specific embodiments, the viral vector is a recombinant AAV vector.

In another aspect, the invention provides a viral vector comprising the polynucleotide described herein.

In certain embodiments, the viral vector is an adenoviral vector, a lentiviral vector, a retroviral vector, or an AAV vector. In particular embodiments, the viral vector is a recombinant AAV vector.

In another aspect, the invention provides a method for producing a genetically-modified T cell comprising an exogenous sequence of interest inserted into a chromosome of the T cell. The method comprises introducing into a T cell one or more nucleic acids including: (a) a first nucleic acid sequence encoding an engineered meganuclease described herein, wherein the engineered meganuclease is expressed in the T cell; and (b) a second nucleic acid sequence including the sequence of interest; wherein the engineered meganuclease produces a cleavage site in the chromosome at a recognition sequence in an intron in the human T cell receptor alpha gene that is positioned 5' upstream of TRAC exon 1; and wherein the sequence of interest is inserted into the chromosome at the cleavage site; and wherein the sequence of interest comprises an exogenous splice acceptor site and/or a poly A signal; and wherein the endogenous splice donor site and the endogenous splice acceptor site flanking the intron are unmodified and/or remain functional.

In some embodiments of the method, the T cell is a precursor T cell in which rearrangement of the V and J segments has not occurred.

In certain embodiments of the method, cell surface expression of an endogenous T cell receptor is reduced when compared to an unmodified control cell.

In some embodiments of the method, the intron comprises SEQ ID NO: 3.

In some embodiments of the method, the recognition sequence comprises SEQ ID NO: 4 and the engineered meganuclease is an engineered meganuclease described herein which recognizes and cleaves SEQ ID NO: 4. In some embodiments of the method, the recognition sequence comprises SEQ ID NO: 6 and the engineered meganuclease is an engineered meganuclease described herein which recognizes and cleaves SEQ ID NO: 6. In some embodiments of the method, the recognition sequence comprises SEQ ID NO: 8 and the engineered meganuclease is an engineered meganuclease described herein which recognizes and cleaves SEQ ID NO: 8. In some embodiments of the method, the recognition sequence comprises SEQ ID NO: 10 and the engineered meganuclease is an engineered meganuclease described herein which recognizes and cleaves SEQ ID NO: 10.

In certain embodiments of the method, the second nucleic acid sequence further comprises sequences homologous to sequences flanking the cleavage site and the sequence of interest is inserted at the cleavage site by homologous recombination.

In some embodiments of the method, the T cell is a human T cell, or a cell derived therefrom.

In various embodiments of the method, the sequence of interest comprises, from 5' to 3', an exogenous splice acceptor site, a 2A element or IRES element, a coding sequence for a protein of interest, and a polyA signal. In certain embodiments of the method, the 2A element is a T2A, a P2A, an E2A, or an F2A element. In particular embodiments of the method, the 2A element is a T2A element.

In some embodiments of the method, the sequence of interest further comprises an exogenous branch site positioned 5' upstream of the exogenous splice acceptor site.

In some embodiments of the method, the sequence of interest comprises a coding sequence for a chimeric antigen receptor or an exogenous T cell receptor. In particular embodiments of the method, the chimeric antigen receptor or the exogenous T cell receptor comprises an extracellular ligand-binding domain having specificity for a tumor-specific antigen.

In some embodiments of the method, at least the first nucleic acid sequence is introduced into the T cell by an mRNA.

In certain embodiments of the method, at least the second nucleic acid sequence is introduced into the T cell by a viral vector. In particular embodiments of the method, the viral vector is an adenoviral vector, a lentiviral vector, a retroviral vector, or an AAV vector. In specific embodiments of the method, the viral vector is a recombinant AAV vector.

In another aspect, the invention provides a method for producing a genetically-modified T cell comprising an exogenous sequence of interest inserted into a chromosome of the T cell. The method comprises: (a) introducing an engineered meganuclease described herein into a T cell; and (b) transfecting the T cell with a nucleic acid including the sequence of interest; wherein the engineered meganuclease produces a cleavage site in the chromosome at a recognition sequence in an intron in the human T cell receptor alpha gene that is positioned 5' upstream of TRAC exon 1; and wherein the sequence of interest is inserted into the chromosome at the cleavage site; and wherein the sequence of interest comprises an exogenous splice acceptor site and/or a poly A signal; and wherein the endogenous splice donor site and the endogenous splice acceptor site flanking the intron are unmodified and/or remain functional.

In some embodiments of the method, the T cell is a precursor T cell in which rearrangement of the V and J segments has not occurred.

In some embodiments of the method, cell surface expression of an endogenous T cell receptor is reduced when compared to an unmodified control cell.

In certain embodiments of the method, the intron comprises SEQ ID NO: 3.

In some embodiments of the method, the recognition sequence comprises SEQ ID NO: 4 and the engineered meganuclease is an engineered meganuclease described herein which recognizes and cleaves SEQ ID NO: 4. In some embodiments of the method, the recognition sequence comprises SEQ ID NO: 6 and the engineered meganuclease is an engineered meganuclease described herein which recognizes and cleaves SEQ ID NO: 6. In some embodiments of the method, the recognition sequence comprises SEQ ID NO: 8 and the engineered meganuclease is an engineered meganuclease described herein which recognizes and cleaves SEQ ID NO: 8. In some embodiments of the method, the recognition sequence comprises SEQ ID NO: 10 and the engineered meganuclease is an engineered meganuclease described herein which recognizes and cleaves SEQ ID NO: 10.

In certain embodiments of the method, the nucleic acid further comprises sequences homologous to sequences flanking the cleavage site and the sequence of interest is inserted at the cleavage site by homologous recombination.

In some embodiments of the method, the T cell is a human T cell, or a cell derived therefrom.

In certain embodiments of the method, the sequence of interest comprises, from 5' to 3', an exogenous splice acceptor site, a 2A element or IRES element, a coding sequence for a protein of interest, and a polyA signal. In particular embodiments of the method, the 2A element is a T2A, a P2A, an E2A, or an F2A element. In specific embodiments of the method, the 2A element is a T2A element.

In some embodiments of the method, the sequence of interest further comprises an exogenous branch site positioned 5' upstream of the exogenous splice acceptor site.

In some embodiments of the method, the sequence of interest comprises a coding sequence for a chimeric antigen receptor or an exogenous T cell receptor. In particular embodiments of the method, the chimeric antigen receptor or the exogenous T cell receptor comprises an extracellular ligand-binding domain having specificity for a tumor-specific antigen.

In certain embodiments of the method, the nucleic acid is introduced into the T cell by a viral vector. In particular embodiments of the method, the viral vector is an adenoviral vector, a lentiviral vector, a retroviral vector, or an AAV vector. In specific embodiments of the method, the viral vector is a recombinant AAV vector.

In another aspect, the invention provides a method for producing a genetically-modified T cell comprising a modified human T cell receptor alpha gene. The method comprises: (a) introducing into a T cell: (i) a first nucleic acid sequence encoding an engineered nuclease, wherein the engineered nuclease is expressed in the T cell; or (ii) an engineered nuclease protein; and (b) introducing into the cell a second nucleic acid sequence comprising an exogenous sequence of interest; wherein the engineered nuclease produces a cleavage site at a recognition sequence within an intron in the human T cell receptor alpha gene that is positioned 5' upstream of TRAC exon 1; and wherein the sequence of interest is inserted into the human T cell receptor alpha gene at the cleavage site; and wherein the sequence of interest comprises an exogenous splice acceptor site and/or a poly A signal; and wherein the endogenous splice donor site and the endogenous splice acceptor site flanking the intron are unmodified and/or remain functional.

In some embodiments of the method, the T cell is a precursor T cell in which rearrangement of the V and J segments has not occurred.

In some embodiments of the method, cell surface expression of an endogenous T cell receptor is reduced when compared to an unmodified control cell.

In certain embodiments of the method, the intron comprises SEQ ID NO: 3.

In some embodiments of the method, the second nucleic acid sequence comprises from 5' to 3': (a) a 5' homology arm that is homologous to the 5' upstream sequence flanking the cleavage site; (b) the exogenous sequence of interest; and (c) a 3' homology arm that is homologous to the 3' downstream sequence flanking the cleavage site; wherein the exogenous sequence of interest is inserted into the human T cell receptor alpha gene at the cleavage site by homologous recombination.

In some embodiments of the method, the sequence of interest further comprises an exogenous branch site positioned 5' upstream of the exogenous splice acceptor site.

In certain embodiments of the method, the genetically-modified T cell is a genetically-modified human T cell, or a cell derived therefrom.

In some embodiments of the method, the exogenous sequence of interest comprises, from 5' to 3', an exogenous splice acceptor site, a 2A element or IRES element, a coding sequence for a protein of interest, and a polyA signal. In certain embodiments of the method, the 2A element is a T2A, a P2A, an E2A, or an F2A element. In particular embodiments of the method, the 2A element is a T2A element.

In some embodiments of the method, the sequence of interest comprises a coding sequence for a chimeric antigen receptor or an exogenous T cell receptor. In certain embodiments of the method, the chimeric antigen receptor or the exogenous T cell receptor comprises an extracellular ligand-binding domain having specificity for a tumor-specific antigen.

In some embodiments of the method, at least the first nucleic acid sequence is introduced into the T cell by an mRNA.

In certain embodiments of the method, at least the second nucleic acid sequence is introduced into the T cell by a viral vector. In particular embodiments of the method, the viral vector is an adenoviral vector, a lentiviral vector, a retroviral vector, or an adeno-associated viral (AAV) vector. In specific embodiments of the method, the viral vector is a recombinant AAV vector.

In some embodiments of the method, the engineered nuclease is an engineered meganuclease, a zinc-finger nuclease (ZFN), a transcription activator-like effector nuclease (TALEN), a compact TALEN, a CRISPR nuclease, or a megaTAL. In particular embodiments of the method, the engineered nuclease is an engineered meganuclease.

In some embodiments of the method, the engineered meganuclease has specificity for a recognition sequence comprising SEQ ID NO: 4. In some such embodiments of the method, the engineered meganuclease is an engineered meganuclease described herein which recognizes and cleaves SEQ ID NO: 4.

In some embodiments of the method, the engineered meganuclease has specificity for a recognition sequence comprising SEQ ID NO: 6. In some such embodiments of the method, the engineered meganuclease is an engineered meganuclease described herein which recognizes and cleaves SEQ ID NO: 6.

In some embodiments of the method, the engineered meganuclease has specificity for a recognition sequence comprising SEQ ID NO: 8. In some such embodiments of the method, the engineered meganuclease is an engineered meganuclease described herein which recognizes and cleaves SEQ ID NO: 8.

In some embodiments of the method, the engineered meganuclease has specificity for a recognition sequence comprising SEQ ID NO: 10. In some such embodiments of the method, the engineered meganuclease is an engineered meganuclease described herein which recognizes and cleaves SEQ ID NO: 10.

In another aspect, the invention provides a genetically-modified T cell prepared by any of the methods described herein for producing a genetically-modified T cell.

In another aspect, the invention provides a genetically-modified T cell comprising in its genome a modified human T cell receptor alpha gene, wherein the modified human T cell receptor alpha gene comprises an exogenous sequence of interest inserted into an intron within the T cell receptor alpha gene that is positioned 5' upstream of TRAC exon 1, and wherein the exogenous sequence of interest comprises an exogenous splice acceptor site and/or a poly A signal, and wherein the endogenous splice donor site and the endogenous splice acceptor site flanking the intron are unmodified and/or remain functional, and wherein cell surface expression of an endogenous T cell receptor is reduced when compared to an unmodified control cell.

In some embodiments, the intron comprises SEQ ID NO: 3.

In certain embodiments, the genetically-modified T cell is a genetically-modified human T cell, or a cell derived therefrom.

In some embodiments, the exogenous sequence of interest comprises, from 5' to 3', an exogenous splice acceptor site, a 2A element or IRES element, a coding sequence for a protein of interest, and a polyA signal. In particular embodiments, the 2A element is a T2A, a P2A, an E2A, or an F2A element. In specific embodiments, the 2A element is a T2A element.

In some embodiments, the exogenous sequence of interest further comprises an exogenous branch site positioned 5' upstream of the exogenous splice acceptor site.

In certain embodiments, the sequence of interest comprises a coding sequence for a chimeric antigen receptor or an exogenous T cell receptor. In particular embodiments, the chimeric antigen receptor or the exogenous T cell receptor comprises an extracellular ligand-binding domain having specificity for a tumor-specific antigen.

In some embodiments, the exogenous sequence of interest is inserted into the intron at an engineered meganuclease recognition site, a TALEN recognition site, a zinc finger nuclease recognition site, a CRISPR recognition site, or a megaTAL recognition site. In particular embodiments, the exogenous sequence of interest is inserted into the intron at an engineered meganuclease recognition site. In specific embodiments, the exogenous sequence of interest is inserted into the intron within SEQ ID NO: 4. In other embodiments, the exogenous sequence of interest is inserted into the intron within SEQ ID NO: 6. In further embodiments, the exogenous sequence of interest is inserted into the intron within SEQ ID NO: 8. In other embodiments, the exogenous sequence of interest is inserted into the intron within SEQ ID NO: 10.

In another aspect, the invention provides a population of genetically-modified T cells comprising a plurality of a genetically-modified T cell described herein.

In some embodiments, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified T cell as described herein.

In particular embodiments, the genetically-modified T cell is a genetically-modified human T cell, or cell derived therefrom.

In some embodiments, the exogenous sequence of interest present in the genetically-modified T cell comprises a coding sequence for a chimeric antigen receptor or an exogenous T cell receptor. In particular embodiments, the chimeric antigen receptor or the exogenous T cell receptor comprises an extracellular ligand-binding domain having specificity for a tumor-specific antigen.

In some embodiments, cell surface expression of an endogenous T cell receptor is reduced on the genetically-modified T cell when compared to an unmodified control cell.

In another aspect, the invention provides a pharmaceutical composition useful for the treatment of a disease in a subject in need thereof, wherein the pharmaceutical composition comprises a pharmaceutically-acceptable carrier and a therapeutically effective amount of a genetically-modified T cell as described herein.

In certain embodiments, the genetically-modified T cell is a genetically-modified human T cell, or a cell derived therefrom.

In some embodiments, the exogenous sequence of interest present in the genetically-modified T cell comprises a coding sequence for a chimeric antigen receptor or an exogenous T cell receptor. In certain particular embodiments, the chimeric antigen receptor or the exogenous T cell receptor comprises an extracellular ligand-binding domain having specificity for a tumor-specific antigen.

In some embodiments, cell surface expression of an endogenous T cell receptor is reduced on the genetically-modified T cell when compared to an unmodified control cell.

In another aspect, the invention provides a method of treating a disease in a subject in need thereof, the method comprising administering to the subject a genetically-modified T cell as described herein.

In some embodiments, the method comprises administering to the subject a pharmaceutical composition described herein.

In certain embodiments, the method is an immunotherapy for the treatment of cancer in a subject in need thereof. In some such embodiments, the genetically-modified T cell is a genetically-modified human T cell, or a cell derived therefrom, the exogenous sequence of interest present in the genetically-modified T cell comprises a coding sequence for a chimeric antigen receptor or an exogenous T cell receptor comprising an extracellular ligand-binding domain having specificity for a tumor-specific antigen, and cell surface expression of an endogenous T cell receptor is reduced on the genetically-modified T cell when compared to an unmodified control cell.

In some embodiments of the method, the cancer is selected from the group consisting of a cancer of carcinoma, lymphoma, sarcoma, blastomas, and leukemia.

In certain embodiments of the method, the cancer is selected from the group consisting of a cancer of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma.

In particular embodiments of the method, the cancer of B cell origin is selected from the group consisting of B lineage acute lymphoblastic leukemia, B cell chronic lymphocytic leukemia, B cell non-Hodgkin's lymphoma, and multiple myeloma.

In another aspect, the invention provides a genetically-modified cell, as described herein, for use as a medicament. The invention further provides the use of a genetically-modified cell, as described herein, in the manufacture of a medicament for treating a disease in a subject in need thereof. In one such aspect, the medicament is useful in the treatment of cancer.

In another aspect, the invention provides a genetically-modified cell, as described herein, for use in treatment of a disease, and preferably in the treatment of cancer.

BRIEF DESCRIPTION OF THE FIGURES

FIG. 2. TRC recognition sequences in the targeted 5' intron of the human T cell receptor alpha gene. Each recognition sequence targeted by an engineered meganuclease of the invention comprises two recognition half-sites. Each recognition half-site comprises 9 base pairs, separated by a 4 base pair central sequence. The TRC 11-12 recognition sequence (SEQ ID NO: 4) comprises two recognition half-sites referred to as TRC11 and TRC12. The TRC 15-16 recognition sequence (SEQ ID NO: 6) comprises two recognition half-sites referred to as TRC15 and TRC16. The TRC 17-18 recognition sequence (SEQ ID NO: 8) comprises two recognition half-sites referred to as TRC17 and TRC18. The TRC 19-20 recognition sequence (SEQ ID NO: 10) comprises two recognition half-sites referred to as TRC19 and TRC20.

FIG. 5. Efficiency of engineered meganucleases for recognizing and cleaving recognition sequences in the found in the targeted 5' intron of the T cell receptor alpha gene in a CHO cell reporter assay. Engineered meganucleases set forth in SEQ ID NOs: 12-15 were engineered to target the TRC 11-12 recognition sequence (SEQ ID NO: 4). Engineered meganucleases set forth in SEQ ID NOs: 16-19 were engineered to target the TRC 15-16 recognition sequence (SEQ ID NO: 6), and were screened for efficacy in the CHO cell reporter assay. Engineered meganucleases set forth in SEQ ID NOs: 20-23 were engineered to target the TRC 17-18 recognition sequence (SEQ ID NO: 8). Engineered meganucleases set forth in SEQ ID NOs: 24-27 were engineered to target the TRC 19-20 recognition sequence (SEQ ID NO: 10). The results shown provide the percentage of GFP-expressing cells observed in each assay, which indicates the efficacy of each meganuclease for cleaving a target recognition sequence or the CHO-23/24 recognition sequence. A negative control (bs) was further included in each assay.

FIG. 6. Efficiency of engineered meganucleases for recognizing and cleaving recognition sequences in the intron of the human T cell receptor alpha gene which is 5' upstream of TRAC exon 1 in a CHO cell reporter assay. Engineered meganucleases set forth in SEQ ID NOs: 12-15 were engineered to target the TRC 11-12 recognition sequence (SEQ ID NO: 4). Engineered meganucleases set forth in SEQ ID NOs: 16-19 were engineered to target the TRC 15-16 recognition sequence (SEQ ID NO: 6), and were screened for efficacy in the CHO cell reporter assay. Engineered meganucleases set forth in SEQ ID NOs: 20-23 were engineered to target the TRC 17-18 recognition sequence (SEQ ID NO: 8). Engineered meganucleases set forth in SEQ ID NOs: 24-27 were engineered to target TRC 19-20 recognition sequence (SEQ ID NO: 10). The engineered meganucleases were screened for efficacy in the CHO cell reporter assay at multiple time points over 7 days after nucleofection. The results shown provide the percentage of GFP-expressing cells observed in each assay over the 7 day period of analysis, which indicates the efficacy of each meganuclease for cleaving a target recognition sequence or the CHO-23/24 recognition sequence as a function of time.

FIG. 8. Cleavage at recognition sequences in the targeted 5' intron do not affect T cell receptor expression. Human T cells were enriched from an apheresis sample obtained from a human donor and were stimulated for 3 days using antiCD3/antiCD28 beads in the presence of IL-2. After 3 days, T cells were harvested, beads were removed, and 1 µg of the indicated meganuclease RNA was introduced to T cell samples. Nucleofected cells were cultured for 6 days prior to flow cytometric analysis. CD3 surface display, representative of endogenous T cell receptor expression, was measured by labeling T cell samples with anti-CD3-BrilliantViolet711 and GhostDye-510. T cells were nucleofected with either TRC 1-2x.87EE (an engineered nuclease which targets TRAC exon 1) or no RNA (mock) to serve as positive and negative controls for TRAC locus editing, respectively, and appear in FIG. 8A and FIG. 8B. Four additional samples were also nucleofected with RNA encoding one distinct nuclease variant from the TRC 15-16 family, all members of which target the TRC 15-16 recognition sequence in the 5' intron. When TRAC locus editing results in gene disruption, no TCRα chains are synthesized, and no TCR complex (including CD3) is displayed on the surface of edited cells. Greater than half of the TRC 1-2x.87EE edited T cells were shown to be TRC negative due to cleavage in exon 1 and error-prone repair of the cleavage cite by NHEJ (FIG. 8B).

By comparison, the frequency of TCR negative cells following editing by TRC 15-16x.31, TRC 15-16x.63, TRC 15-16x.87, and TRC 15-16x.89 was between only 4% and 8% (FIGS. 8C, 8D, 8E, and 8F, respectively).

Figure 9A:
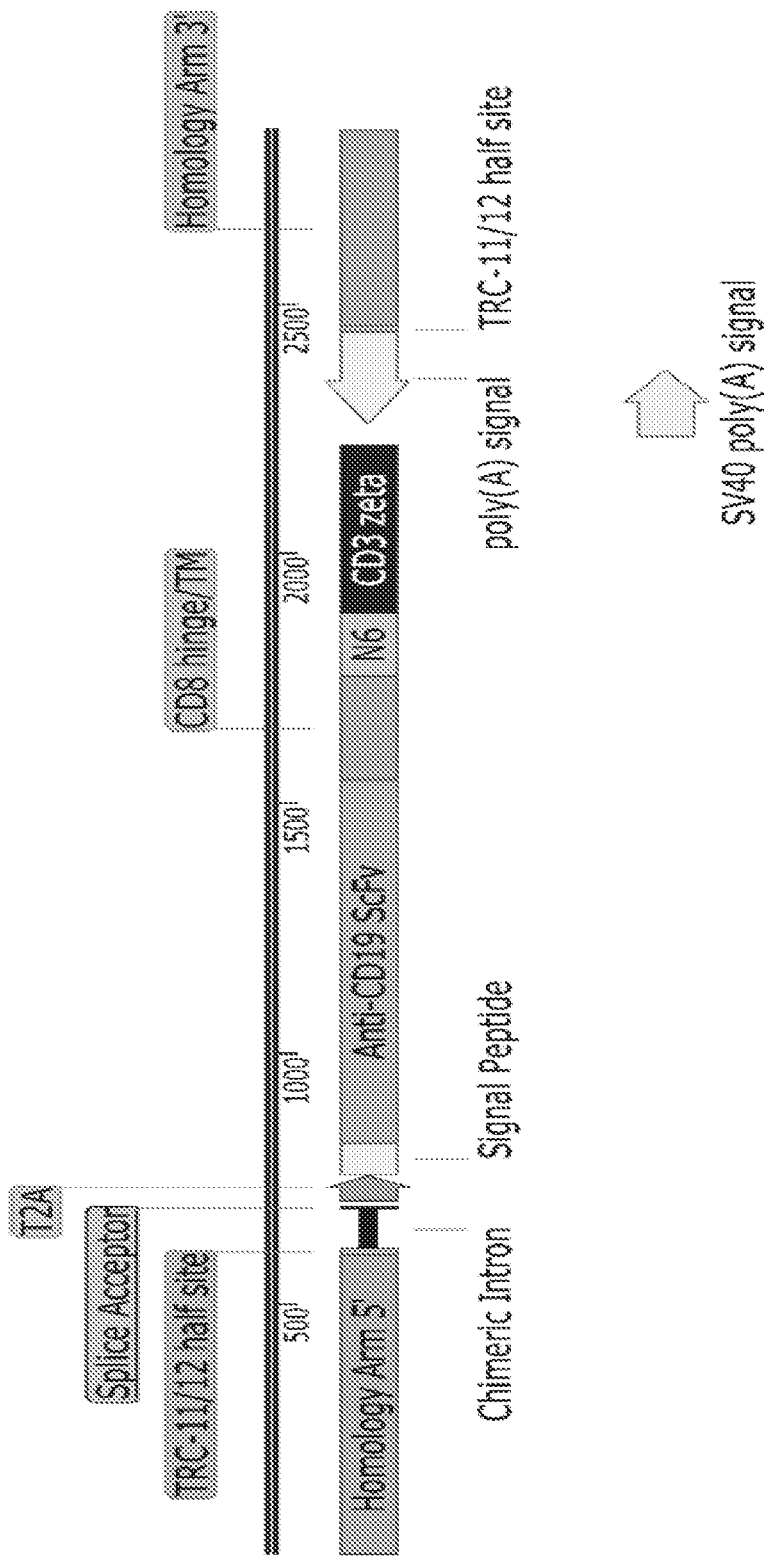
Figure 9B:
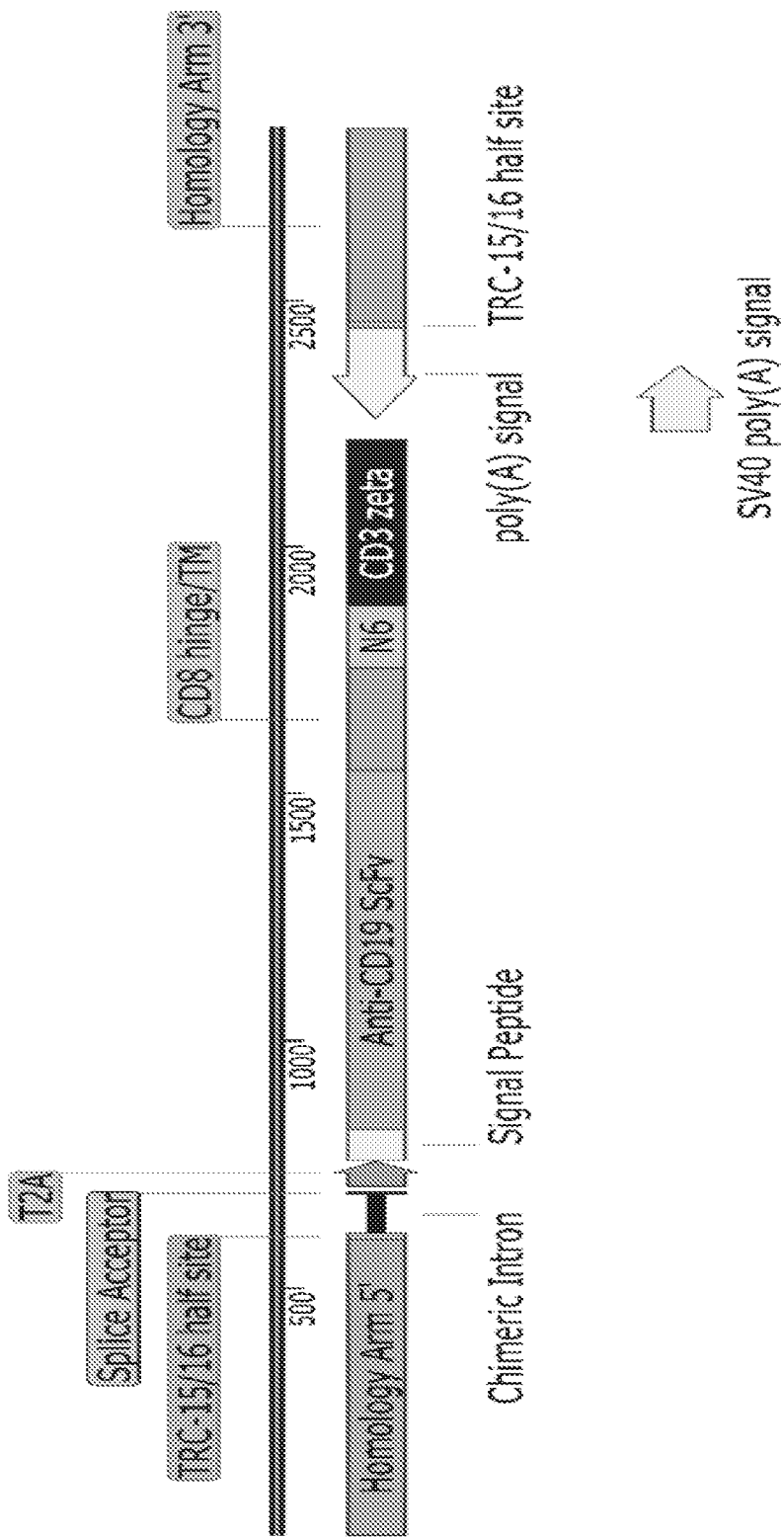
Figure 9C:
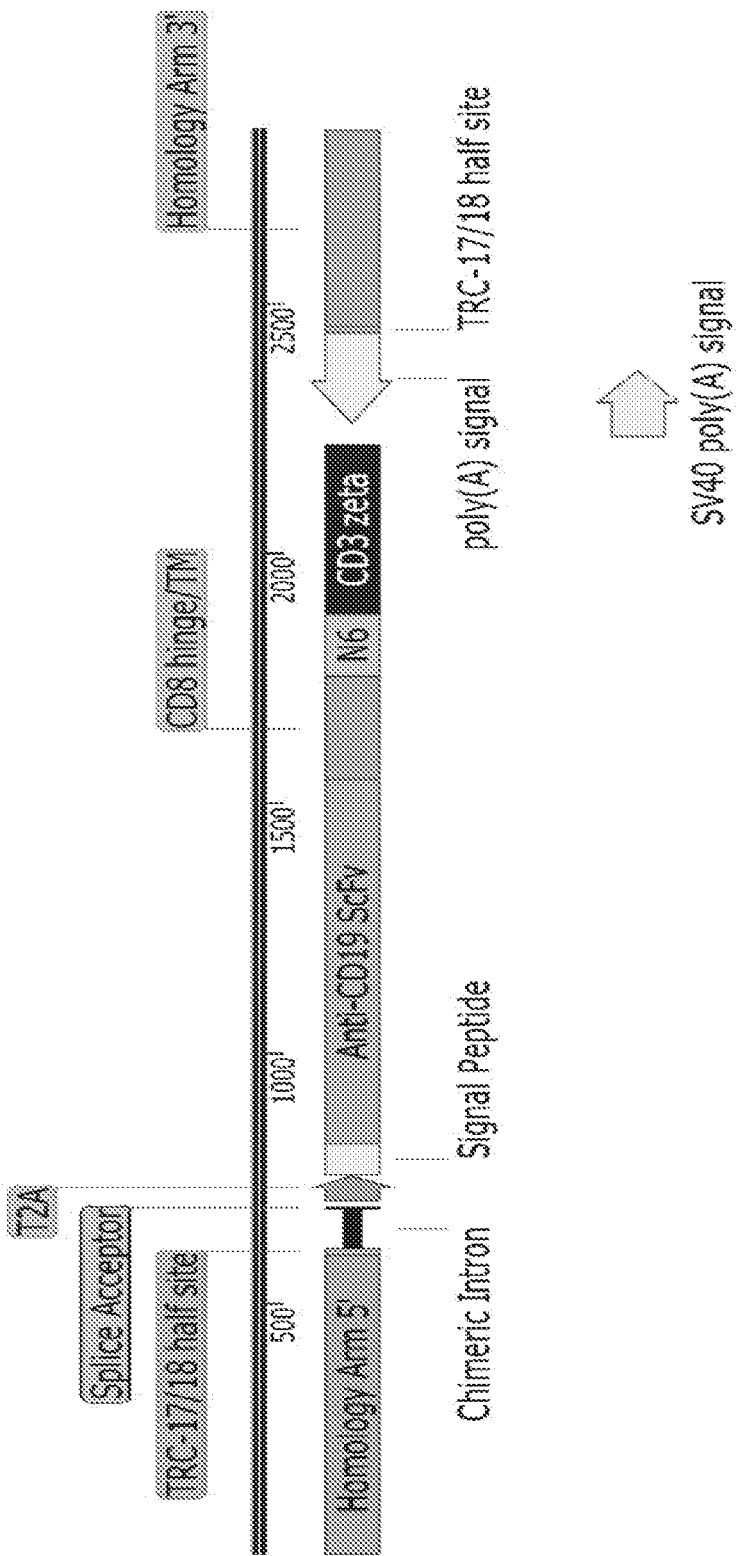

FIG. 9. Donor templates for exogenous sequence of interest. Donor templates comprising homology arms, an exogenous splice acceptor site, a CAR coding sequence, and a poly A signal, are provided. FIG. 9A provides an example donor template (SEQ ID NO: 60) suitable for insertion into the TRC 11-12 recognition sequence. FIG. 9B provides an example donor template (SEQ ID NO: 61) suitable for insertion into the TRC 15-16 recognition sequence. FIG. 9C provides an example donor template (SEQ ID NO: 62) suitable for insertion into the TRC 17-18 recognition sequence.

FIG. 10. Insertion of a GFP coding sequence into the targeted 5' intron. T cells were nucleofected with mRNA encoding the TRC 11-12x.82 nuclease and were transduced with an AAV6 vector comprising the 7227 construct, which encodes a T2A sequence followed by a promoterless GFP coding sequence. Additional T cells were nucleofected with mRNA encoding the TRC 15-16.x31 nuclease and were transduced with an AAV6 vector comprising the 7228 construct, which encodes a T2A sequence followed by a promoterless GFP coding sequence. TCR knockout and GFP expression were determined by flow cytometry 5 days after transfection/transduction. FIG. 10A shows CD3 (x-axis) and GFP (y-axis) expression following donor template insertion at the TRC 11-12 recognition sequence. FIG. 10B shows GFP expression (x-axis) and cell count (y-axis) following donor template insertion at the TRC 11-12 recognition sequence. FIG. 10C shows CD3 (x-axis) and GFP (y-axis) expression following donor template insertion at the TRC 15-16 recognition sequence. FIG. 10D shows GFP expression (x-axis) and cell count (y-axis) following donor template insertion at the TRC 15-16 recognition sequence.

Figure 11:
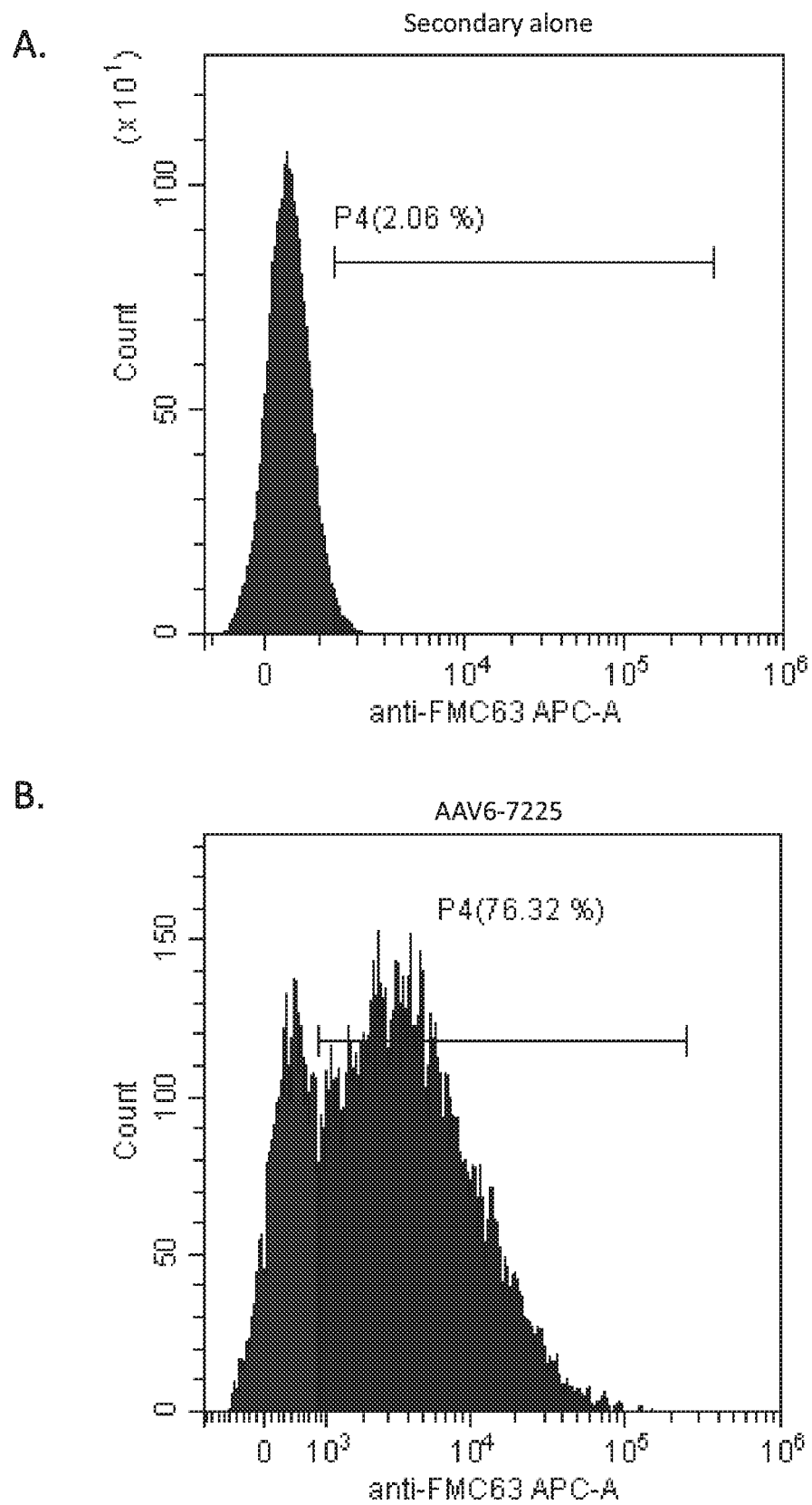
Figure 11:
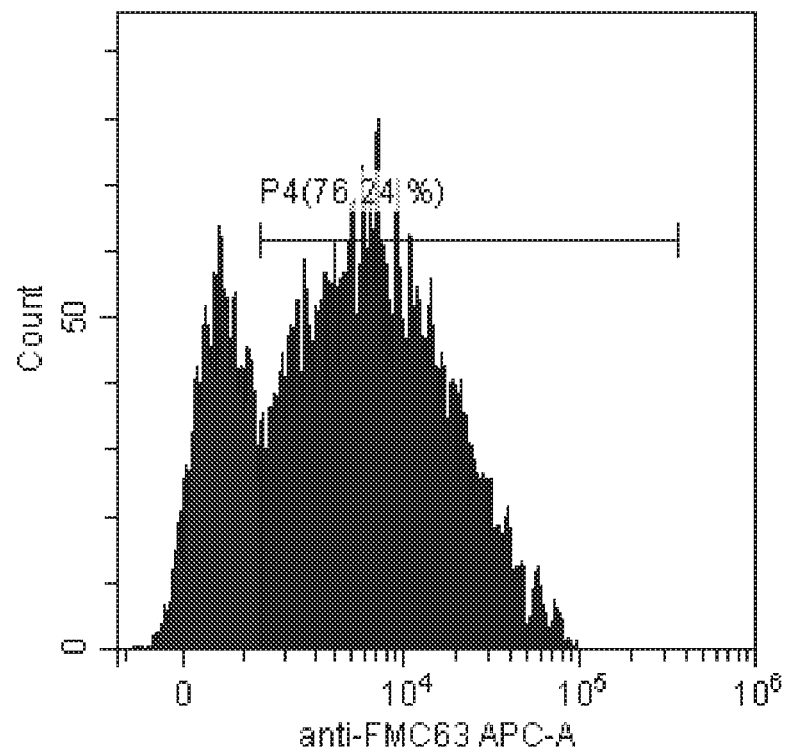

FIG. 11. Insertion of an anti-CD19 CAR coding sequence into the targeted 5' intron. T cells were nucleofected with mRNA encoding the TRC 11-12x.82 nuclease and were transduced with an AAV6 vector comprising the 7225 construct, which encodes a T2A sequence followed by a promoterless anti-CD19 CAR coding sequence. Additional T cells were nucleofected with mRNA encoding the TRC 15-16.x31 nuclease and were transduced with an AAV6 vector comprising the 7226 construct, which encodes a T2A sequence followed by a promoterless anti-CD19 CAR coding sequence. TCR knockout and CAR expression were determined by flow cytometry 5 days after transfection/transduction. FIG. 11A shows CAR expression on CD3– cells in a negative control group (TRC enzyme only). FIG. 11B shows CAR expression on CD3– cells following donor template insertion at the TRC 11-12 recognition sequence. FIG. 11C shows CAR expression on CD3– cells following donor template insertion at the TRC 15-16 recognition sequence.

BRIEF DESCRIPTION OF THE SEQUENCES

SEQ ID NO: 1 sets forth the amino acid sequence of wild-type I-CreI meganuclease.
SEQ ID NO: 2 sets forth the amino acid sequence of LAGLIDADG.
SEQ ID NO: 3 sets forth a nucleic acid sequence of the human T cell receptor alpha gene intron.
SEQ ID NO: 4 sets forth the nucleic acid sequence of TRC 11-12 (sense).
SEQ ID NO: 5 sets forth the nucleic acid sequence of TRC 11-12 (antisense).
SEQ ID NO: 6 sets forth the nucleic acid sequence of TRC 15-16 (sense).
SEQ ID NO: 7 sets forth the nucleic acid sequence of TRC 15-16 (antisense).
SEQ ID NO: 8 sets forth the nucleic acid sequence of TRC 17-18 (sense).
SEQ ID NO: 9 sets forth the nucleic acid sequence of TRC 17-18 (antisense).
SEQ ID NO: 10 sets forth the nucleic acid sequence of TRC 19-20 (sense).
SEQ ID NO: 11 sets forth the nucleic acid sequence of TRC 19-20 (antisense).
SEQ ID NO: 12 sets forth the amino acid sequence of the TRC 11-12x.4 meganuclease.
SEQ ID NO: 13 sets forth the amino acid sequence of the TRC 11-12x.82 meganuclease.
SEQ ID NO: 14 sets forth the amino acid sequence of the TRC 11-12x.60 meganuclease.
SEQ ID NO: 15 sets forth the amino acid sequence of the TRC 11-12x.63 meganuclease.
SEQ ID NO: 16 sets forth the amino acid sequence of the TRC 15-16x.31 meganuclease.
SEQ ID NO: 17 sets forth the amino acid sequence of the TRC 15-16x.87 meganuclease.
SEQ ID NO: 18 sets forth the amino acid sequence of the TRC 15-16x.63 meganuclease.
SEQ ID NO: 19 sets forth the amino acid sequence of the TRC 15-16x.89 meganuclease.
SEQ ID NO: 20 sets forth the amino acid sequence of the TRC17-18x.15 meganuclease.
SEQ ID NO: 21 sets forth the amino acid sequence of the TRC17-18x.82 meganuclease.
SEQ ID NO: 22 sets forth the amino acid sequence of the TRC17-18x.18 meganuclease.
SEQ ID NO: 23 sets forth the amino acid sequence of the TRC17-18x.71 meganuclease.
SEQ ID NO: 24 sets forth the amino acid sequence of the TRC 19-20x.85 meganuclease.
SEQ ID NO: 25 sets forth the amino acid sequence of the TRC 19-20x.74 meganuclease.
SEQ ID NO: 26 sets forth the amino acid sequence of the TRC 19-20x.71 meganuclease.
SEQ ID NO: 27 sets forth the amino acid sequence of the TRC 19-20x.87 meganuclease.
SEQ ID NO: 28 sets forth the amino acid sequence of the TRC 11-12x.4 meganuclease TRC11-binding subunit.
SEQ ID NO: 29 sets forth the amino acid sequence of the TRC 11-12x.82 meganuclease TRC11-binding subunit.
SEQ ID NO: 30 sets forth the amino acid sequence of the TRC 11-12x.60 meganuclease TRC11-binding subunit.
SEQ ID NO: 31 sets forth the amino acid sequence of the TRC 11-12x.63 meganuclease TRC11-binding subunit.
SEQ ID NO: 32 sets forth the amino acid sequence of the TRC 11-12x.4 meganuclease TRC12-binding subunit.
SEQ ID NO: 33 sets forth the amino acid sequence of the TRC 11-12x.82 meganuclease TRC12-binding subunit.
SEQ ID NO: 34 sets forth the amino acid sequence of the TRC 11-12x.60 meganuclease TRC12-binding subunit.
SEQ ID NO: 35 sets forth the amino acid sequence of the TRC 11-12x.63 meganuclease TRC12-binding subunit.
SEQ ID NO: 36 sets forth the amino acid sequence of the TRC 15-16x.31 meganuclease TRC15-binding subunit.
SEQ ID NO: 37 sets forth the amino acid sequence of the TRC 15-16x.87 meganuclease TRC15-binding subunit.

SEQ ID NO: 38 sets forth the amino acid sequence of the TRC 15-16x.63 meganuclease TRC15-binding subunit.

SEQ ID NO: 39 sets forth the amino acid sequence of the TRC 15-16x.89 meganuclease TRC15-binding subunit.

SEQ ID NO: 40 sets forth the amino acid sequence of the TRC 15-16x.31 meganuclease TRC16-binding subunit.

SEQ ID NO: 41 sets forth the amino acid sequence of the TRC 15-16x.87 meganuclease TRC16-binding subunit.

SEQ ID NO: 42 sets forth the amino acid sequence of the TRC 15-16x.63 meganuclease TRC16-binding subunit.

SEQ ID NO: 43 sets forth the amino acid sequence of the TRC 15-16x.89 meganuclease TRC16-binding subunit.

SEQ ID NO: 44 sets forth the amino acid sequence of the TRC17-18x.15 meganuclease TRC17-binding subunit.

SEQ ID NO: 45 sets forth the amino acid sequence of the TRC17-18x.82 meganuclease TRC17-binding subunit.

SEQ ID NO: 46 sets forth the amino acid sequence of the TRC17-18x.18 meganuclease TRC17-binding subunit.

SEQ ID NO: 47 sets forth the amino acid sequence of the TRC17-18x.71 meganuclease TRC17-binding subunit.

SEQ ID NO: 48 sets forth the amino acid sequence of the TRC17-18x.15 meganuclease TRC18-binding subunit.

SEQ ID NO: 49 sets forth the amino acid sequence of the TRC17-18x.82 meganuclease TRC18-binding subunit.

SEQ ID NO: 50 sets forth the amino acid sequence of the TRC17-18x.18 meganuclease TRC18-binding subunit.

SEQ ID NO: 51 sets forth the amino acid sequence of the TRC17-18x.71 meganuclease TRC18-binding subunit.

SEQ ID NO: 52 sets forth the amino acid sequence of the TRC 19-20x.85 meganuclease TRC19-binding subunit.

SEQ ID NO: 53 sets forth the amino acid sequence of the TRC 19-20x.74 meganuclease TRC19-binding subunit.

SEQ ID NO: 54 sets forth the amino acid sequence of the TRC 19-20x.71 meganuclease TRC19-binding subunit.

SEQ ID NO: 55 sets forth the amino acid sequence of the TRC 19-20x.87 meganuclease TRC19-binding subunit.

SEQ ID NO: 56 sets forth the amino acid sequence of the TRC 19-20x.85 meganuclease TRC20-binding subunit.

SEQ ID NO: 57 sets forth the amino acid sequence of the TRC 19-20x.74 meganuclease TRC20-binding subunit.

SEQ ID NO: 58 sets forth the amino acid sequence of the TRC 19-20x.71 meganuclease TRC20-binding subunit.

SEQ ID NO: 59 sets forth the amino acid sequence of the TRC 19-20x.87 meganuclease TRC20-binding subunit.

SEQ ID NO: 60 sets forth the nucleic acid sequence of a donor template comprising an anti-CD19 CAR that can be inserted at the TRC 11-12 recognition sequence.

SEQ ID NO: 61 sets forth the nucleic acid sequence of a donor template comprising an anti-CD19 CAR that can be inserted at the TRC 15-16 recognition sequence.

SEQ ID NO: 62 sets forth the nucleic acid sequence of a donor template comprising an anti-CD19 CAR that can be inserted at the TRC 17-18 recognition sequence.

SEQ ID NO: 63 sets forth the nucleic acid sequence of the 7227 donor template encoding a GFP protein that can be inserted at the TRC 11-12 recognition sequence.

SEQ ID NO: 64 sets forth the nucleic acid sequence of the 7225 donor template encoding an anti-CD19 CAR that can be inserted at the TRC 11-12 recognition sequence.

SEQ ID NO: 65 sets forth the nucleic acid sequence of the 7228 donor template encoding a GFP protein that can be inserted at the TRC 15-16 recognition sequence.

SEQ ID NO: 66 sets forth the nucleic acid sequence of the 7226 donor template encoding an anti-CD19 CAR that can be inserted at the TRC 15-16 recognition sequence.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859). A meganuclease as used herein binds to double-stranded DNA as a heterodimer or as a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251 and 9,434,931. In some embodiments, a linker may have an amino acid sequence comprising residues 154-195 of any one of SEQ ID NOs: 12-27.

As used herein, the term "zinc finger nuclease" or "ZFN" refers to chimeric proteins comprising a zinc finger DNA-binding domain fused to a nuclease domain from an endonuclease or exonuclease, including but not limited to a restriction endonuclease, homing endonuclease, 51 nuclease, mung bean nuclease, pancreatic DNAse I, micrococcal nuclease, and yeast HO endonuclease. Nuclease domains useful for the design of zinc finger nuclease include those from a Type IIs restriction endonuclease, including but not limited to FokI, FoM, StsI restriction enzyme. Additional Type IIs restriction endonucleases are described in International Publication No. WO 2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 basepairs in length. See, for example, U.S. Pat. Nos. 5,789,538, 5,925,523, 6,007,988, 6,013,453, 6,200,759, and International Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in U.S. Publications Nos. 20030232410, 20050208489, 2005064474, 20050026157, 20060188987 and International Publication No. WO 07/014275, each of which is incorporated by reference in its entirety.

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, S1 nuclease, mung bean nuclease, pancreatic DNAse I, micrococcal nuclease, and yeast HO endonuclease. See, for example, Christian et al. (2010) *Genetics* 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRI, BglI, and AlwI. Additional Type IIs restriction endonucleases are described in International Publication No. WO 2007/014275. In some embodiments, the nuclease domain of the TALEN is a FokI nuclease domain or an active portion thereof. TAL domain repeats can be derived from the TALE (transcription activator-like effector) family of proteins used in the infection process by plant pathogens of the *Xanthomonas* genus. TAL domain repeats are 33-34 amino acid sequences with divergent $12^{th}$ and $13^{th}$ amino acids. These two positions, referred to as the repeat variable dipeptide (RVD), are highly variable and show a strong correlation with specific nucleotide recognition. Each base pair in the DNA target sequence is contacted by a single TAL repeat, with the specificity resulting from the RVD. In some embodiments, the TALEN comprises 16-22 TAL domain repeats. DNA cleavage by a TALEN requires two DNA recognition regions flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally-occurring TALE protein or can be redesigned through rational or experimental means to produce a protein which binds to a pre-determined DNA sequence (see, for example, Boch et al. (2009) *Science* 326(5959): 1509-1512 and Moscou and Bogdanove (2009) *Science* 326(5959):1501, each of which is incorporated by reference in its entirety). See also, U.S. Publication No. 20110145940 and International Publication No. WO 2010/079430 for methods for engineering a TALEN to recognize a specific sequence and examples of RVDs and their corresponding target nucleotides. In some embodiments, each nuclease (e.g., FokI) monomer can be fused to a TAL effector sequence that recognizes a different DNA sequence, and only when the two recognition sites are in close proximity do the inactive monomers come together to create a functional enzyme.

As used herein, the term "Compact TALEN" refers to an endonuclease comprising a DNA-binding domain with 16-22 TAL domain repeats fused in any orientation to any portion of the I-TevI homing endonuclease or any of the endonucleases listed in Table 2 in U.S. Application No. 20130117869 (which is incorporated by reference in its entirety), including but not limited to MmeI, EndA, EndI, I-BasI, I-TevII, I-TevIII, I-TwoI, MspI, MvaI, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the term "CRISPR" refers to a Cas-based endonuclease comprising a Cas, such as Cas9, Cpf1, or another suitable nuclease, and a guide RNA that directs DNA cleavage of the Cas by hybridizing to a recognition site in the genomic DNA. The Cas component of a CRISPR is an RNA-guided DNA endonuclease. In certain embodiments, the Cas is a class II Cas enzyme. In some of these embodiments, the Cas is a class II, type II enzyme, such as Cas9. In other embodiments, the Cas is a class II, type V enzyme, such as Cpf1. The guide RNA comprises a direct repeat and a guide sequence (often referred to as a spacer in the context of an endogenous CRISPR system), which is complementary to the target recognition site. In certain embodiments, the CRISPR further comprises a tracrRNA (trans-activating CRISPR RNA) that is complementary (fully or partially) to a direct repeat sequence (sometimes referred to as a tracr-mate sequence) present on the guide RNA. In particular embodiments, the Cas can be mutated with respect to a corresponding wild-type enzyme such that the enzyme lacks the ability to cleave one strand of a target polynucleotide, functioning as a nickase, cleaving only a single strand of the target DNA. Non-limiting examples of Cas enzymes that function as a nickase include Cas9 enzymes with a D10A mutation within the RuvC I catalytic domain, or with a H840A, N854A, or N863A mutation.

As used herein, the term "megaTAL" refers to a single-chain nuclease comprising a transcription activator-like effector (TALE) DNA binding domain with an engineered, sequence-specific homing endonuclease.

As used herein, with respect to a protein, the terms "recombinant" or "engineered" means having an altered amino acid sequence as a result of the application of genetic engineering techniques to nucleic acids that encode the protein, and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant, engineered, or non-naturally-occurring nucleases.

As used herein with respect to recombinant or engineered proteins, the term "modification" means any insertion, deletion or substitution of an amino acid residue in the recombinant sequence relative to a reference sequence (e.g., a wild-type or a native sequence).

As used herein, the term "recognition sequence" refers to a DNA sequence that is bound and cleaved by an endonuclease. In the case of a meganuclease, a recognition sequence comprises a pair of inverted, 9 base pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four base pair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 base pair recognition sequence. In the case of a compact TALEN, the recognition sequence can comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a Compact TALEN produces two base pair 3' overhangs. In the case of a CRISPR, the recognition sequence is the sequence, typically 16-24 basepairs, to which the guide RNA binds to direct Cas9 cleavage. Full complementarity between the guide sequence and the recognition sequence is not necessarily required to effect cleavage. Cleavage by a CRISPR can produce blunt ends (such as by a class II, type II Cas) or overhanging ends (such as by a class II, type V Cas), depending on the Cas. In those embodiments wherein a Cpf1 Cas is utilized, cleavage by the CRISPR complex comprising the same will result in 5' overhangs and in certain embodiments, 5 nucleotide 5' overhangs. Each Cas enzyme also requires the recognition of a PAM (protospacer adjacent motif) sequence that is near the recognition sequence complementary to the guide RNA. The precise sequence, length requirements for the PAM, and distance from the target sequence differ depending on the Cas enzyme, but PAMs are typically 2-5 base pair sequences adjacent to the target/recognition sequence. PAM sequences for particular Cas enzymes are known in the art (see, for example, U.S. Pat. No. 8,697,359 and U.S. Publication No. 20160208243, each of which is incorporated by reference in its entirety) and PAM sequences for novel or engineered Cas enzymes can be identified using methods known in the art, such as a PAM depletion assay (see, for example, Karvelis et al. (2017) *Methods* 121-122:3-8, which is incorporated herein in its entirety). In the case of a zinc finger, the DNA binding domains typically recognize an 18-bp recognition sequence comprising a pair of nine basepair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a nuclease has "altered" binding affinity if the $K_d$ of the nuclease for a reference recognition sequence is increased or decreased by a statistically significant percent change relative to a reference nuclease.

As used herein, the term "homologous recombination" or "HR" refers to the natural, cellular process in which a double-stranded DNA-break is repaired using a homologous DNA sequence as the repair template (see, e.g., Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, a "chimeric antigen receptor" or "CAR" refers to an engineered receptor that confers or grafts specificity for an antigen onto an immune effector cell (e.g., a human T cell). A chimeric antigen receptor typically comprises at least an extracellular ligand-binding domain or moiety and an intracellular domain that comprises one or more signaling domains and/or co-stimulatory domains.

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some embodiments, the scFv is attached via a linker sequence. In various embodiments, the extracellular ligand-binding domain is specific for any antigen or epitope of interest. In some embodiments, the scFv is murine, humanized, or fully human.

The extracellular domain of a chimeric antigen receptor can also comprise an autoantigen (see, Payne et al. (2016), Science 353 (6295): 179-184), that can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

The extracellular domain of a chimeric antigen receptor can also comprise a naturally-occurring ligand for an antigen of interest, or a fragment of a naturally-occurring ligand which retains the ability to bind the antigen of interest.

The intracellular stimulatory domain can include one or more cytoplasmic signaling domains that transmit an activation signal to the immune effector cell following antigen binding. Such cytoplasmic signaling domains can include, without limitation, CD3ζ.

The intracellular stimulatory domain can also include one or more intracellular co-stimulatory domains that transmit a proliferative and/or cell-survival signal after ligand binding. As used herein, a "co-stimulatory domain" refers to a polypeptide domain which transmits an intracellular proliferative and/or cell-survival signal upon activation. Activation of a co-stimulatory domain may occur following homodimerization of two co-stimulatory domain polypeptides. Activation may also occur, for example, following activation of a construct comprising the co-stimulatory domain (e.g., a chimeric antigen receptor or an inducible regulatory construct). Generally, a co-stimulatory domain can be derived from a transmembrane co-stimulatory receptor, particularly from an intracellular portion of a co-stimulatory receptor. Such intracellular co-stimulatory domains can be any of those known in the art and can include, without limitation, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, N1, N6, or any combination thereof.

A chimeric antigen receptor can further include additional structural elements, including a transmembrane domain that is attached to the extracellular ligand-binding domain via a hinge or spacer sequence. The transmembrane domain can be derived from any membrane-bound or transmembrane protein. For example, the transmembrane polypeptide can be a subunit of the T-cell receptor (i.e., an α, β, γ or ζ, polypeptide constituting CD3 complex), IL2 receptor p55 (a chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRIIIa receptor or IgG1.

As used herein, an "exogenous T cell receptor" or "exogenous TCR" refers to a TCR whose sequence is introduced into the genome of an immune effector cell (e.g., a human T cell) that may or may not endogenously express the TCR. Expression of an exogenous TCR on an immune effector cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, the term "reduced expression" refers to any reduction in the expression of the endogenous T cell receptor at the cell surface of a genetically-modified T cell when compared to a control cell. The term reduced can also refer to a reduction in the percentage of cells in a population of cells that express an endogenous polypeptide (i.e., an endogenous T cell receptor) at the cell surface when compared to a population of control cells. Such a reduction may be up to 5%, 10%, 20%, 30%, 40%, 50%, 60%, 70%, 80%, 90%, 95%, 96%, 97%, 98%, 99%, or up to 100%. Accordingly, the term "reduced" encompasses both a partial knockdown and a complete knockdown of the endogenous T cell receptor.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and that is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272;

Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule that is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 12-27. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 12-27. In other embodiments, variable residues within a hypervariable region correspond to one or more of positions 215, 217, 219, 221, 223, 224, 229, 231, 233, 235, 237, 259, 261, 266, and 268 of any one of SEQ ID NOs: 12-27.

As used herein, the terms "T cell receptor alpha gene" or "TCR alpha gene" are interchangeable and refer to the locus in a T cell which encodes the T cell receptor alpha subunit. The T cell receptor alpha can refer to NCBI gene ID number 6955, before or after rearrangement. Following rearrangement, the T cell receptor alpha gene comprises an endogenous promoter, rearranged V and J segments, the endogenous splice donor site, an intron, the endogenous splice acceptor site, and the TRAC locus, which comprises the subunit coding exons. For example, see FIG. 1.

Figure 1:
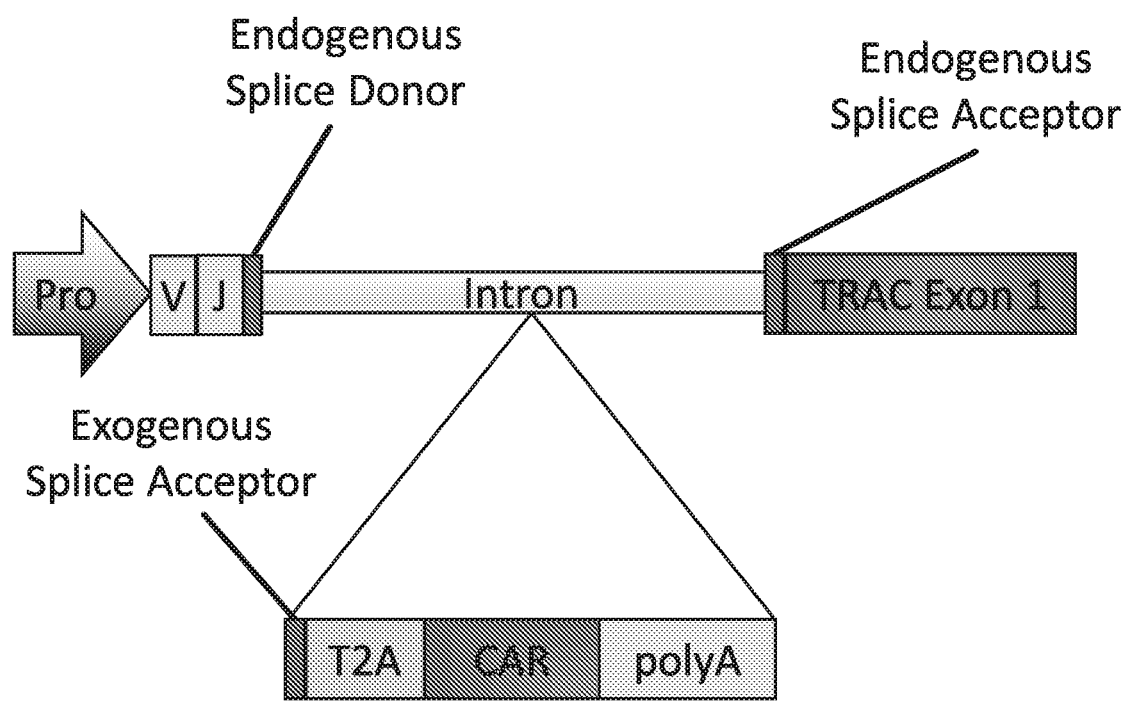
FIG. 1. Diagram of sample strategy for insertion and expression of an exogenous sequence of interest into an intron of a T cell receptor alpha gene, which has been rearranged to encode a functional T cell receptor alpha subunit. As shown, an exogenous sequence of interest is inserted into the intron of the T cell receptor alpha gene that is 5' upstream of TRAC exon 1. The endogenous splice acceptor site and the endogenous splice acceptor site which flank the targeted 5' intron remain intact. Following cleavage by a nuclease, an exogenous sequence of interest described herein is inserted into the intron. As shown, the sequence of interest comprises at least an exogenous splice acceptor site and/or a poly A signal which, when inserted into the intron, will disrupt expression of the T cell receptor alpha subunit. The inserted sequence of interest can optionally include a 2A element, which is represented by a T2A element. The inserted sequence of interest can also optionally include a coding sequence for a polypeptide of interest, which is represented by a chimeric antigen receptor coding sequence. If necessary, the sequence of interest can further comprise an exogenous branch site positioned 5' upstream of the exogenous splice acceptor site.
Figure 3:
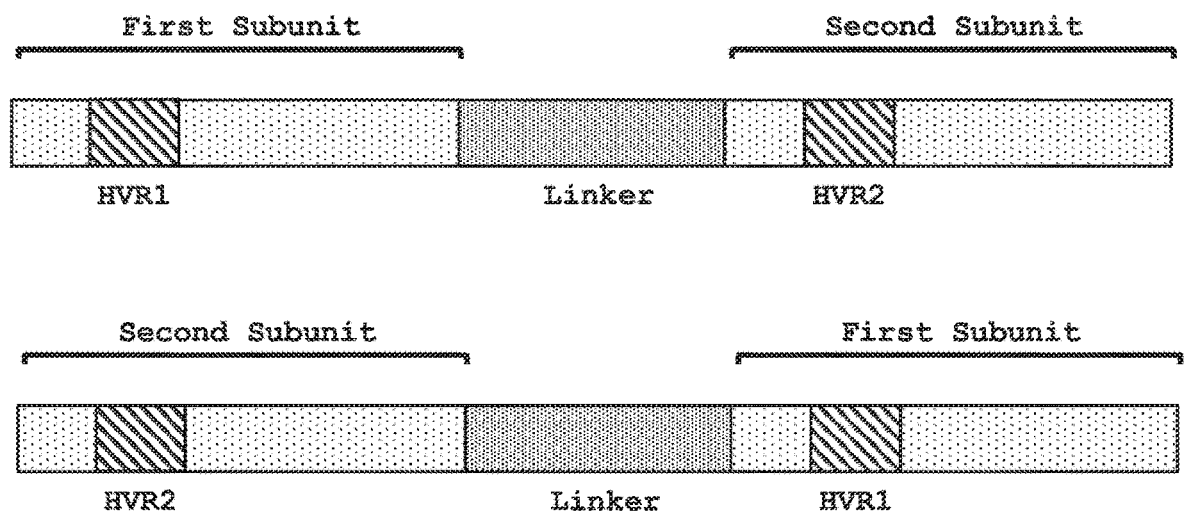
FIG. 3. The engineered meganucleases of the invention comprise two subunits, wherein the first subunit comprising the HVR1 region binds to a first recognition half-site (e.g., TRC11, TRC15, TRC17, or TRC19) and the second subunit comprising the HVR2 region binds to a second recognition half-site (e.g., TRC12, TRC16, TRC18, or TRC20). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

As used herein, the phrases "intron within the T cell receptor alpha gene" and "the targeted 5' intron" refer to the intron, as shown in FIG. 1, which in the rearranged T cell receptor alpha gene is positioned 5' upstream of TRAC exon 1, 3' downstream of the V and J segments, and is flanked by the endogenous splice donor site and the endogenous splice acceptor site. The targeted 5' intron can have a sequence comprising SEQ ID NO: 3, and functional variants thereof which retain the nuclease recognition sequences encompassed by the invention.

As used herein, the terms "T cell receptor alpha constant region" and "TRAC" are used interchangeably and refer to the coding sequence of the T cell receptor alpha gene. The TRAC includes the wild-type sequence, and functional variants thereof, identified by NCBI Gen ID NO. 28755.

As used herein, the term "endogenous splice donor site" refers to the naturally-occurring splice donor site positioned 3' downstream of the endogenous TCR alpha gene promoter and the rearranged V and J segments, and 5' upstream of the targeted intron. Likewise, the "endogenous splice acceptor site" refers to the naturally-occurring splice acceptor site that is 3' downstream of the targeted intron and immediately 5' upstream of TRAC exon 1. Endogenous splice donor sites and endogenous splice acceptor sites can be identified in a gene by methods known in the art, such as those described by Desmet et al. (Nucleic Acid Research (2009) 37(9): e67). The term "functional" as it relates to the endogenous splice donor site and the endogenous splice acceptor site refers to their ability to pair in order to execute splicing of the intervening intron sequence.

As used herein, the term "exogenous splice acceptor site" refers to a splice acceptor site which is comprised by the exogenous sequence of interest and is introduced into the targeted 5' intron. The exogenous splice acceptor site can comprise a sequence naturally present in the human T cell receptor alpha gene, or can comprise a splice acceptor sequence (e.g., a consensus or heterologous sequence) which is not naturally present in the gene. The exogenous splice acceptor site may further comprise an exogenous branch site if necessary to promote splicing of the intron. Such a branch site may comprise a sequence which is naturally present in the T cell receptor alpha gene, or can comprise a branch site sequence (e.g., a consensus or heterologous sequence) which is not naturally present in the gene.

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of single or double-stranded polynucleotides, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "human T cell" or "T cell" refers to a T cell isolated from a donor, particularly a human donor. T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "human natural killer cell" or "human NK cell" or "natural killer cell" or "NK cell" refers to a type of cytotoxic lymphocyte critical to the innate immune system. The role NK cells play is analogous to that of cytotoxic T-cells in the vertebrate adaptive immune response. NK cells provide rapid responses to virally infected cells and respond to tumor formation, acting at around 3 days after infection.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration that resulted in the genetically-modified cell; (b) a cell of the same genotype as the genetically-modified cell but that has been transformed with a null construct (i.e., with a construct that has no known effect on the trait of interest); or, (c) a cell genetically identical to the genetically-modified cell but that is not exposed to conditions or stimuli or further genetic modifications that would induce expression of altered genotype or phenotype.

As used herein, the terms "treatment" or "treating a subject" refers to the administration of a genetically-modified T cell of the invention to a subject having a disease. For example, the subject can have a disease such as cancer, and treatment can represent immunotherapy for the treatment of the disease. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some aspects, a genetically-modified cell described herein is administered during treatment in the form of a pharmaceutical composition of the invention.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated.

As used herein, the term "cancer" should be understood to encompass any neoplastic disease (whether invasive or metastatic) which is characterized by abnormal and uncontrolled cell division causing malignant growth or tumor.

As used herein, the term "carcinoma" refers to a malignant growth made up of epithelial cells.

As used herein, the term "leukemia" refers to malignancies of the hematopoietic organs/systems and is generally characterized by an abnormal proliferation and development of leukocytes and their precursors in the blood and bone marrow.

As used herein, the term "sarcoma" refers to a tumor which is made up of a substance like the embryonic connective tissue and is generally composed of closely packed cells embedded in a fibrillary, heterogeneous, or homogeneous substance.

As used herein, the term "melanoma" refers to a tumor arising from the melanocytic system of the skin and other organs.

As used herein, the term "lymphoma" refers to a group of blood cell tumors that develop from lymphocytes.

As used herein, the term "blastoma" refers to a type of cancer that is caused by malignancies in precursor cells or blasts (immature or embryonic tissue).

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable that is described as having values between 0 and 2 can take the values 0, 1, or 2 if the variable is inherently discrete, and can take the values 0.0, 0.1, 0.01, 0.001, or any other real values 0 and 2 if the variable is inherently continuous.

2.1 Principle of the Invention

The present invention is based, in part, on the discovery that insertion of a sequence of interest (including an exogenous splice acceptor site and/or a poly A signal) into a nuclease cleavage site in the targeted 5' intron of the T cell receptor alpha gene allows for the production of TCR– cells only when the insert is present. If no insert is present, the nuclease-modified intron is simply removed and the endogenous gene is expressed. Thus, in an example where the sequence of interest includes a CAR coding sequence, the present invention provides a method for producing a population where most or all TCR– cells are TCR–/CAR+ cells. Any other peptide of interest can be expressed from the sequence of interest in the same manner as a CAR.

By contrast, conventional nuclease-based approaches for generating modified T cells target coding sequences of the TRAC and/or the endogenous splice acceptor site 5' upstream of TRAC exon 1. Consequently, they can generate highly mixed populations of TCR− cells, which include a substantial percentage of TCR−/CAR− cells, due to NHEJ at the nuclease cleavage site which creates indels and disrupts protein expression.

Thus, by reducing the need to purify a mixed population of TCR− cells, the present invention provides a simplified method for producing a population of allogeneic CAR T cells that express an antigen-specific CAR and have reduced expression of the endogenous TCR. Such cells can exhibit reduced or no induction of graft-versus-host-disease (GVHD) when administered to an allogeneic subject. Furthermore, the inclusion of a 2A element in the exogenous sequence of interest allows for expression of a coding sequence to be driven by the endogenous T cell receptor alpha gene promoter, rather than by an exogenous promoter. In this manner, expression of a polypeptide such as a CAR can be regulated by the T cell feedback mechanisms normally associated with TCR expression.

2.2 Nucleases for Recognizing and Cleaving Recognition Sequences within the Targeted 5' Intron of the T Cell Receptor Alpha Gene It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. The use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode, for example, a chimeric antigen receptor, an exogenous TCR, or any sequence or polypeptide of interest.

In different embodiments, a variety of different types of nucleases are useful for practicing the invention. In one embodiment, the invention can be practiced using engineered meganucleases. In another embodiment, the invention can be practiced using a CRISPR nuclease or CRISPR Nickase. Methods for making CRISPRs and CRISPR Nickases that recognize pre-determined DNA sites are known in the art, for example Ran, et al. (2013) *Nat Protoc.* 8:2281-308. In another embodiment, the invention can be practiced using TALENs or Compact TALENs. Methods for making TALE domains that bind to pre-determined DNA sites are known in the art, for example Reyon et al. (2012) *Nat Biotechnol.* 30:460-5. In another embodiment, the invention can be practiced using zinc finger nucleases (ZFNs). In a further embodiment, the invention can be practiced using megaTALs.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, engineered meganucleases of the invention have been engineered to recognize and cleave the TRC 11-12 recognition sequence (SEQ ID NO: 4). Such engineered meganucleases are collectively referred to herein as "TRC 11-12 meganucleases." Exemplary TRC 11-12 meganucleases are provided in SEQ ID NOs: 12-15.

In additional examples, engineered meganucleases of the invention have been engineered to recognize and cleave the TRC 15-16 recognition sequence (SEQ ID NO: 6). Such engineered meganucleases are collectively referred to herein as "TRC 15-16 meganucleases." Exemplary TRC 15-16 meganucleases are provided in SEQ ID NOs: 16-19.

In additional examples, engineered meganucleases of the invention have been engineered to recognize and cleave the TRC 17-18 recognition sequence (SEQ ID NO: 8). Such engineered meganucleases are collectively referred to herein as "TRC 17-18 meganucleases." Exemplary TRC 17-18 meganucleases are provided in SEQ ID NOs: 20-23.

In further examples, engineered meganucleases of the invention have been engineered to recognize and cleave the TRC 19-20 recognition sequence (SEQ ID NO: 10). Such engineered meganucleases are collectively referred to herein as "TRC 19-20 meganucleases." Exemplary TRC 19-20 meganucleases are provided in SEQ ID NOs: 24-27.

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the TRC11, TRC15, TRC17, or TRC19 half-site), and the second subunit binds to a second recognition half-site in the recognition sequence (e.g., the TRC12, TRC16, TRC18, or TRC20 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary TRC 11-12 meganucleases of the invention are provided in Table 1. Exemplary TRC 15-16 meganucleases of the invention are provided in Table 2. Exemplary TRC 17-18 meganucleases of the invention are provided in Table 3. Exemplary TRC 19-20 meganucleases of the invention are provided in Table 4.

TABLE 1

Exemplary engineered meganucleases engineered to recognize and cleave the TRC 1-2 recognition sequence (SEQ ID NO: 4)

| Meganuclease | AA SEQ ID | TRC11 Subunit Residues | TRC11 Subunit SEQ ID | *TRC11 Subunit % | TRC12 Subunit Residues | TRC12 Subunit SEQ ID | *TRC12 Subunit % |
|---|---|---|---|---|---|---|---|
| TRC 11-12x.4  | 12 | 198-344 | 28 | 100   | 7-153 | 32 | 100   |
| TRC 11-12x.82 | 13 | 198-344 | 29 | 92.52 | 7-153 | 33 | 93.2  |
| TRC 11-12x.60 | 14 | 198-344 | 30 | 89.8  | 7-153 | 34 | 99.32 |
| TRC 11-12x.63 | 15 | 198-344 | 31 | 91.84 | 7-153 | 35 | 95.24 |

*"TRC11 Subunit %" and "TRC12 Subunit %" represent the amino acid sequence identity between the TRC11-binding and TRC12-binding subunit regions of each meganuclease and the TRC11-binding and TRC12-binding subunit regions, respectively, of the TRC 11-12x.4 meganuclease.

TABLE 2

Exemplary engineered meganucleases engineered to recognize and cleave the TRC 15-16 recognition sequence (SEQ ID NO: 6)

| Meganuclease | AA SEQ ID | TRC15 Subunit Residues | TRC15 Subunit SEQ ID | *TRC15 Subunit % | TRC16 Subunit Residues | TRC16 Subunit SEQ ID | *TRC16 Subunit % |
|---|---|---|---|---|---|---|---|
| TRC 15-16x.31 | 16 | 7-153 | 36 | 100   | 198-344 | 40 | 100   |
| TRC 15-16x.87 | 17 | 7-153 | 37 | 100   | 198-344 | 41 | 92.52 |
| TRC 15-16x.63 | 18 | 7-153 | 38 | 98.64 | 198-344 | 42 | 92.52 |
| TRC 15-16x.89 | 19 | 7-153 | 39 | 99.32 | 198-344 | 43 | 99.32 |

*"TRC15 Subunit %" and "TRC16 Subunit %" represent the amino acid sequence identity between the TRC15-binding and TRC16-binding subunit regions of each meganuclease and the TRC15-binding and TRC16-binding subunit regions, respectively, of the TRC 15-16x.31 meganuclease.

TABLE 3

Exemplary engineered meganucleases engineered to recognize and cleave the TRC 17-18 recognition sequence (SEQ ID NO: 8)

| Meganuclease | AA SEQ ID | TRC17 Subunit Residues | TRC17 Subunit SEQ ID | *TRC17 Subunit % | TRC18 Subunit Residues | TRC18 Subunit SEQ ID | *TRC18 Subunit % |
|---|---|---|---|---|---|---|---|
| TRC 17-18x.15 | 20 | 7-153 | 44 | 100   | 198-344 | 48 | 100   |
| TRC 17-18x.82 | 21 | 7-153 | 45 | 90.48 | 198-344 | 49 | 89.8  |
| TRC17-18x.18  | 22 | 7-153 | 46 | 91.16 | 198-344 | 50 | 95.24 |
| TRC17-18x.71  | 23 | 7-153 | 47 | 91.16 | 198-344 | 51 | 94.56 |

*"TRC17 Subunit %" and "TRC18 Subunit %" represent the amino acid sequence identity between the TRC17-binding and TRC18-binding subunit regions of each meganuclease and the TRC17-binding and TRC18-binding subunit regions, respectively, of the TRC17-18x.15 meganuclease.

TABLE 4

Exemplary engineered meganucleases engineered to recognize and cleave the TRC 19-20 recognition sequence (SEQ ID NO: 10)

| Meganuclease | AA SEQ ID | TRC19 Subunit Residues | TRC19 Subunit SEQ ID | *TRC19 Subunit % | TRC20 Subunit Residues | TRC20 Subunit SEQ ID | *TRC20 Subunit % |
|---|---|---|---|---|---|---|---|
| TRC 19-20x.85 | 24 | 7-153 | 52 | 100   | 198-344 | 56 | 100   |
| TRC 19-20x.74 | 25 | 7-153 | 53 | 94.56 | 198-344 | 57 | 94.56 |
| TRC 19-20x.71 | 26 | 7-153 | 54 | 93.88 | 198-344 | 58 | 89.8  |
| TRC 19-20x.87 | 27 | 7-153 | 55 | 100   | 198-344 | 59 | 92.52 |

*"TRC19 Subunit %" and "TRC20 Subunit %" represent the amino acid sequence identity between the TRC19-binding and TRC20-binding subunit regions of each meganuclease and the TRC19-binding and TRC20-binding subunit regions, respectively, of the TRC 19-20x.85 meganuclease.

2.3 Methods for Producing Genetically-Modified Cells

Following rearrangement, the human T cell receptor alpha gene comprises a number of elements. Generally, without being bound by any specific theory, these elements include from 5' to 3', an endogenous promoter, rearranged V and J segments, an endogenous splice donor site, an intron (i.e., the targeted 5' intron), an endogenous splice acceptor site, and the TRAC locus, which comprises the alpha subunit coding exons and interspaced introns. For example, see FIG. 1.

The invention disclosed herein provides methods for producing genetically-modified T cells comprising a modified TCR alpha gene. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art may be used. In some embodiments of the present disclosure, T cells are obtained from a unit of blood collected from a subject using any number of techniques known to the skilled artisan. In one embodiment, cells from the circulating blood of an individual are obtained by apheresis.

The modified T cell receptor alpha gene comprises an exogenous sequence of interest inserted into the intron within the TCR alpha gene that is positioned 5' upstream of TRAC exon 1 (i.e., the targeted 5' intron). More specifically, the exogenous sequence of interest can be inserted 3' downstream of the rearranged V and J segments and the endogenous splice donor site, and 5' upstream of the endogenous splice acceptor site. In specific embodiments, the targeted 5' intron comprises the sequence set forth in SEQ ID NO: 3, or a sequence having at least 75%, 80%, 85%, 90%, 95%, 96%, 97%, 98%, or 99% sequence identity to the nucleic acid sequence set forth in SEQ ID NO: 3 and comprising a recognition sequence of an engineered nuclease as described herein.

In some embodiments, the exogenous sequence of interest can be inserted into the intron at a double-stranded cleavage site generated by an engineered nuclease, such as an engineered meganuclease, a zinc finger nuclease, a TALEN, a compact TALEN, a CRISPR nuclease, or a megaTAL. Cleavage sites generated by such nucleases can allow for homologous recombination of the exogenous sequence of interest directly into the 5' intron.

The "endogenous splice donor site" refers to the naturally-occurring splice donor site that is 3' downstream of the endogenous TCR alpha gene promoter and the rearranged V and J segments, and 5' upstream of the targeted intron. Likewise, the "endogenous splice acceptor site" refers to the naturally-occurring splice acceptor site that is 3' downstream of the targeted intron and immediately 5' upstream of TRAC exon 1. See, FIG. 1.

In specific embodiments, the engineered nucleases disclosed herein do not modify either the endogenous splice donor site or the endogenous splice acceptor site, as both sites should retain their functionality to practice the invention. In some embodiments, the endogenous splice donor site and/or the endogenous splice acceptor site can be modified as long as each site retains the ability to pair with the other and splice the intron (i.e., retains functionality). Thus, as used herein, a functional endogenous splice donor site has the ability to pair with the endogenous splice acceptor site to remove the intron. Likewise, as used herein, a functional endogenous splice acceptor site has the ability to pair with the endogenous splice donor site to remove the intron.

In particular embodiments, the sequence of interest can comprise an exogenous splice acceptor site. As used herein, the term "exogenous" or "heterologous" in reference to a nucleotide sequence is intended to mean a sequence that is purely synthetic, that originates from a foreign species, or, if from the same species, is substantially modified from its native form in composition and/or genomic locus by deliberate human intervention. Thus, the exogenous splice acceptor site can be a purely synthetic splice acceptor site, or a splice acceptor site from the human genome that has been modified in sequence or genomic locus.

In specific embodiments, the exogenous splice acceptor site is able to partner with the endogenous splice donor site in order to splice out the intervening intron sequence. In this manner, the exogenous splice acceptor site can disrupt natural splicing of the targeted 5' intron by competing with the endogenous splice acceptor site for partnering with the endogenous splice donor site.

In various embodiments, the exogenous sequence of interest can comprise a coding sequence for a protein of interest. It is envisioned that the coding sequence can be for any protein of interest.

In certain embodiments, the exogenous sequence of interest comprises a nucleic acid sequence encoding a CAR. Generally, a CAR of the present disclosure will comprise at least an extracellular domain and an intracellular domain. In some embodiments, the extracellular domain comprises a target-specific binding element otherwise referred to as a ligand-binding domain or moiety. In some embodiments, the intracellular domain, or cytoplasmic domain, comprises at least one co-stimulatory domain and one or more signaling domains such as, for example, CD3ζ. In other embodiments, the CAR may only comprise a signaling domain, such as CD3ζ, and the cell may comprise one or more co-stimulatory domains on another construct expressed in the cell.

In some embodiments, a CAR useful in the invention comprises an extracellular, target-specific binding element otherwise referred to as a ligand-binding domain or moiety. The choice of ligand-binding domain depends upon the type and number of ligands that define the surface of a target cell. For example, the ligand-binding domain may be chosen to recognize a ligand that acts as a cell surface marker on target cells associated with a particular disease state. Thus, examples of cell surface markers that may act as ligands for the ligand-binding domain in a CAR can include those associated with viruses, bacterial and parasitic infections, autoimmune disease, and cancer cells. In some embodiments, a CAR is engineered to target a tumor-specific antigen of interest by way of engineering a desired ligand-binding moiety that specifically binds to an antigen on a tumor cell. In the context of the present disclosure, "tumor antigen" refers to antigens that are common to specific hyperproliferative disorders such as cancer.

In some embodiments, the extracellular ligand-binding domain of the CAR is specific for any antigen or epitope of interest, particularly any tumor antigen or epitope of interest. As non-limiting examples, in some embodiments the antigen of the target is a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD22, CD30, CD40, CLL1, disialoganglioside GD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, insulin growth factor (IGF1)-1, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD38, CD123, CD133, CD138, CTLA-4, B7-1 (CD80), B7-2 (CD86), endoglin, a major histocompatibility complex (MHC) molecule, BCMA (CD269, TNFRSF 17), CS1, or a virus-specific surface antigen such as an HIV-specific antigen (such as HIV gp120); an EBV-specific antigen, a CMV-specific antigen, a HPV-specific antigen such as the E6 or E7 oncoproteins, a Lasse Virus-specific antigen, an Influenza Virus-specific antigen, as well as any derivate or variant of these surface markers. In a particular embodiment of the present disclosure, the ligand-binding domain is specific for CD19.

In some embodiments, the extracellular domain of a chimeric antigen receptor further comprises an autoantigen (see, Payne et al. (2016) Science, Vol. 353 (6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs).

In some embodiments, the extracellular domain of a chimeric antigen receptor can comprise a naturally-occurring ligand for an antigen of interest, or a fragment of a naturally-occurring ligand which retains the ability to bind the antigen of interest.

In some embodiments, a CAR comprises a transmembrane domain which links the extracellular ligand-binding domain or autoantigen with the intracellular signaling and co-stimulatory domains via a hinge or spacer sequence. The transmembrane domain can be derived from any membrane-bound or transmembrane protein. For example, the transmembrane polypeptide can be a subunit of the T-cell receptor (i.e., an α, β, γ or ζ, polypeptide constituting CD3 complex), IL2 receptor p55 (α chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine. In particular examples, the transmembrane domain is a CD8a transmembrane polypeptide.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRIIIa receptor or IgG1.

Intracellular signaling domains of a CAR of are responsible for activation of at least one of the normal effector functions of the cell in which the CAR has been placed and/or activation of proliferative and cell survival pathways. The term "effector function" refers to a specialized function of a cell. Effector function of a T cell, for example, may be cytolytic activity or helper activity including the secretion of cytokines. An intracellular signaling domain, such as CD3ζ, can provide an activation signal to the cell in response to binding of the extracellular domain. As discussed, the activation signal can induce an effector function of the cell such as, for example, cytolytic activity or cytokine secretion.

The intracellular domain of the CAR can include one or more intracellular co-stimulatory domains which transmit a co-stimulatory signal to promote cell proliferation, cell survival, and/or cytokine secretion after binding of the extracellular domain. Such intracellular co-stimulatory domains include those known in the art such as, without limitation, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, N1, or N6.

The CAR can be specific for any type of cancer cell. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In certain embodiments, cancers of B cell origin include, without limitation, B lineage acute lymphoblastic leukemia, B cell chronic lymphocytic leukemia, B cell non-Hodgkin's lymphoma, and multiple myeloma.

The sequence of interest can further encode an exogenous T cell receptor (TCR). Such exogenous T cell receptors can comprise alpha and beta chains or, alternatively, may comprise gamma and delta chains. Exogenous TCRs useful in the invention may have specificity to any antigen or epitope of interest.

In other embodiments, the sequence of interest can encode the wild-type or modified version of an endogenous gene of interest.

The sequence of interest can comprise an element or peptide known in the art to allow for the translation of two more genes from the same mRNA molecule, including but not limited to IRES elements and 2A elements, such as, a T2A element, a P2A element, an E2A element, and an F2A element. In specific embodiments, such elements in the exogenous sequence of interest can be located 5' upstream of a nucleic acid sequence encoding a protein of interest (e.g. a CAR).

The exogenous sequence of interest described herein can further comprise additional control sequences. For example, the sequences of interest can include homologous recombination enhancer sequences, Kozak sequences, polyadenylation sequences, transcriptional termination sequences, selectable marker sequences (e.g., antibiotic resistance genes), origins of replication, and the like. Sequences of interest described herein can also include at least one nuclear localization signal. Examples of nuclear localization signals are known in the art (see, e.g., Lange et al., *J. Biol. Chem.*, 2007, 282:5101-5105).

In specific embodiments, the exogenous sequence of interest comprises a polyadenylation sequence or poly A signal. Thus, a sequence of interest can comprise a poly A signal located 3' downstream of a sequence encoding a protein of interest (e.g. a CAR). In this manner, transcription of the T cell receptor alpha gene, particularly the coding sequences of the TRAC locus, will be disrupted by the poly A signal, thus preventing expression of the T cell receptor alpha subunit.

In some examples of the invention, the exogenous sequence of interest includes, from 5' to 3', an exogenous splice acceptor site, a 2A element or IRES element, a coding sequence for a protein of interest, and a polyA signal. In certain examples, the exogenous sequence of interest includes, from 5' to 3', an exogenous splice acceptor site, a 2A element or IRES element, a coding sequence for a CAR or an exogenous T cell receptor, and a polyA signal. In some examples, the exogenous sequence of interest can further include an exogenous branch site positioned 5' upstream of the exogenous splice acceptor site. In the various examples of the invention, the 2A element can be, without limitation, a T2A, a P2A, an E2A, or an F2A element.

Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA (e.g., mRNA). For embodiments in which the engineered nuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290(5804):304-10) as well as inducible promoters such as the tetracycline-inducible promoter (Dingermann et al. (1992), *Mol Cell Biol.* 12(9):4038-45).

In some embodiments, mRNA encoding the engineered nuclease is delivered to the cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methylguanosine. In some embodiments, the mRNA may be polyadenylated.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (i.e., cistrons) from the same mRNA molecule including, but not limited to, an IRES element, a T2A element, a P2A element, an E2A element, and an F2A element.

Purified nuclease proteins can be delivered into cells to cleave genomic DNA, which allows for homologous recombination or non-homologous end-joining at the cleavage site with a sequence of interest, by a variety of different mechanisms known in the art.

In some embodiments, engineered nuclease proteins, or DNA/mRNA encoding engineered nucleases, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, engineered nucleases, or DNA/mRNA encoding engineered nucleases, are coupled covalently or non-covalently to an antibody that recognizes a specific cell surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell surface receptor. (McCall, et al. (2014) Tissue Barriers. 2(4): e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, engineered nuclease proteins, or DNA/mRNA encoding engineered nucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 µm, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each engineered nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell surface receptors and the natural ligands (or portions of the natural ligands) for cell surface receptors.

In some embodiments, the engineered nucleases or DNA/mRNA encoding the engineered nucleases, are encapsulated within liposomes or complexed using cationic lipids (see, e.g., Lipofectamine, Life Technologies Corp., Carlsbad, Calif.; Zuris et al. (2015) Nat Biotechnol. 33: 73-80; Mishra et al. (2011) J Drug Deliv. 2011:863734). The liposome and lipoplex formulations can protect the payload from degradation, and facilitate cellular uptake and delivery efficiency through fusion with and/or disruption of the cellular membranes of the cells.

In some embodiments, engineered nuclease proteins, or DNA/mRNA encoding engineered nucleases, are encapsulated within polymeric scaffolds (e.g., PLGA) or complexed using cationic polymers (e.g., PEI, PLL) (Tamboli et al. (2011) Ther Deliv. 2(4): 523-536).

In some embodiments, engineered nuclease proteins, or DNA/mRNA encoding engineered nucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, engineered nuclease proteins, or DNA/mRNA encoding engineered nucleases, are formulated into an emulsion or a nanoemulsion (i.e., having an average particle diameter of <1 nm) for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, engineered nuclease proteins, or DNA/mRNA encoding engineered nucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high payload capacity. Moreover, display of multiple surface groups can be leveraged to improve stability and reduce nonspecific interactions.

In some embodiments, genes encoding an engineered nuclease and/or sequences of interest are introduced into a cell using a viral vector. Such vectors are known in the art and include retroviral vectors, lentiviral vectors, adenoviral vectors, and adeno-associated virus (AAV) vectors (reviewed in Vannucci, et al. (2013 New Microbiol. 36:1-22). Recombinant AAV vectors useful in the invention can have any serotype that allows for transduction of the virus into the cell and insertion of the nuclease gene into the cell genome. In particular embodiments, recombinant AAV vectors have a serotype of AAV2 or AAV6. Recombinant AAV vectors can also be self-complementary such that they do not require second-strand DNA synthesis in the host cell (McCarty, et al. (2001) Gene Ther. 8:1248-54).

If the engineered nuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, nuclease genes are operably linked to a promoter that drives gene expression preferentially in the target cell (e.g., a T cell).

The invention further provides for the introduction of an exogenous sequence of interest into the T cell receptor alpha gene, particularly into a recognition sequence within the targeted 5' intron. In some embodiments, the exogenous sequence of interest comprises a 5' homology arm and a 3' homology arm flanking the elements of the insert (i.e., the exogenous splice acceptor site, the IRES or 2A element, the coding sequence for a protein of interest, and/or the poly A signal). Such homology arms have sequence homology to corresponding sequences 5' upstream and 3' downstream of the nuclease recognition sequence in the targeted 5' intron where a cleavage site is produced. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

The exogenous sequence of interest of the invention may be introduced into the cell by any of the means previously discussed. In a particular embodiment, the exogenous sequence of interest is introduced by way of a viral vector, such as a lentivirus, retrovirus, adenovirus, or preferably a recombinant AAV vector. Recombinant AAV vectors useful for introducing an exogenous nucleic acid can have any serotype that allows for transduction of the virus into the cell and insertion of the exogenous nucleic acid sequence into the cell genome. In particular embodiments, the recombinant AAV vectors have a serotype of AAV2 or AAV6. The recombinant AAV vectors can also be self-complementary such that they do not require second-strand DNA synthesis in the host cell.

In another particular embodiment, the exogenous sequence of interest can be introduced into the cell using a single-stranded DNA template. The single-stranded DNA can comprise the exogenous sequence of interest and, in preferred embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding an engineered nuclease of the invention and/or an exogenous sequence of interest of the invention can be introduced into the cell by transfection with a linearized DNA template. In some examples, a plasmid DNA can be digested by one or more restriction enzymes such that the circular plasmid DNA is linearized prior to transfection into the cell.

T cells modified by the present invention may require activation prior to introduction of a nuclease and/or an exogenous sequence of interest. For example, T cells can be contacted with anti-CD3 and anti-CD28 antibodies that are soluble or conjugated to a support (i.e., beads) for a period of time sufficient to activate the cells.

Genetically-modified cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic pro-drug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode Cas-9, Cas-8, or cytosine deaminase. In some examples, Cas-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEnd10-binding epitope. For such a gene, Rituximab can be administered to a subject to induce cell depletion when needed. In further examples, a suicide gene may include a QBEnd10-binding epitope expressed in combination with a truncated EGFR polypeptide.

T cells modified by the methods and compositions described herein can have reduced expression of an endogenous T cell receptor and, optionally, can further express a protein of interest (e.g., a CAR). Thus, the invention further provides a population of T cells that express the protein of interest and do not express the endogenous T cell receptor. For example, the population can include a plurality of genetically-modified T cells of the invention which express a CAR (i.e., are CAR+), or an exogenous T cell receptor (i.e., exoTCR+), and have reduced expression of an endogenous T cell receptor (i.e., are TCR−). In various embodiments of the invention, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified T cell as described herein. In a particular example, the population can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, cells that are both TCR− and CAR+.

2.4 Pharmaceutical Compositions

In some embodiments, the invention provides a pharmaceutical composition comprising a genetically-modified T cell of the invention, or a population of genetically-modified T cells of the invention, and a pharmaceutically-acceptable carrier. Such pharmaceutical compositions can be prepared in accordance with known techniques. See, e.g., Remington, *The Science And Practice of Pharmacy* ($21^{st}$ ed. 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, pharmaceutical compositions of the invention can further include biological molecules, such as cytokines (e.g., IL-2, IL-7, IL-15, and/or IL-21), which promote in vivo cell proliferation and engraftment of genetically-modified T cells. Pharmaceutical compositions comprising genetically-modified T cells of the invention can be administered in the same composition as an additional agent or biological molecule or, alternatively, can be co-administered in separate compositions.

The present disclosure also provides genetically-modified cells, or populations thereof, described herein for use as a medicament. The present disclosure further provides the use of genetically-modified cells or populations thereof described herein in the manufacture of a medicament for treating a disease in a subject in need thereof. In one such aspect, the medicament is useful for cancer immunotherapy in subjects in need thereof.

Pharmaceutical compositions of the invention can be useful for treating any disease state that can be targeted by T cell adoptive immunotherapy. Non-limiting examples of cancer which may be treated with the pharmaceutical compositions and medicaments of the present disclosure are carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin's lymphoma.

In some of these embodiments wherein cancer is treated with the presently disclosed genetically-modified cells, the subject administered the genetically-modified cells is further administered an additional therapeutic, such as radiation, surgery, or a chemotherapeutic agent.

The invention further provides a population of genetically-modified cells comprising a plurality of genetically-modified cells described herein, which comprise in their genome an exogenous nucleic acid molecule encoding a sequence of interest, wherein the exogenous nucleic acid molecule is inserted into the targeted 5' intron of the T cell receptor alpha gene, and wherein cell-surface expression of the endogenous TCR is reduced. Thus, in various embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell described herein. In further embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell described herein which further express a chimeric antigen receptor.

2.5 Methods of Administering Genetically-Modified Cells

Another aspect disclosed herein is the administration of the genetically-modified T cells of the present disclosure to a subject in need thereof. In particular embodiments, the pharmaceutical compositions described herein are administered to a subject in need thereof. For example, an effective amount of a population of cells can be administered to a subject having a disease. In particular embodiments, the disease can be cancer, and administration of the genetically-modified T cells of the invention represent an immunotherapy. The administered cells are able to reduce the proliferation, reduce the number, or kill target cells in the recipient. Unlike antibody therapies, genetically-modified T cells of the present disclosure are able to replicate and expand in vivo, resulting in long-term persistence that can lead to sustained control of a disease.

Examples of possible routes of administration include parenteral, (e.g., intravenous (IV), intramuscular (IM), intradermal, subcutaneous (SC), or infusion) administration. Moreover, the administration may be by continuous infusion or by single or multiple boluses. In specific embodiments, one or both of the agents is infused over a period of less than about 12 hours, 6 hours, 4 hours, 3 hours, 2 hours, or 1 hour. In still other embodiments, the infusion occurs slowly at first and then is increased over time.

In some embodiments, a genetically-modified T cell of the present disclosure targets a tumor antigen for the purposes of treating cancer. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma. In specific embodiments, cancers and disorders include but are not limited to pre-B ALL (pediatric indication), adult ALL, mantle cell lymphoma, diffuse large B cell lymphoma, salvage post allogenic bone marrow transplantation, and the like. These cancers can be treated using a combination of CARs that target, for example, CD19, CD20, CD22, and/or ROR1. In some non-limiting examples, a genetically-modified eukaryotic cell or population thereof of the present disclosure targets carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin's lymphoma.

When an "effective amount" or "therapeutic amount" is indicated, the precise amount to be administered can be determined by a physician with consideration of individual differences in age, weight, tumor size (if present), extent of infection or metastasis, and condition of the patient (subject). In some embodiments, a pharmaceutical composition comprising the genetically-modified cells described herein is administered at a dosage of $10^4$ to $10^9$ cells/kg body weight, including all integer values within those ranges. In further embodiments, the dosage is $10^5$ to $10^6$ cells/kg body weight, including all integer values within those ranges. In some embodiments, cell compositions are administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In some embodiments, administration of genetically-modified T cells of the present disclosure reduce at least one symptom of a target disease or condition. For example, administration of genetically-modified T cells of the present disclosure can reduce at least one symptom of a cancer. Symptoms of cancers are well known in the art and can be determined by known techniques.

2.6 Methods for Producing Recombinant Viral Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene (s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific endonuclease is not expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

1. The endonuclease can be placed under the control of a tissue-specific promoter that is not active in the packaging cells. For example, if a viral vector is developed for delivery of (an) endonuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human a1-antitrypsin (such as PalAT), and hemopexin (such as Phpx) (Kramer, M G et al., (2003) Mol. Therapy 7:375-85). Examples of eye-specific promoters include opsin, and corneal epithelium-specific K12 promoters (Martin K R G, Klein R L, and Quigley H A (2002) Methods (28): 267-75) (Tong Y, et al., (2007) J Gene Med, 9:956-66). These promoters, or other tissue-specific promoters known in the art, are not highly-active in HEK-293 cells and, thus, will not expected to yield significant levels of endonuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) PLoS One v. 5(8):e12274).

2. Alternatively, the vector can be packaged in cells from a different species in which the endonuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) J. Biotechnol. 131(2):138-43). An endonuclease under the control of a mammalian promoter is unlikely to be expressed in these cells (Airenne, K J, et al. (2013) Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of an endonuclease. Because these introns are not spliced efficiently from pre-mRNA transcripts in insect cells, insect cells will not express a functional endonuclease and will package the full-length genome. In contrast, mammalian cells to which the resulting recombinant AAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

3. The endonuclease gene can be operably linked to an inducible promoter such that a small-molecule inducer is required for endonuclease expression. Examples of inducible promoters include the Tet-On system (Clontech; Chen H., et al., (2015) BMC Biotechnol. 15(1):4)) and the RheoSwitch system (Intrexon; Sowa G., et al., (2011) Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome The latter step is necessary because the endonuclease will not be expressed in the target cells or tissues following recombinant AAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) Gene 183:137-42). The use of a non-human transcription repressor ensures that transcription of the endonuclease gene will be repressed only in the packaging cells expressing the repressor and not in target cells or tissues transduced with the resulting recombinant AAV vector.

In some embodiments, genetic transfer is accomplished via lentiviral vectors. Lentiviruses, in contrast to other retroviruses, in some contexts may be used for transducing certain non-dividing cells. Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In specific embodiments, lentiviral vectors are prepared using a plasmid encoding the gag, pol, tat, and rev genes cloned from human immunodeficiency virus (HIV) and a second plasmid encoding the envelope protein from vesicular stomatitis virus (VSV-G) used to pseudotype viral particles. A transfer vector, such as the pCDH-EF1-MCS vector, can be used with a suitable promoter, if needed, and a coding sequence. All three plasmids can then be transfected into lentivirus cells, such as the Lenti-X-293T cells, and lentivirus can then be harvested, concentrated and screened after a suitable incubation time. Accordingly, methods are provided herein for producing recombinant lentiviral vectors comprising the exogenous sequence of interest described herein or an engineered nuclease of the invention.

2.7 Engineered Nuclease Variants

Embodiments of the invention encompass the engineered nucleases, and particularly the engineered meganucleases, described herein, and variants thereof. Further embodiments of the invention encompass isolated polynucleotides comprising a nucleic acid sequence encoding the engineered meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave recognition sequences found in the targeted 5' intron of the human T cell receptor alpha gene, including, for example, the TRC 11-12 recognition sequence (SEQ ID NO: 4), the TRC 15-16 recognition sequence (SEQ ID NO: 6), the TRC 17-18 recognition sequence (SEQ ID NO: 8), and the TRC 19-20 recognition sequence (SEQ ID NO: 10). Such variants may result, for example, from human manipulation. Biologically active variants of a native polypeptide of the embodiments (e.g., SEQ ID NOs: 12-27), or biologically active variants of the recognition half-site binding subunits described herein (e.g., SEQ ID NOs: 28-59), will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 5 provides potential substitutions that can be made in a recombinant meganuclease monomer or subunit to enhance specificity based on the base present at each half-site position (−1 through −9) of a recognition half-site.

of the genetic code, encode the amino acid sequence of one of the polypeptides of the embodiments. Variant polynucleotides include synthetically derived polynucleotides, such as those generated, for example, by using site-directed mutagenesis but which still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference poly-

TABLE 5

Favored Sense-Strand Base

| Posn. | A | C | G | T | A/T | A/C | A/G | C/T | G/T | A/G/T | A/C/G/T |
|---|---|---|---|---|---|---|---|---|---|---|---|
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | K28* | C28* | | | | M66 |
| | | | | | | | Q42 | | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | C38 | | | | | H38 |
| | Q38 | K30* | R38 | L38 | | | | | | | N38 |
| | | R30* | E30* | | | | | | | | Q30* |
| −8 | F33 | E33 | F33 | L33 | R32* | R33 | | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | | S32 |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein.
An asterisk indicates that the residue contacts the base on the antisense strand.

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy nucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide.

However, when it is difficult to predict the exact effect of the substitution, deletion, or insertion in advance of doing so, one skilled in the art will appreciate that the effect will be evaluated by screening the polypeptide for its ability to preferentially recognize and cleave recognition sequences found within the targeted 5' intron of the human T cell receptor alpha gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Recognize and Cleave Recognition Sequences in the Targeted 5' Intron of the T Cell Receptor Alpha Gene

1. Meganucleases that Recognize and Cleave the TRC 11-12 Recognition Sequence Engineered meganucleases (SEQ ID NOs: 12-15), collectively referred to herein as "TRC 11-12 meganucleases," were engineered to recognize and cleave the TRC 11-12 recognition sequence (SEQ ID NO: 4), which is present in the targeted 5' intron of the human T cell receptor alpha gene. Each TRC 11-12 recombinant meganuclease comprises an N-terminal nuclear-localization signal derived from SV40, a first meganuclease subunit, a linker sequence, and a second meganuclease subunit. A first subunit in each TRC 11-12 meganuclease binds to the TRC12 recognition half-site of SEQ ID NO: 4, while a second subunit binds to the TRC11 recognition half-site (see, FIG. 2).

The TRC12-binding subunits and TRC11-binding subunits each comprise a 56 base pair hypervariable region, referred to as HVR1 and HVR2, respectively. TRC12-binding subunits are highly conserved outside of the HVR1 region. Similarly, TRC11-binding subunits are also highly conserved outside of the HVR2 region. The TRC11-binding regions of SEQ ID NOs: 12-15 are provided as SEQ ID NOs: 28-31, respectively. Each of SEQ ID NOs: 28-31 share at least 90% sequence identity to SEQ ID NO: 28, which is the TRC11-binding region of the meganuclease TRC 11-12x.4 (SEQ ID NO: 12). TRC12-binding regions of SEQ ID NOs: 12-15 are provided as SEQ ID NOs: 32-35, respectively. Each of SEQ ID NOs: 32-35 share at least 90% sequence identity to SEQ ID NO: 32, which is the TRC12-binding region of the meganuclease TRC 11-12x.4 (SEQ ID NO: 12).

2. Meganucleases that Recognize and Cleave the TRC 15-16 Recognition Sequence Engineered meganucleases (SEQ ID NOs: 16-19), collectively referred to herein as "TRC 15-16 meganucleases," were engineered to recognize and cleave the TRC 15-16 recognition sequence (SEQ ID NO: 6), which is present in the targeted 5' intron of the human T cell receptor alpha gene. Each TRC 15-16 recombinant meganuclease comprises an N-terminal nuclear-localization signal derived from SV40, a first meganuclease subunit, a linker sequence, and a second meganuclease subunit. A first subunit in each TRC 15-16 meganuclease binds to the TRC15 recognition half-site of SEQ ID NO: 6, while a second subunit binds to the TRC16 recognition half-site (see, FIG. 2).

The TRC15-binding subunits and TRC16-binding subunits each comprise a 56 base pair hypervariable region, referred to as HVR1 and HVR2, respectively. TRC15-binding subunits are highly conserved outside of the HVR1 region. Similarly, TRC16-binding subunits are also highly conserved outside of the HVR2 region. The TRC15-binding regions of SEQ ID NOs: 16-19 are provided as SEQ ID NOs: 36-39, respectively. Each of SEQ ID NOs: 36-39 share at least 90% sequence identity to SEQ ID NO: 36, which is the TRC15-binding region of the meganuclease TRC 15-16x.31 (SEQ ID NO: 16). TRC16-binding regions of SEQ ID NOs: 16-19 are provided as SEQ ID NOs: 40-43, respectively. Each of SEQ ID NOs: 40-43 share at least 90% sequence identity to SEQ ID NO: 40, which is the TRC16-binding region of the meganuclease TRC 15-16x.31 (SEQ ID NO: 16).

3. Meganucleases that Recognize and Cleave the TRC 17-18 Recognition Sequence Engineered meganucleases (SEQ ID NOs: 20-23), collectively referred to herein as "TRC 17-18 meganucleases," were engineered to recognize and cleave the TRC 17-18 recognition sequence (SEQ ID NO: 8), which is present in the targeted 5' intron of the human T cell receptor alpha gene. Each TRC 17-18 recombinant meganuclease comprises an N-terminal nuclear-localization signal derived from SV40, a first meganuclease subunit, a linker sequence, and a second meganuclease subunit. A first subunit in each TRC 17-18 meganuclease binds to the TRC17 recognition half-site of SEQ ID NO: 8, while a second subunit binds to the TRC18 recognition half-site (see, FIG. 2).

The TRC17-binding subunits and TRC18-binding subunits each comprise a 56 base pair hypervariable region, referred to as HVR1 and HVR2, respectively. TRC17-binding subunits are highly conserved outside of the HVR1 region. Similarly, TRC18-binding subunits are also highly conserved outside of the HVR2 region. The TRC17-binding regions of SEQ ID NOs: 20-23 are provided as SEQ ID NOs: 44-47, respectively. Each of SEQ ID NOs: 44-47 share at least 90% sequence identity to SEQ ID NO: 44, which is the TRC17-binding region of the meganuclease TRC17-18x.15 (SEQ ID NO: 20). TRC18-binding regions of SEQ ID NOs: 20-23 are provided as SEQ ID NOs: 48-51, respectively. Each of SEQ ID NOs: 48-51 share at least 90% sequence identity to SEQ ID NO: 48, which is the TRC18-binding region of the meganuclease TRC17-18x.15 (SEQ ID NO: 20).

4. Meganucleases that Recognize and Cleave the TRC 19-20 Recognition Sequence Engineered meganucleases (SEQ ID NOs: 24-27), collectively referred to herein as "TRC 19-20 meganucleases," were engineered to recognize and cleave the TRC 19-20 recognition sequence (SEQ ID NO: 10), which is present in the targeted 5' intron of the human T cell receptor alpha gene. Each TRC 19-20 recombinant meganuclease comprises an N-terminal nuclear-localization signal derived from SV40, a first meganuclease subunit, a linker sequence, and a second meganuclease subunit. A first subunit in each TRC 19-20 meganuclease binds to the TRC19 recognition half-site of SEQ ID NO: 10, while a second subunit binds to the TRC20 recognition half-site (see, FIG. 2).

The TRC19-binding subunits and TRC20-binding subunits each comprise a 56 base pair hypervariable region, referred to as HVR1 and HVR2, respectively. TRC19-binding subunits are highly conserved outside of the HVR1 region. Similarly, TRC20-binding subunits are also highly conserved outside of the HVR2 region. The TRC19-binding regions of SEQ ID NOs: 24-27 are provided as SEQ ID NOs: 52-55, respectively. Each of SEQ ID NOs: 52-55 share at least 90% sequence identity to SEQ ID NO: 52, which is the TRC19-binding region of the meganuclease TRC 19-20x.85 (SEQ ID NO: 24). TRC20-binding regions of SEQ ID NOs: 24-27 are provided as SEQ ID NOs: 56-59, respectively. Each of SEQ ID NOs: 56-59 share at least 90% sequence identity to SEQ ID NO: 56, which is the TRC20-binding region of the meganuclease TRC 19-20x.85 (SEQ ID NO: 24).

5. Cleavage of TRC Recognition Sequences in a CHO Cell Reporter Assay

Figure 4:
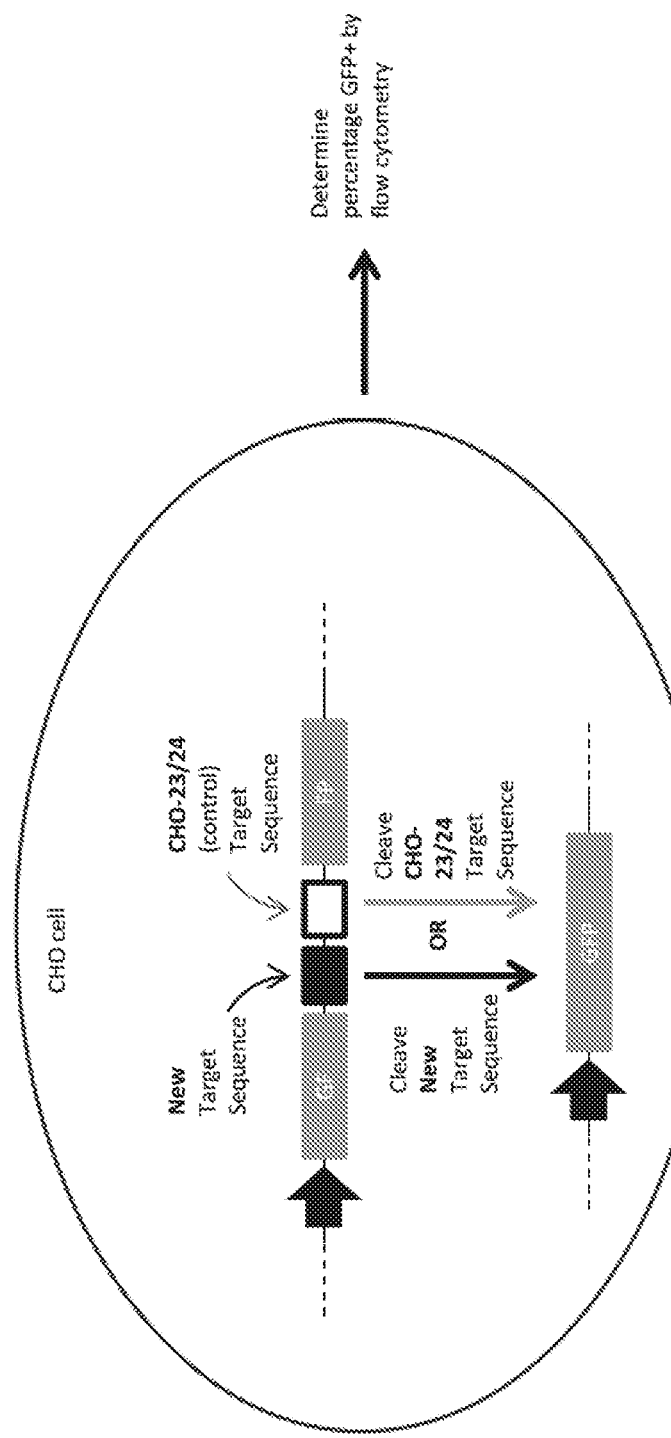
FIG. 4. Schematic of reporter assay in CHO cells for evaluating engineered meganucleases targeting recognition sequences found in the targeted 5' intron of the T cell receptor alpha gene. For the engineered meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the TRC 11-12 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the engineered meganucleases.
Figure 5A:
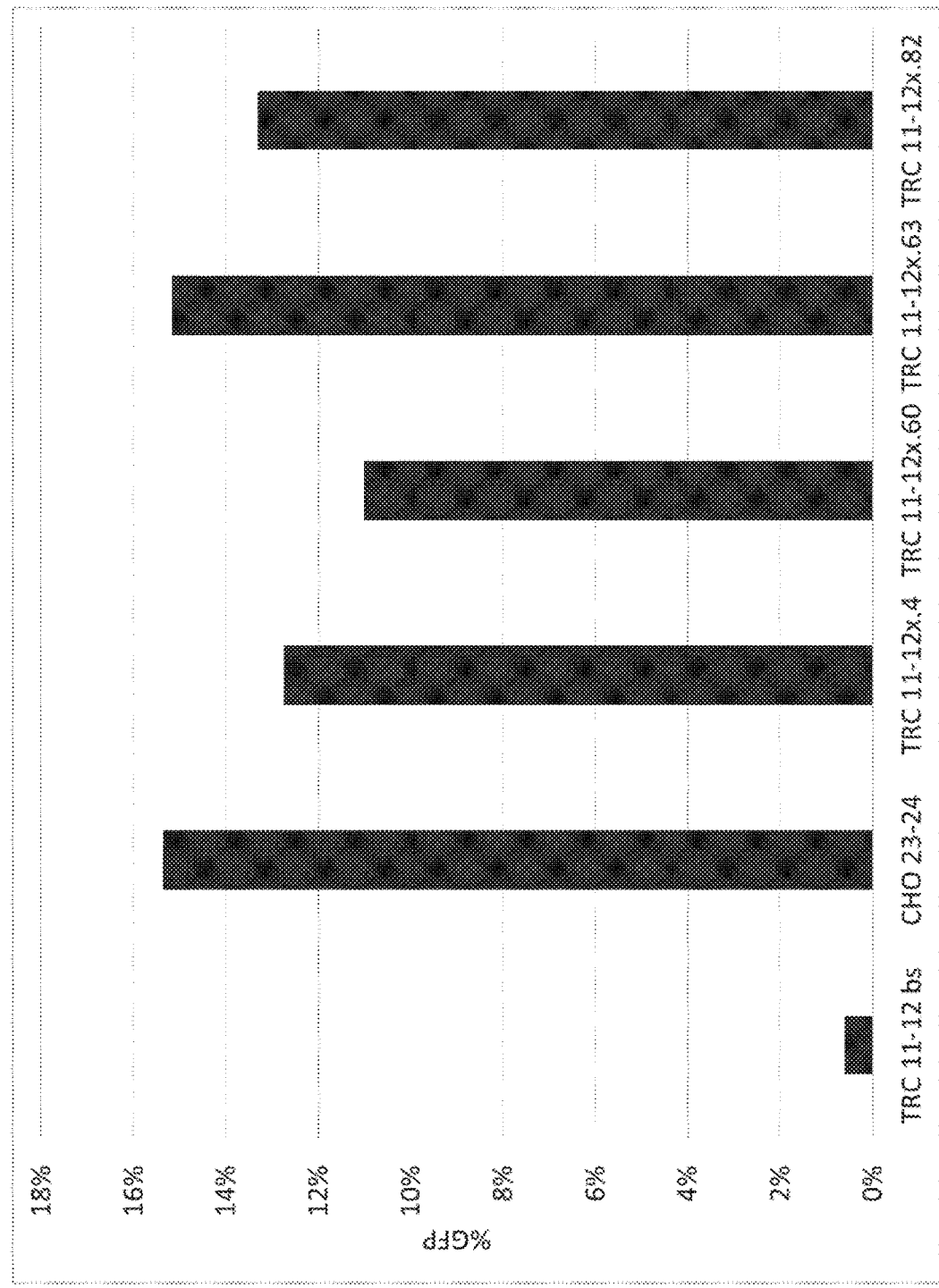
FIG. 5A shows meganucleases targeting the TRC 11-12 recognition sequence.
Figure 5B:
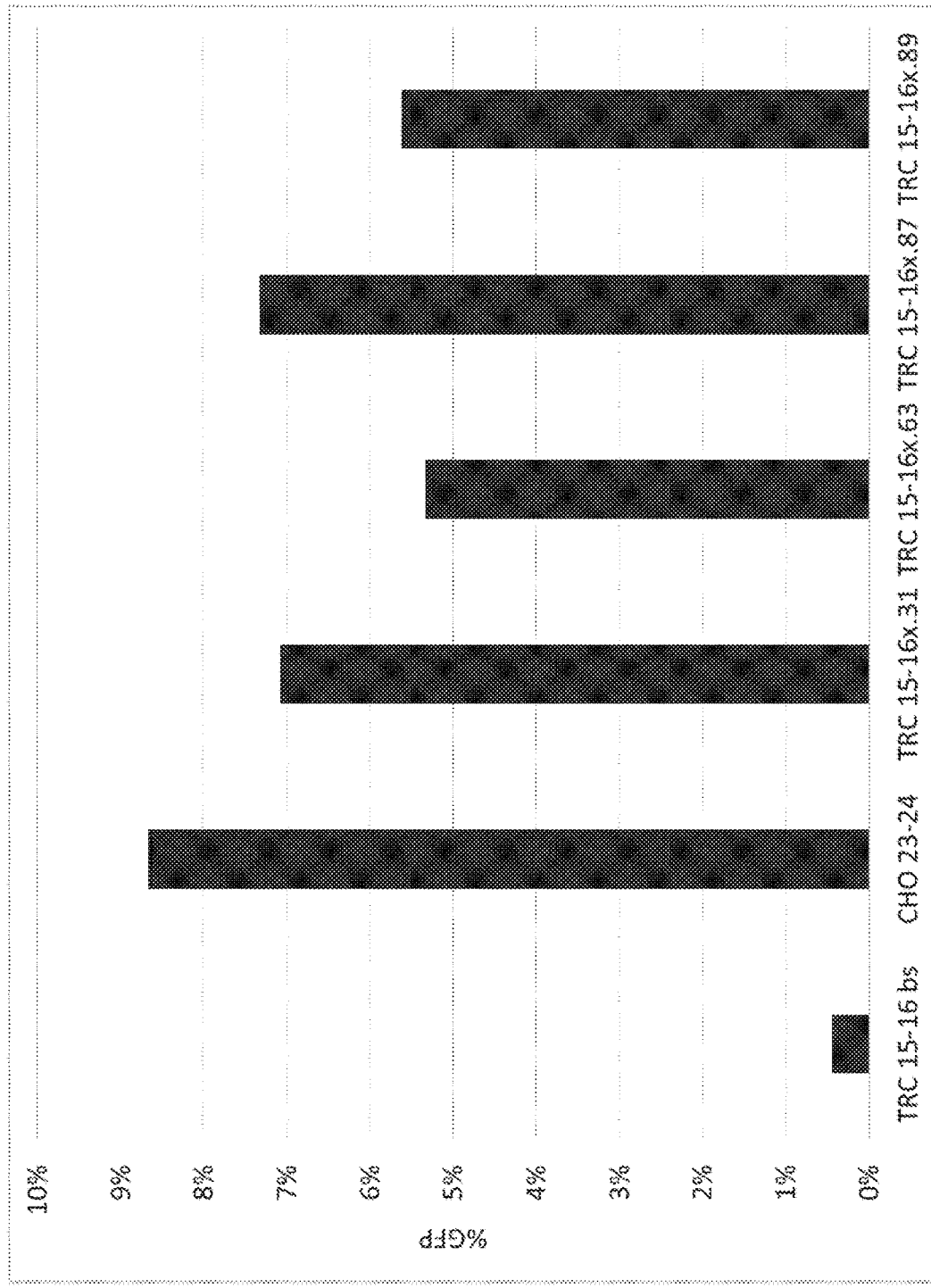
FIG. 5B shows meganucleases targeting the TRC 15-16 recognition sequence.
Figure 5C:
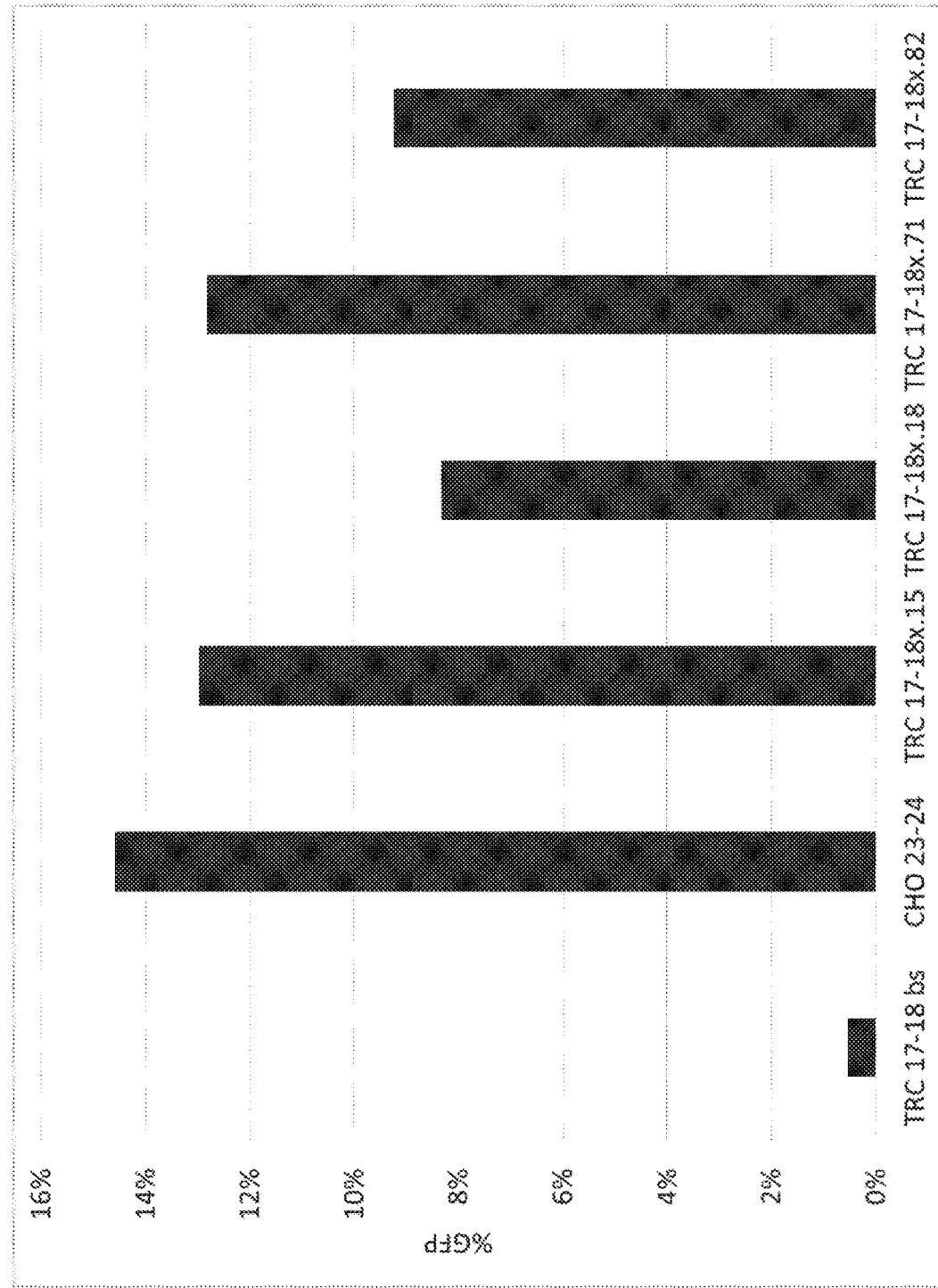
FIG. 5C shows meganucleases targeting the TRC 17-18 recognition sequence.
Figure 5D:
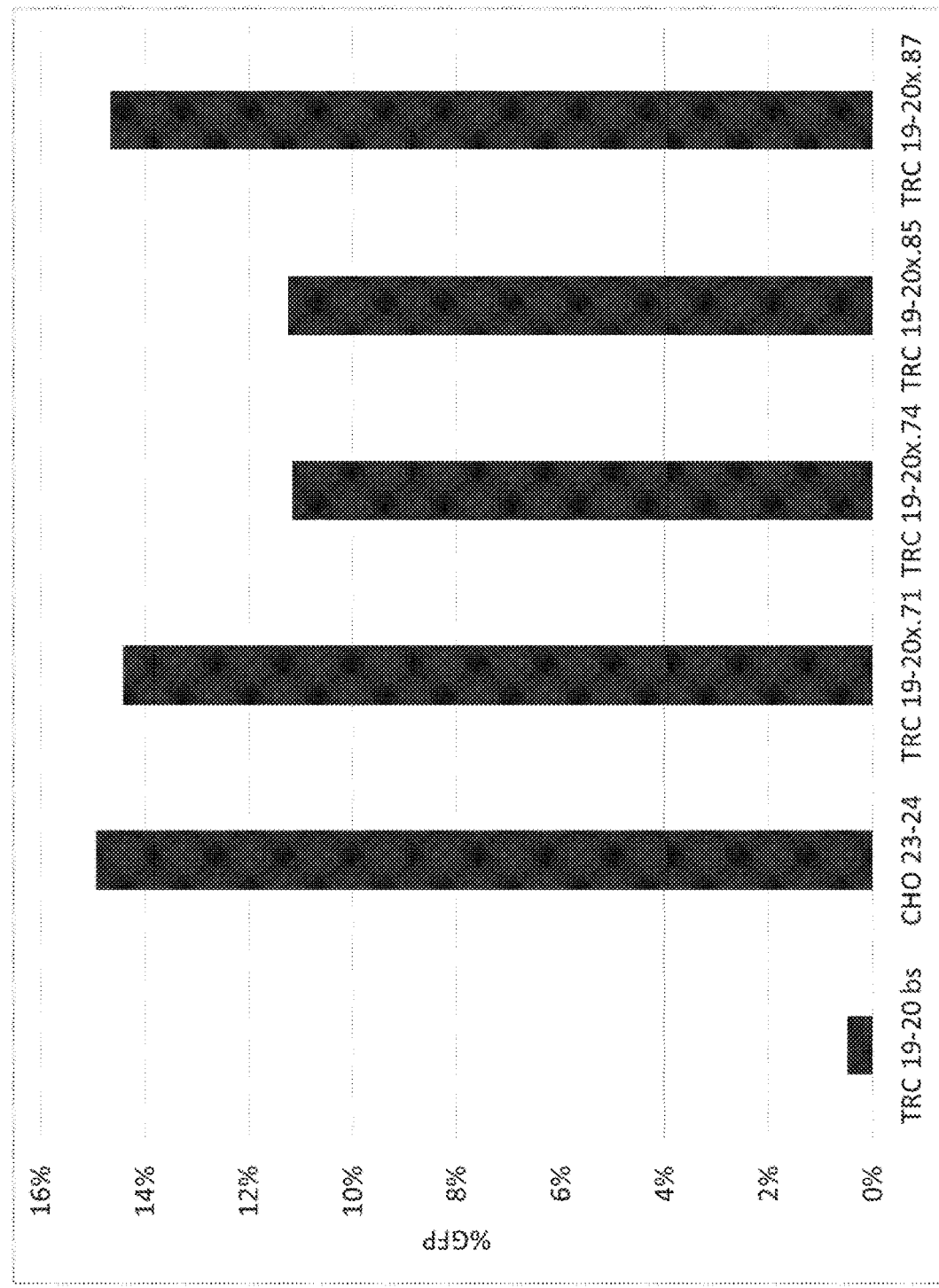
FIG. 5D shows meganucleases targeting the TRC 19-20 recognition sequence.
Figure 6A:
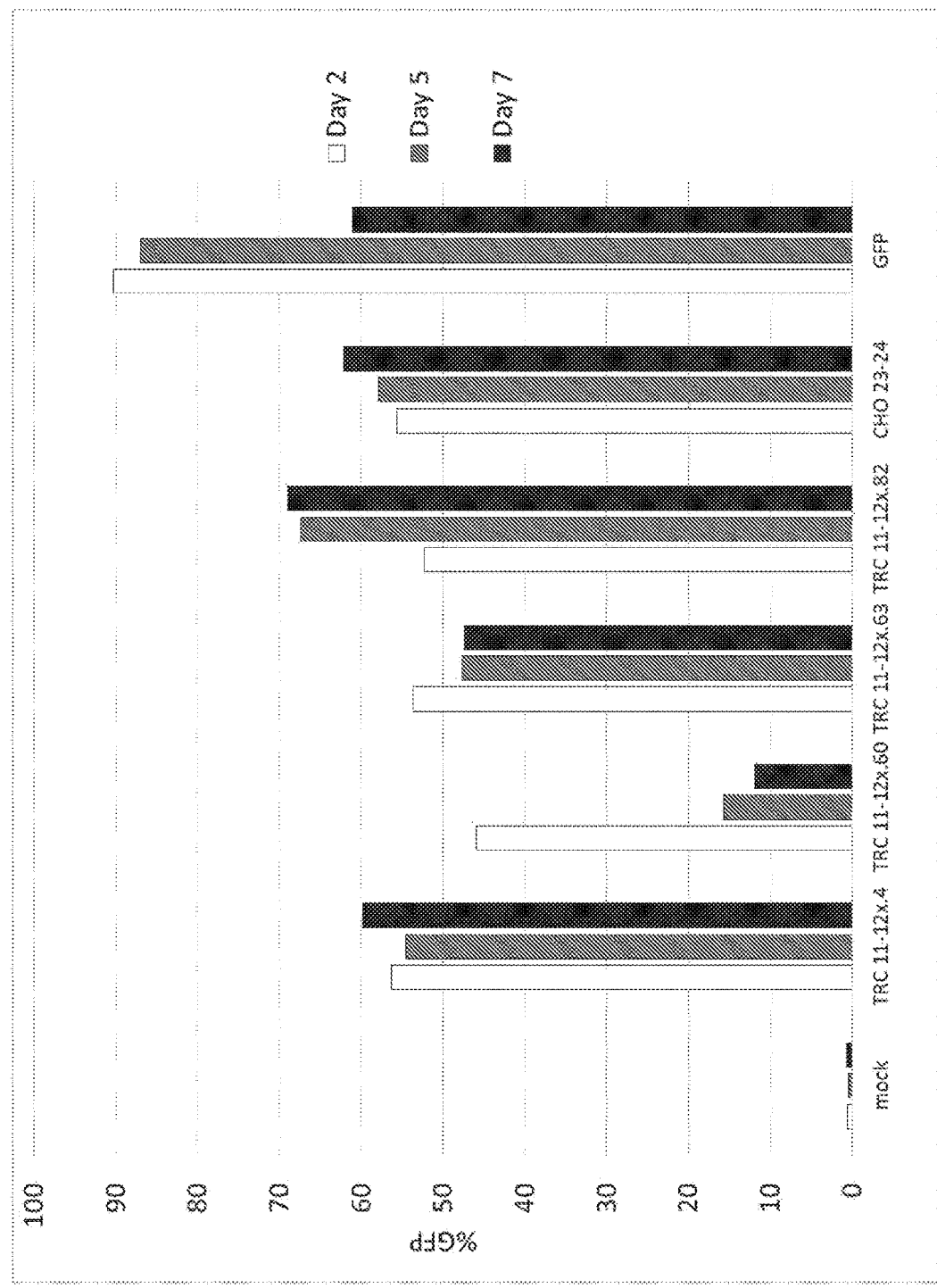
FIG. 6A shows meganucleases targeting the TRC 11-12 recognition sequence.
Figure 6B:
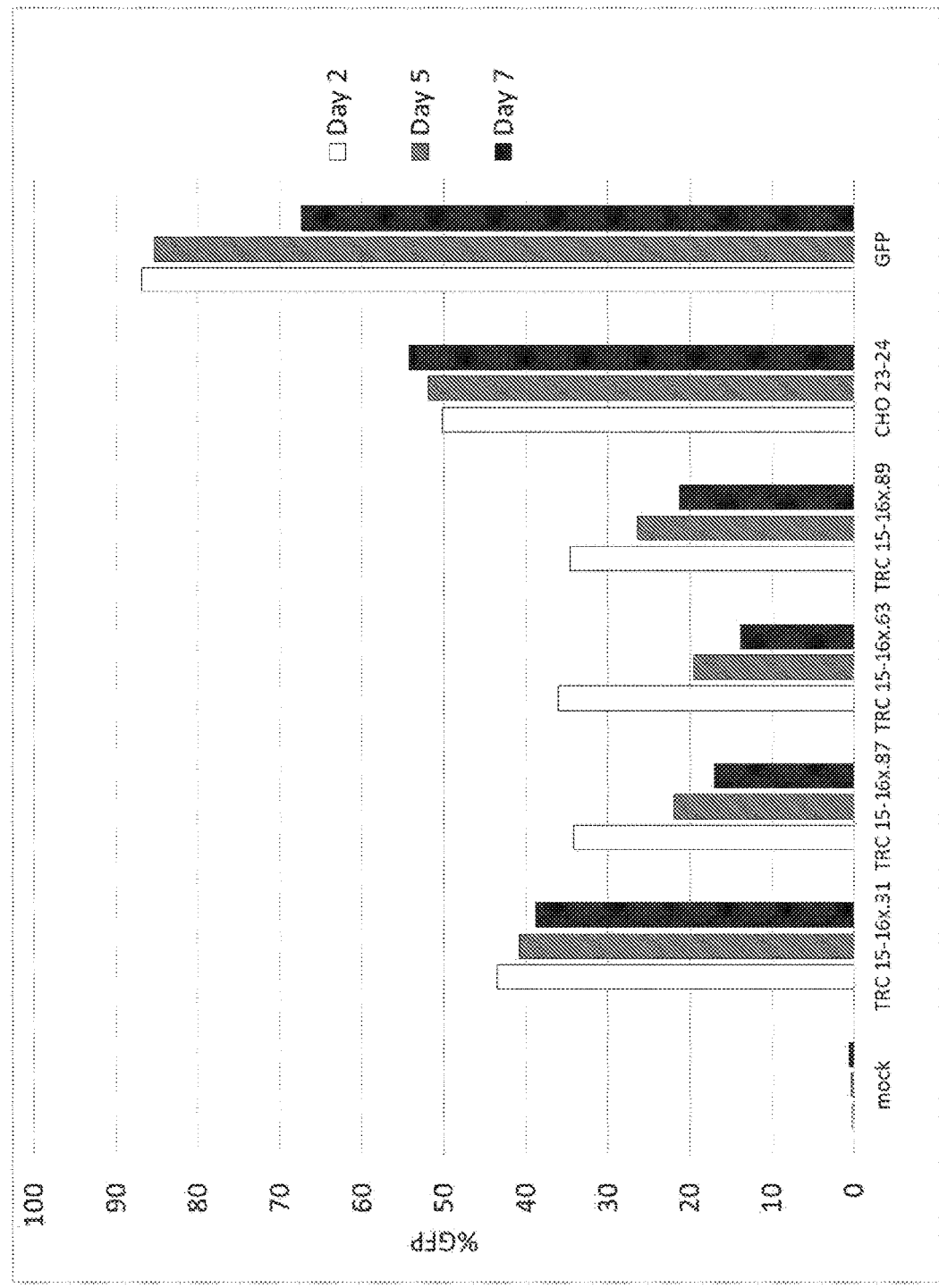
FIG. 6B shows meganucleases targeting the TRC 15-16 recognition sequence.
Figure 6C:
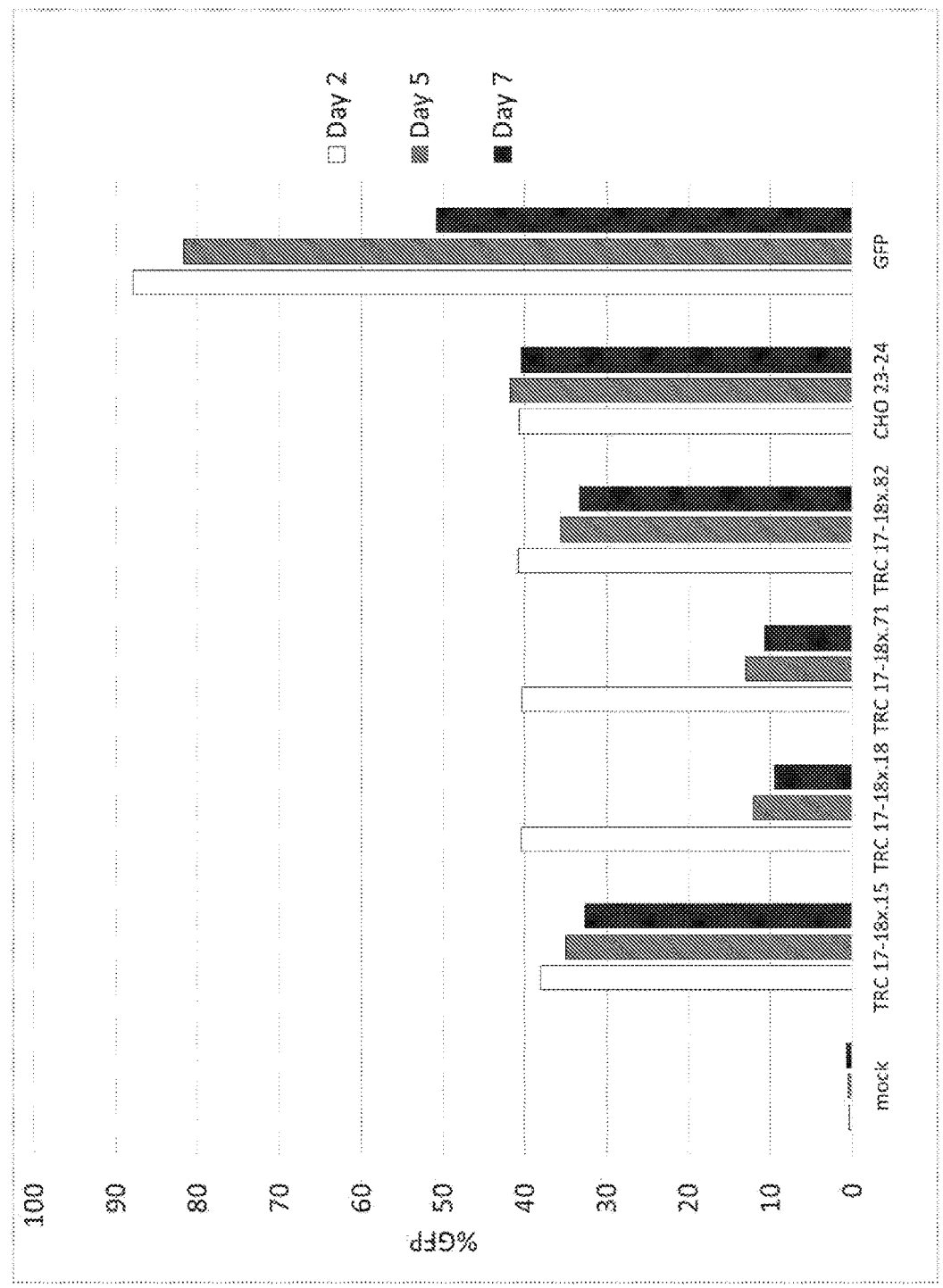
FIG. 6C shows meganucleases targeting the TRC 17-18 recognition sequence.
Figure 6D:
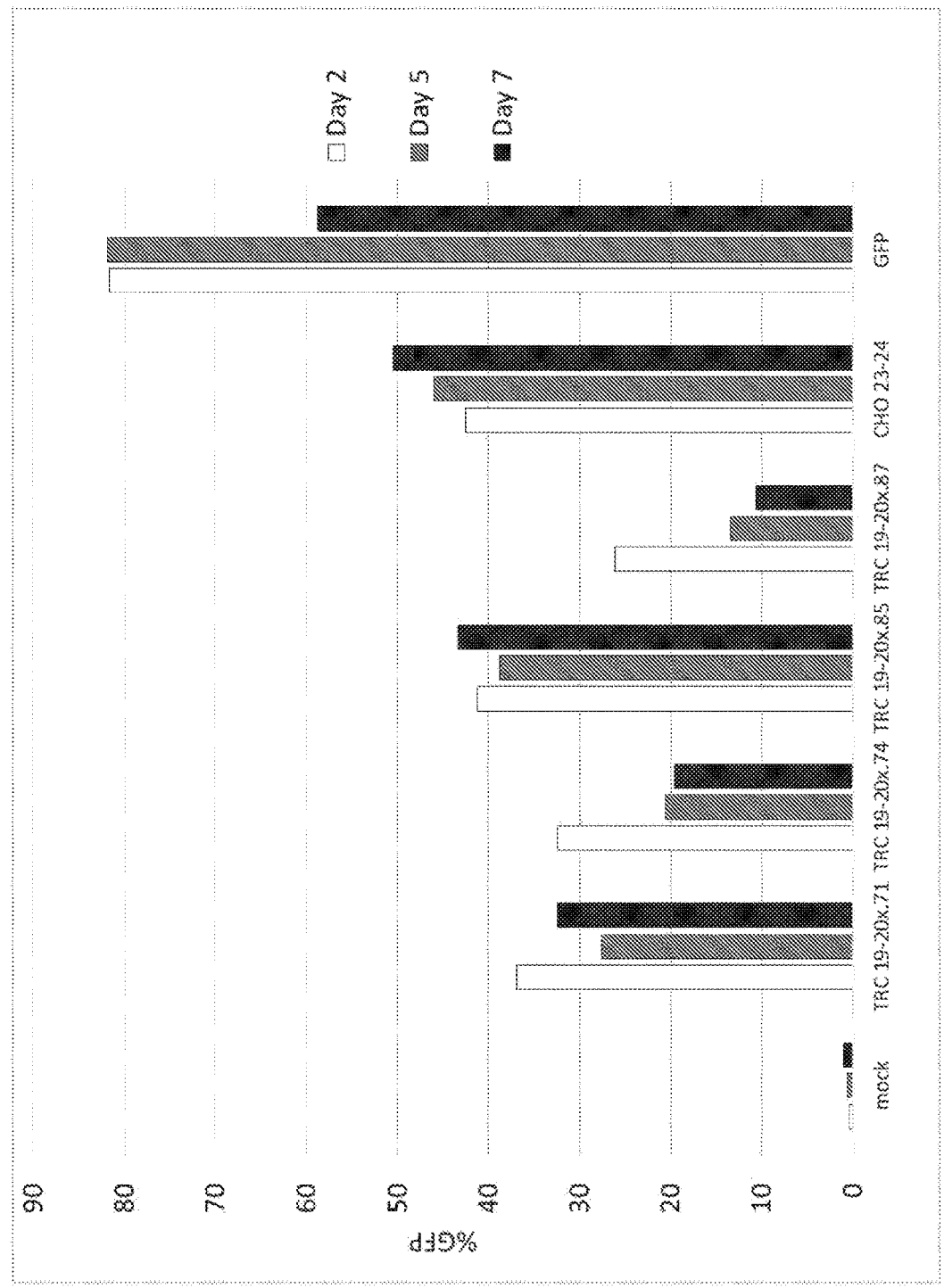
FIG. 6D shows meganucleases targeting the TRC 19-20 recognition sequence.

To determine whether TRC 11-12, TRC 15-16, TRC 17-18, and TRC 19-20 meganucleases could recognize and cleave their respective recognition sequences (SEQ ID NOs: 4, 6, 8, and 10, respectively), each recombinant meganuclease was evaluated using the CHO cell reporter assay previously described (see, WO/2012/167192 and FIG. 4). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the TRC 11-12 recognition sequence (SEQ ID NO: 4), the TRC 15-16 recognition sequence (SEQ ID NO: 6), the TRC 17-18 recognition sequence (SEQ ID NO: 8), or the TRC 19-20 recognition sequence (SEQ ID NO: 10). The second recognition sequence inserted into the GFP gene was a CHO-23/24 recognition sequence, which is recognized and cleaved by a control meganuclease called "CHO-23/24". CHO reporter cells comprising the TRC 11-21 recognition sequence and the CHO-23/24 recognition sequence are referred to herein as "TRC 11-12 cells." CHO reporter cells comprising the TRC 15-16 recognition sequence and the CHO-23/24 recognition sequence are referred to herein as "TRC 15-16 cells." CHO reporter cells comprising the TRC 17-18 recognition sequence and the CHO-23/24 recognition sequence are referred to herein as "TRC 17-18 cells." CHO reporter cells comprising the TRC 19-20 recognition sequence and the CHO-23/24 recognition sequence are referred to herein as "TRC 19-20 cells."

CHO reporter cells were transfected with plasmid DNA encoding their corresponding engineered meganucleases (e.g., TRC 11-12 cells were transfected with plasmid DNA encoding TRC 11-12 meganucleases) or encoding the CHO-23/34 meganuclease. In each assay, $4e^5$ CHO reporter cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (bs). As shown in FIGS. 5A, 5B, 5C, and 5D, all TRC meganucleases were found to produce GFP-positive cells in cell lines comprising their corresponding recognition sequence at frequencies significantly exceeding the negative control.

The efficacy of the TRC 11-12, TRC 15-16, TRC 17-18, and TRC 19-20 engineered meganucleases was also determined in a time-dependent manner 2, 5, and 7 days after introduction of the meganucleases into their corresponding reporter cell line. In this study, each reporter cell line ($1.0 \times 10^6$ cells) was electroporated with $1 \times 10^6$ copies of the corresponding meganuclease mRNA per cell using a BioRad Gene Pulser Xcell according to the manufacturer's instructions. At the specified time intervals, cells were evaluated by flow cytometry to determine the percentage of GFP-positive cells. As shown in FIGS. 6A, 6B, 6C, and 6D, % GFP expression varied among the TRC 11-12, TRC 15-16, TRC 17-18, and TRC 19-20 meganucleases, with some maintaining approximately the same % GFP throughout the course of the study, while others showed a decrease in % GFP expression after 5 or 7 days.

6. Conclusions

These studies demonstrated that TRC 11-12 meganucleases, TRC 15-16 meganucleases, TRC 17-18 meganucleases, and TRC 19-20 meganucleases encompassed by the invention can efficiently target and cleave their respective recognition sequences in cells.

Example 2

Generation of Indels at TRC Recognition Sequences in Human T Cells

1. Background

Figure 7:
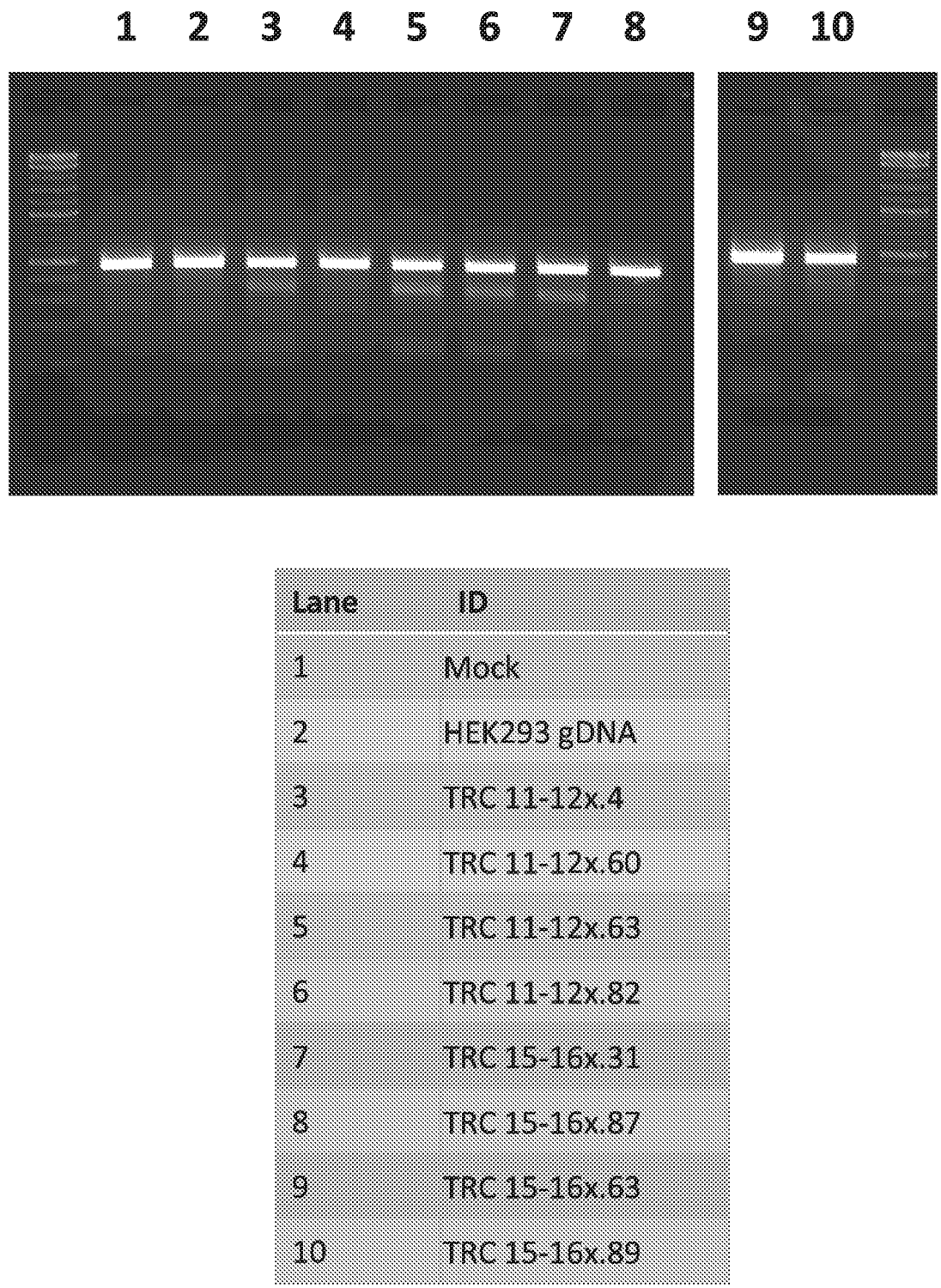
FIG. 7. T7E assay of T cell lysates. Human CD3+ T cells were isolated from PBMCs by magnetic separation and activated for 72 hours. Activated human T cells were electroporated with TRC 11-12 or TRC 15-16 meganuclease mRNA and, at 72 hours post-transfection, genomic DNA (gDNA) was harvested from cells. A T7 endonuclease I (T7E) assay was performed to estimate genetic modification at the endogenous TRC 11-12 or TRC 15-16 recognition sequence.

This study demonstrated that engineered nucleases encompassed by the invention could cleave their respective recognition sequences in human T cells. Human CD3+ T cells were isolated from PBMCs by magnetic separation and activated for 72 hours using antibodies against CD3 and CD28. $1e^6$ activated human T cells were electroporated with $2e^6$ copies of a given TRC 11-12 or TRC 15-16 meganuclease mRNA per cell using a Lonza 4D-Nucleofector according to the manufacturer's instructions. At 72 hours post-transfection, genomic DNA (gDNA) was harvested from cells and a T7 endonuclease I (T7E) assay was performed to estimate genetic modification at the endogenous TRC 11-12 or TRC 15-16 recognition sequence (FIG. 7). In the T7E assay, the TRC 11-12 or TRC 15-6 locus is amplified by PCR using primers that flank the two recognition sequences. If there are indels (random insertions or deletions) within the target locus, the resulting PCR product will consist of a mix of wild-type alleles and mutant alleles. The PCR product is denatured and allowed to slowly reanneal. Slow reannealing allows for the formation of heteroduplexes consisting of wild-type and mutant alleles, resulting in mismatched bases and/or bulges. The T7E1 enzyme cleaves at mismatch sites, resulting in cleavage products that can be visualized by gel electrophoresis.

2. Results

Mock-electroporated cells and control gDNA (Lanes 1 and 2, respectively) both show a single band corresponding to the full-length PCR with no T7E-digested bands, indicating no indels or other polymorphisms are present in either the TRC 11-12 or TRC 15-16 recognition sequences (FIG. 7). Lanes 3, 5 and 6, corresponding to cells electroporated with TRC 11-12x.4, TRC 11-12x.63, and TRC 11-12x.82, respectively, show the full-length PCR band along with smaller T7E-digested bands indicative of indels within the recognition site. Lane 4, corresponding to cells electroporated with TRC 11-12x.60, only showed a full-length PCR band, indicating no indels at the recognition site. Lanes 7, 8, and 10, corresponding to cells electroporated with TRC 15-16x.31, TRC 15-16x.87, and TRC 15-16x.89, respectively, show the full-length PCR band along with smaller T7E-digested bands indicative of indels within the recognition site. Lane 9, corresponding to cells electroporated with TRC 15-16x.63, only showed a full-length PCR band, indicating no indels at the recognition site.

3. Conclusions

These data demonstrate that several TRC 11-12 and TRC 15-16 nucleases are able to cleave their respective recognition sequences in human T cells. Cells electroporated with either TRC 11-12x.4, TRC 11-12x.63, TRC 11-12x.82, TRC 15-16x.31, TRC 15-16x.87, or TRC 15-16x.89 all showed T7E-digested bands, demonstrating the presences of indels in their respective recognition sequences.

Example 3

Effect of TRC Recognition Sequence Cleavage on T Cell Receptor Expression

1. Background

The purpose of these experiments was to demonstrate whether cleavage of a TRC recognition sequence within the targeted 5' intron of the T cell receptor alpha gene, and subsequent repair by NHEJ, would affect expression of the endogenous T cell receptor.

Human T cells were magnetically enriched using a CD3 positive selection kit and a Robo-Sep automated magnetic separator (both from Stem Cell Technologies). T cells were enriched from an apheresis sample obtained from a compensated, healthy human volunteer. T cells were stimulated for 3 days using T cell Activator (antiCD3/anti/CD28) Dynabeads (LifeTechnologies) at a 1:1 cell:bead ratio in the presence of 10 ng/ml if IL-2. After 3 days, T cells were harvested, Dynabeads were removed using the DynaMag magnet (Life Technologies), and 1 µg of the indicated meganuclease RNA was introduced to T cell samples using the Lonza 4-D nucleofector. Nucleofected cells were cultured for 6 days prior to flow cytometric analysis. CD3 surface display was measured by labeling T cell samples with 10 of anti-CD3-BrilliantViolet711 (BioLegend product 300464) and 0.3 µl of GhostDye-510 (Tonbo Biosciences) per sample of $2.0 \times 10^5$ cells. Data were acquired using a Beckman-Coulter CytoFLEX-S cytometer.

2. Results

T cells were nucleofected with either TRC 1-2x.87EE (an engineered nuclease which targets TRAC exon 1) or no RNA (mock) to serve as positive and negative controls for TRAC locus editing, respectively, and appear in FIG. 8A and FIG. 8B. Four additional samples were also nucleofected with RNA encoding one distinct nuclease variant from the TRC 15-16 family, all members of which target the TRC 15-16 recognition sequence in the 5' intron. When TRAC locus editing results in gene disruption, no TCRα chains are synthesized, and no TCR complex (including CD3) is displayed on the surface of edited cells. Greater than half of the TRC 1-2x.87EE edited T cells were shown to be TRC negative due to cleavage in exon 1 and error-prone repair of the cleavage site by NHEJ (FIG. 8B). By comparison, the frequency of TCR negative cells following editing by TRC 15-16x.31, TRC 15-16x.63, TRC 15-16x.87, and TRC 15-16x.89 was between only 4% and 8% (FIGS. 8C, 8D, 8E, and 8F, respectively).

3. Conclusions

These experiments demonstrate that targeting recognition sequences in the 5' intron upstream of TRAC exon 1 can produce indels (as observed in the T7E assay) but do not substantially affect cell surface expression of the endogenous T cell receptor. We expect that insertion of a construct into this cleavage site, which comprises an exogenous splice acceptor site, a CAR coding sequence, and a polyA signal, will knock out TCR expression in cells.

Example 4

Insertion of a Sequence of Interest into the Targeted 5' Intron

The purpose of these experiments is to generate a double strand cleavage in the targeted 5' intron and to insert an exogenous sequence of interest into the cleavage site by homologous recombination, thus allowing for: (i) disrupted expression of the endogenous T cell receptor due to the presence of an exogenous splice acceptor site and/or a poly A signal, and (ii) expression of a protein of interest encoded by the insert.

In these examples, the exogenous sequence of interest includes a number of elements which are shown in the constructs of FIG. 9. Each construct is flanked by a 5' homology arm and a 3' homology arm. These arms have homology to the sequences 5' upstream and 3' downstream of their respective TRC recognition sequences in the targeted 5' intron. The size of each homology and, and the percent homology of the arm to the corresponding sequence in the targeted 5' intron, can be modulated as needed to improve homologous recombination of the construct into the cleavage site. Adjacent to the 5' homology arm is a chimeric intron which comprises both an exogenous branch site for splicing and an exogenous splice acceptor site. A T2A element is then included 5' to an anti-CD19 CAR sequence, which includes a signal peptide, an anti-CD19 scFv, a CD8 hinge and transmembrane domain, an N6 co-stimulatory domain, and a CD3ζ signaling domain. The CAR coding sequence is followed by a bi-polyA signal, and finally a 3' homology arm. The specific constructs provided in FIGS. 9A-9C target the TRC 11-12, TRC 15-16, and TRC 17-18 recognition sequences, respectively, and are provided in SEQ ID NOs: 60-62.

Donor human T cells can be obtained, activated, and transfected with TRC meganuclease mRNA as described in the previous Examples. The donor template comprising the exogenous sequence of interest (e.g., SEQ ID NOs: 60-62, FIGS. 9A-9C) can be introduced by a number of means known in the art, but preferably by transduction of a recombinant AAV which comprises the donor template. Transduction can be performed at any time relative to transfection with the meganuclease mRNA, but preferably transduction and transfection are performed at the same time. The level of T cell receptor expression, and the level of CAR expression, will each be determined in the cells over a number of time points by flow cytometry (as described above and by methods known in the art). It is expected that the vast majority of TCR− cells obtained by this method will also be CAR+, as any cells which do not have the insert at the cleavage site will continue to express the endogenous TCR.

In a particular study, a promoterless GFP or CAR coding sequence was inserted into the targeted 5' intron to demonstrate that the endogenous TCR promoter could drive expression of these proteins when they were introduced using a construct of the invention. In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28-Stem Cell Technologies) in X-VIVO 15 medium (Lonza) supplemented with 5% fetal bovine serum and 10 ng/ml IL-2 (Gibco). After 3 days of stimulation, cells were collected and RNA encoding one of two TRC nucleases was introduced to the T cells by way of electroporation with the 4-D Nucleofector (Lonza). T cells received RNA encoding either TRC 11-12x.82 or TRC 15-16x.31.

Cells receiving TRC 11-12x.82 RNA were transduced with one of two AAV6 vectors containing regions of homology to genomic sequences flanking the TRC 11-12x.82 recognition sequence (i.e., the TRC 11-12 recognition sequence). One vector, containing construct 7227 (SEQ ID NO: 63), encodes a T2A sequence followed by a promoterless GFP gene, while the other vector contains construct 7225 (SEQ ID NO: 64), which encodes a T2A sequence followed by a promoterless CAR gene.

Cells receiving TRC 15-16.x31 RNA were transduced with one of two AAV6 vectors containing regions of homology to genomic sequences flanking the TRC 15-16x.31 recognition sequence (i.e., the TRC 15-16 recognition sequence). One vector, containing construct 7228 (SEQ ID NO: 65), encodes a T2A sequence followed by a promoterless GFP gene, while the other vector contains construct 7226 (SEQ ID NO: 66), which encodes a T2A sequence followed by a promoterless CAR gene.

All transductions were carried out with a multiplicity of infection (MOI) of 50,000 (viral genomes/cell). Cell cultures were maintained for 5 additional days in X-VIVO15 medium supplemented with 5% FBS and 30 ng/ml of IL-2. On day 5, analyses of TRC knockout, and GFP or CAR knock-in, were performed by staining cells for CD3 (Anti-CD3-APC/750 or -BV711, BioLegend) and CAR (anti-FMC63-biotin+ streptavidin-PE, produced in-house) and measuring signal with a Beckman-Coulter CytoFLEX-S flow cytometer.

2. Results

The frequencies of TCR knockout cells (CD3+ vs CD3− frequencies) and GFP knock-in cells appear in FIG. 10. Following administration of TRC 11-12x.82 and AAV6-7227, 18% of all T cells in culture are CD3-GFP+ (FIG. 10A). When gating on only the TCR-edited (CD3−) population, 85% of cells were GFP+ (FIG. 10B). Administration of TRC 15-16x.31 and AAV6-7228 produced a slightly lower frequency of CD3−/GFP+ cells (12.6%, FIG. 10C), although the frequency of GFP+ cells in the CD3− population was still above 80% (FIG. 10D).

CAR knock-in (FMC63+) into the targeted 5' intron is shown in FIG. 11. Relative to edited cells that were not transduced with a CAR vector, (FIG. 11A), staining samples with anti-FMC63 and anti-CD3 identifies knockout as well as knock-in populations in vector-transduced samples (histograms in FIG. 11 are gated on CD3-negative events). Insertion of the promoterless CAR constructs at the TRC 11-12 and TCR 15-16 recognition sequences (FIGS. 11B and 11C, respectively) each yielded CD3−/CAR+ events, indicating that the endogenous TCR promoter drove expression of the CAR coding sequence when inserted into the targeted 5' intron.

3. Conclusions

The observation of CD3−/GFP+, or CD3−/CAR+, events after administration of TCR intron-specific meganucleases along with T2A-transgene constructs of corresponding homology indicates that the endogenous TCR transcriptional control elements can be used to drive expression of proteins of interest.

The invention claimed is:

1. An isolated genetically-modified human T cell comprising in its genome a modified human T cell receptor alpha gene, wherein said modified human T cell receptor alpha gene comprises an exogenous sequence of interest inserted into an intron within the human T cell receptor alpha gene that is positioned 5' upstream of the T cell receptor alpha constant region (TRAC) exon 1, and wherein said exogenous sequence of interest comprises an exogenous splice acceptor site or an exogenous splice acceptor site and a poly A signal, and wherein an endogenous splice donor site and an endogenous splice acceptor site flanking said intron are unmodified, and wherein cell surface expression of an endogenous human T cell receptor is reduced when compared to an unmodified control cell.

2. The isolated genetically-modified human T cell of claim 1, wherein said intron comprises SEQ ID NO: 3.

3. The isolated genetically-modified human T cell of claim 1, wherein said exogenous sequence of interest comprises, from 5' to 3', an exogenous splice acceptor site, a 2A element or IRES element, a coding sequence for a protein of interest, and a polyA signal.

4. The isolated genetically-modified human T cell of claim 3, wherein said 2A element is a T2A, a P2A, an E2A, or an F2A element.

5. The isolated genetically-modified human T cell of claim 3, wherein said 2A element is a T2A element.

6. The isolated genetically-modified human T cell of claim 1, wherein said sequence of interest comprises a coding sequence for a chimeric antigen receptor or an exogenous T cell receptor.

7. The isolated genetically-modified human T cell of claim 1, wherein said exogenous sequence of interest is inserted into said intron at an engineered meganuclease recognition site.

8. An isolated population of genetically-modified human T cells comprising a plurality of said isolated genetically-modified human T cell of claim 1.

9. A pharmaceutical composition useful for treatment of a disease in a subject in need thereof, wherein said pharmaceutical composition comprises a pharmaceutically-acceptable carrier and said isolated genetically-modified human T cell of claim 1.

10. A method of treating a disease in a subject in need thereof, said method comprising administering to said subject said isolated genetically-modified human T cell of claim 1.

* * * * *

SEQUENCE LISTING

```
<160> NUMBER OF SEQ ID NOS: 66

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 577
<212> TYPE: DNA
<213> ORGANISM: Homo sapiens

<400> SEQUENCE: 3
tgctgtgact tgctcaaggc cttatatcaa gtaaacggta gcgctggggc ttagacgcag      60
gtgttctgat ttatagttca aaacctctat caatgagaga gcaatctcct ggtaatgtga     120
tagatttccc aacttaatgc caacatacca taaacctccc attctgctaa tgcccagcct     180
aagttgggga gaccactcca gattccaaga tgtacagttt gctttgctgg gcctttttcc     240
catgcctgcc tttactctgc cagagttata ttgctggggt tttgaagaag atcctattaa     300
ataaaagaat aagcagtatt attaagtagc cctgcatttc aggtttcctt gagtggcagg     360
ccaggcctgg ccgtgaacgt tcactgaaat catggcctct tggccaagat tgatagcttg     420
tgcctgtccc tgagtcccag tccatcacga gcagctggtt tctaagatgc tatttcccgt     480
ataaagcatg agaccgtgac ttgccagccc cacagagccc cgcccttgtc catcactggc     540
atctggactc cagcctgggt tggggcaaag agggaaa                              577

<210> SEQ ID NO 4
<211> LENGTH: 22
<212> TYPE: DNA
<213> ORGANISM: Homo sapiens

<400> SEQUENCE: 4
tgatagcttg tgcctgtccc tg                                               22

<210> SEQ ID NO 5
<211> LENGTH: 22
<212> TYPE: DNA
<213> ORGANISM: Homo sapiens

<400> SEQUENCE: 5
actatcgaac acggacaggg ac                                               22

<210> SEQ ID NO 6
```

-continued

```
<211> LENGTH: 22
<212> TYPE: DNA
<213> ORGANISM: Homo sapiens

<400> SEQUENCE: 6
cagtttgctt tgctgggcct tt                                              22

<210> SEQ ID NO 7
<211> LENGTH: 22
<212> TYPE: DNA
<213> ORGANISM: Homo sapiens

<400> SEQUENCE: 7
gtcaaacgaa acgacccgga aa                                              22

<210> SEQ ID NO 8
<211> LENGTH: 22
<212> TYPE: DNA
<213> ORGANISM: Homo sapiens

<400> SEQUENCE: 8
tgctgtgact tgctcaaggc ct                                              22

<210> SEQ ID NO 9
<211> LENGTH: 22
<212> TYPE: DNA
<213> ORGANISM: Homo sapiens

<400> SEQUENCE: 9
acgacactga acgagttccg ga                                              22

<210> SEQ ID NO 10
<211> LENGTH: 22
<212> TYPE: DNA
<213> ORGANISM: Homo sapiens

<400> SEQUENCE: 10
tgggttgggg caaagaggga aa                                              22

<210> SEQ ID NO 11
<211> LENGTH: 22
<212> TYPE: DNA
<213> ORGANISM: Homo sapiens

<400> SEQUENCE: 11
acccaacccc gtttctccct tt                                              22

<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Gln Pro Ser Gln His
            20                  25                  30

Arg Lys Phe Lys His Gln Leu Val Leu Trp Phe Arg Val Thr Gln Lys
        35                  40                  45

Thr Gln Arg Arg Trp Phe Leu Asp Lys Leu Val Asp Glu Ile Gly Val
    50                  55                  60
```

```
Gly Tyr Val Arg Asp Thr Gly Ser Val Ser Tyr Tyr Ser Leu Ser Gln
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Thr Ile Asn Pro Val Gln Trp Asn
210                 215                 220

Lys Phe Lys His Gln Leu Arg Leu Thr Phe Ala Val Thr Gln Lys Thr
225                 230                 235                 240

Gln Arg Arg Trp Phe Leu Asp Lys Leu Val Asp Glu Ile Gly Val Gly
                245                 250                 255

Tyr Val Ser Asp Trp Gly Ser Val Ser Gln Tyr Lys Leu Ser Glu Ile
        260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
        340                 345                 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Arg Pro Asp Gln Val
            20                  25                  30

Arg Lys Phe Lys His Gln Leu Thr Leu Tyr Phe Arg Val Ser Gln Lys
        35                  40                  45

Thr Gln Arg Arg Trp Phe Leu Asp Lys Leu Val Asp Glu Ile Gly Val
    50                  55                  60
```

-continued

Gly Tyr Val Asn Asp Cys Gly Ser Val Ser His Tyr Ser Leu Ser Gln
65                  70                  75                  80

Ile Lys Pro Leu His Asn Phe Leu Thr Gln Leu Gln Pro Phe Leu Lys
            85                  90                  95

Leu Lys Gln Lys Gln Ala Asn Leu Val Leu Lys Ile Ile Glu Gln Leu
        100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Asp Pro Glu Gln Thr Gly
    210                 215                 220

Lys Phe Lys His Lys Leu Arg Leu Arg Phe Val Thr Gln Lys Thr
225                 230                 235                 240

Gln Arg Arg Trp Phe Leu Asp Lys Leu Val Asp Glu Ile Gly Val Gly
                245                 250                 255

Tyr Val Thr Asp Trp Gly Ser Val Ser Tyr Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Gln Pro Ser Gln His
            20                  25                  30

Arg Lys Phe Lys His Gln Leu Val Leu Trp Phe Arg Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Tyr Tyr Ser Leu Ser Lys

```
                65                  70                  75                  80
        Ile Lys Pro Leu His Asn Phe Leu Thr Gln Leu Gln Pro Phe Leu Lys
                        85                  90                  95

Leu Lys Gln Lys Gln Ala Asn Leu Val Leu Lys Ile Ile Glu Gln Leu
                    100                 105                 110

Pro Ser Ala Lys Glu Ser Pro Asp Lys Phe Leu Glu Val Cys Thr Trp
                    115                 120                 125

Val Asp Gln Ile Ala Ala Leu Asn Asp Ser Lys Thr Arg Lys Thr Thr
                    130                 135                 140

Ser Glu Thr Val Arg Ala Val Leu Asp Ser Ser Pro Gly Ser Val Gly
        145                 150                 155                 160

Gly Leu Ser Pro Ser Gln Ala Ser Ser Ala Ala Ser Ala Ser Ser
                        165                 170                 175

Ser Pro Gly Ser Gly Ile Ser Glu Ala Leu Arg Ala Gly Ala Gly Ser
                    180                 185                 190

Gly Thr Gly Tyr Asn Lys Glu Phe Leu Leu Tyr Leu Ala Gly Phe Val
                    195                 200                 205

Asp Gly Asp Gly Ser Ile Phe Ala Ser Ile Glu Pro Ile Gln Tyr Ser
                    210                 215                 220

Lys Phe Lys His Arg Leu Lys Leu Tyr Phe Ala Val Ser Gln Lys Thr
        225                 230                 235                 240

Gln Arg Arg Trp Phe Leu Asp Lys Leu Val Asp Glu Ile Gly Val Gly
                        245                 250                 255

Tyr Val Thr Asp His Gly Ser Val Ser Thr Tyr Arg Leu Ser Lys Ile
                    260                 265                 270

Lys Pro Leu His Asn Phe Leu Thr Gln Leu Gln Pro Phe Leu Lys Leu
                    275                 280                 285

Lys Gln Lys Gln Ala Asn Leu Val Leu Lys Ile Ile Glu Gln Leu Pro
                    290                 295                 300

Ser Ala Lys Glu Ser Pro Asp Lys Phe Leu Glu Val Cys Thr Trp Val
        305                 310                 315                 320

Asp Gln Ile Ala Ala Leu Asn Asp Ser Lys Thr Arg Lys Thr Thr Ser
                        325                 330                 335

Glu Thr Val Arg Ala Val Leu Asp Ser Leu Ser Glu Lys Lys Lys Ser
                    340                 345                 350

Ser Pro

<210> SEQ ID NO 15
<211> LENGTH: 354
<212> TYPE: PRT
<213> ORGANISM: Artificial Sequence
<220> FEATURE:
<223> OTHER INFORMATION: Synthesized

<400> SEQUENCE: 15

Met Asn Thr Lys Tyr Asn Lys Glu Phe Leu Leu Tyr Leu Ala Gly Phe
        1               5                   10                  15

Val Asp Gly Asp Gly Ser Ile Tyr Ala Thr Ile Gln Pro Gly Gln Thr
                        20                  25                  30

Arg Lys Phe Lys His Gln Leu Ser Leu Trp Phe Arg Val Thr Gln Lys
                    35                  40                  45

Thr Gln Arg Arg Trp Phe Leu Asp Lys Leu Val Asp Glu Ile Gly Val
                50                  55                  60

Gly Tyr Val Ser Asp Ala Gly Ser Val Ser His Tyr Ser Leu Ser Gln
        65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ala Ile Glu Pro Thr Gln Cys Ala
210                 215                 220

Lys Phe Lys His Lys Leu Arg Leu Leu Phe Ala Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gln Gly Ser Val Ser Thr Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 16
<211> LENGTH: 354
<212> TYPE: PRT
<213> ORGANISM: Artificial Sequence
<220> FEATURE:
<223> OTHER INFORMATION: Synthesized

<400> SEQUENCE: 16

Met Asn Thr Lys Tyr Asn Lys Glu Phe Leu Leu Tyr Leu Ala Gly Phe
1               5                   10                  15

Val Asp Gly Asp Gly Ser Ile His Ala Thr Ile Val Pro Ser Gln Gln
            20                  25                  30

Tyr Lys Phe Lys His Arg Leu His Leu Phe Phe Gly Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Arg Tyr Ile Leu Ser Glu
65                  70                  75                  80
```

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Leu Pro Val Gln Val Ala
        210                 215                 220

Lys Phe Lys His Gln Leu Arg Leu Thr Phe Arg Val Gly Gln Lys Thr
225                 230                 235                 240

Gln Arg Arg Trp Phe Leu Asp Lys Leu Val Asp Glu Ile Gly Val Gly
            245                 250                 255

Tyr Val Ser Asp Ser Gly Ser Val Ser Asn Tyr Glu Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
        340                 345                 350

Ser Pro

<210> SEQ ID NO 17
<211> LENGTH: 354
<212> TYPE: PRT
<213> ORGANISM: Artificial Sequence
<220> FEATURE:
<223> OTHER INFORMATION: Synthesized

<400> SEQUENCE: 17

Met Asn Thr Lys Tyr Asn Lys Glu Phe Leu Leu Tyr Leu Ala Gly Phe
1               5                   10                  15

Val Asp Gly Asp Gly Ser Ile His Ala Thr Ile Val Pro Ser Gln Gln
            20                  25                  30

Tyr Lys Phe Lys His Arg Leu His Leu Phe Phe Gly Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Arg Tyr Ile Leu Ser Glu
65                  70                  75                  80

Ile Lys Pro Leu His Asn Phe Leu Thr Gln Leu Gln Pro Phe Leu Lys
```

```
                85                  90                  95
Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Tyr Ala Arg Ile Gly Pro Gly Gln Thr Tyr
                210                 215                 220

Lys Phe Lys His Gln Leu Lys Leu Thr Phe Ser Val Ser Gln Lys Thr
225                 230                 235                 240

Gln Arg Arg Trp Phe Leu Asp Lys Leu Val Asp Glu Ile Gly Val Gly
                245                 250                 255

Tyr Val Glu Asp Phe Gly Ser Val Ser Lys Tyr Ile Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 18
<211> LENGTH: 354
<212> TYPE: PRT
<213> ORGANISM: Artificial Sequence
<220> FEATURE:
<223> OTHER INFORMATION: Synthesized

<400> SEQUENCE: 18

Met Asn Thr Lys Tyr Asn Lys Glu Phe Leu Leu Tyr Leu Ala Gly Phe
1               5                   10                  15

Val Asp Gly Asp Gly Ser Ile His Ala Thr Ile Val Pro Ser Gln Gln
                20                  25                  30

Tyr Lys Phe Lys His Arg Leu His Leu Phe Gly Val Tyr Gln Lys
            35                  40                  45

Thr Gln Arg Arg Trp Phe Leu Asp Lys Leu Val Asp Glu Ile Gly Ala
    50                  55                  60

Gly Tyr Val Tyr Asp Gly Gly Ser Val Ser Arg Tyr Ile Leu Ser Gln
65                  70                  75                  80

Ile Lys Pro Leu His Asn Phe Leu Thr Gln Leu Gln Pro Phe Leu Lys
                85                  90                  95
```

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Arg Ile Gly Pro Gly Gln Thr Tyr
    210                 215                 220

Lys Phe Lys His Gln Leu Lys Leu Thr Phe Ser Val Ser Gln Lys Thr
225                 230                 235                 240

Gln Arg Arg Trp Phe Leu Asp Lys Leu Val Asp Glu Ile Gly Val Gly
                245                 250                 255

Tyr Val Glu Asp Phe Gly Ser Val Ser Lys Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 19
<211> LENGTH: 354
<212> TYPE: PRT
<213> ORGANISM: Artificial Sequence
<220> FEATURE:
<223> OTHER INFORMATION: Synthesized

<400> SEQUENCE: 19

Met Asn Thr Lys Tyr Asn Lys Glu Phe Leu Leu Tyr Leu Ala Gly Phe
1               5                   10                  15

Val Asp Gly Asp Gly Ser Ile His Ala Thr Ile Val Pro Ser Gln Gln
            20                  25                  30

Tyr Lys Phe Lys His Arg Leu His Leu Phe Phe Gly Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Arg Tyr Ile Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Leu Pro Val Gln Val Ala
            210                 215                 220

Lys Phe Lys His Gln Leu Arg Leu Thr Phe Arg Val Gly Gln Lys Thr
225                 230                 235                 240

Gln Arg Arg Trp Phe Leu Asp Lys Leu Val Asp Glu Ile Gly Val Gly
            245                 250                 255

Tyr Val Ser Asp Ser Gly Ser Val Ser Asn Tyr Glu Leu Ser Lys Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 20
<211> LENGTH: 354
<212> TYPE: PRT
<213> ORGANISM: Artificial Sequence
<220> FEATURE:
<223> OTHER INFORMATION: Synthesized

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Cys Ala Gly Ile Gln Pro Ser Gln Tyr
            20                  25                  30

Arg Lys Phe Lys His Gly Leu Trp Leu Gly Phe Tyr Val Val Gln Lys
            35                  40                  45

Thr Gln Arg Arg Trp Phe Leu Asp Lys Leu Val Asp Glu Ile Gly Val
50                  55                  60

Gly Tyr Val Tyr Asp Arg Gly Ser Val Ser Tyr Arg Leu Ser Gln
65                  70                  75                  80

Ile Lys Pro Leu His Asn Phe Leu Thr Gln Leu Gln Pro Phe Leu Lys
            85                  90                  95

Leu Lys Gln Lys Gln Ala Asn Leu Val Leu Lys Ile Ile Glu Gln Leu

```
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
                180                 185                 190
Gly Thr Gly Tyr Asn Lys Glu Phe Leu Leu Tyr Leu Ala Gly Phe Val
            195                 200                 205
Asp Gly Asp Gly Ser Ile Phe Ala Ser Ile Lys Pro Arg Gln Asn Ala
        210                 215                 220
Lys Phe Lys His Lys Leu Glu Leu Cys Phe Thr Val Gly Gln Lys Thr
225                 230                 235                 240
Gln Arg Arg Trp Phe Leu Asp Lys Leu Val Asp Glu Ile Gly Val Gly
                245                 250                 255
Tyr Val Ala Asp Leu Gly Ser Val Ser Glu Tyr Arg Leu Ser Lys Ile
                260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
        290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 21
<211> LENGTH: 354
<212> TYPE: PRT
<213> ORGANISM: Artificial Sequence
<220> FEATURE:
<223> OTHER INFORMATION: Synthesized

<400> SEQUENCE: 21

Met Asn Thr Lys Tyr Asn Lys Glu Phe Leu Leu Tyr Leu Ala Gly Phe
1               5                   10                  15
Val Asp Gly Asp Gly Ser Ile Tyr Ala Thr Ile Arg Pro Asp Gln Val
                20                  25                  30
Arg Lys Phe Lys His Gln Leu Thr Leu Tyr Phe Arg Val Ser Gln Lys
            35                  40                  45
Thr Gln Arg Arg Trp Phe Leu Asp Lys Leu Val Asp Glu Ile Gly Val
        50                  55                  60
Gly Tyr Val Asn Asp Cys Gly Ser Val Ser His Tyr Ser Leu Ser Gln
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
```

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Tyr Leu Ala Gly Phe Val
            195                 200                 205

Asp Gly Asp Gly Ser Ile Tyr Ala Thr Ile Glu Pro Ser Gln Gly Tyr
210                 215                 220

Lys Phe Lys His Arg Leu Met Leu Arg Phe Val Thr Gln Lys Thr
225                 230                 235                 240

Gln Arg Arg Trp Phe Leu Asp Lys Leu Val Asp Glu Ile Gly Val Gly
                245                 250                 255

Tyr Val His Asp Trp Gly Ser Val Ser Ser Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 22
<211> LENGTH: 354
<212> TYPE: PRT
<213> ORGANISM: Artificial Sequence
<220> FEATURE:
<223> OTHER INFORMATION: Synthesized

<400> SEQUENCE: 22

Met Asn Thr Lys Tyr Asn Lys Glu Phe Leu Tyr Leu Ala Gly Phe
1               5                   10                  15

Val Asp Gly Asp Gly Ser Ile Tyr Ala Ser Ile Tyr Pro Arg Gln Ala
                20                  25                  30

Ala Lys Phe Lys His Ala Leu Gln Leu Gly Phe Asp Val Thr Gln Lys
            35                  40                  45

Thr Gln Arg Arg Trp Phe Leu Asp Lys Leu Val Asp Glu Ile Gly Val
        50                  55                  60

Gly His Val Tyr Asp Arg Gly Ser Val Ser Ser Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Arg Ile Arg Pro Arg Gln Ser Ser
        210                 215                 220

Lys Phe Lys His Arg Leu Thr Leu Ala Phe Thr Val Gly Gln Lys Thr
225                 230                 235                 240

Gln Arg Arg Trp Phe Leu Asp Lys Leu Val Asp Glu Ile Gly Val Gly
                245                 250                 255

Tyr Val Ala Asp Leu Gly Ser Val Ser Glu Tyr Arg Leu Ser Lys Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 23
<211> LENGTH: 354
<212> TYPE: PRT
<213> ORGANISM: Artificial Sequence
<220> FEATURE:
<223> OTHER INFORMATION: Synthesized

<400> SEQUENCE: 23

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Thr Pro Ser Gln Asn
            20                  25                  30

Ser Lys Phe Lys His Lys Leu Ser Leu Val Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
```

```
            115                 120                 125
Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                    165                 170                 175

Ser Pro Gly Ser Gly Ile Ser Glu Ala Leu Arg Ala Gly Ala Gly Ser
                    180                 185                 190

Gly Thr Gly Tyr Asn Lys Glu Phe Leu Leu Tyr Leu Ala Gly Phe Val
                    195                 200                 205

Asp Gly Asp Gly Ser Ile Phe Ala Arg Ile Arg Pro Gly Gln Arg Thr
210                 215                 220

Lys Phe Lys His Lys Leu Ala Leu His Phe Thr Val Gly Gln Lys Thr
225                 230                 235                 240

Gln Arg Arg Trp Phe Leu Asp Lys Leu Val Asp Glu Ile Gly Val Gly
                    245                 250                 255

Tyr Val Ala Asp Leu Gly Ser Val Ser Glu Tyr Arg Leu Ser Gln Ile
                    260                 265                 270

Lys Pro Leu His Asn Phe Leu Thr Gln Leu Gln Pro Phe Leu Lys Leu
                    275                 280                 285

Lys Gln Lys Gln Ala Asn Leu Val Leu Lys Ile Ile Glu Gln Leu Pro
                    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                    325                 330                 335

Glu Thr Val Arg Ala Val Leu Asp Ser Leu Ser Glu Lys Lys Lys Ser
                    340                 345                 350

Ser Pro

<210> SEQ ID NO 24
<211> LENGTH: 354
<212> TYPE: PRT
<213> ORGANISM: Artificial Sequence
<220> FEATURE:
<223> OTHER INFORMATION: Synthesized

<400> SEQUENCE: 24

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Gln Pro Arg Gln Glu
                    20                  25                  30

Ser Lys Phe Lys His Ser Leu Arg Leu Tyr Phe Asp Val Thr Gln Lys
                    35                  40                  45

Thr Gln Arg Arg Trp Phe Leu Asp Lys Leu Val Asp Glu Ile Gly Val
                    50                  55                  60

Gly Tyr Val Tyr Asp Ser Gly Ser Val Ser Lys Tyr Leu Leu Ser Gln
65                  70                  75                  80

Ile Lys Pro Leu His Asn Phe Leu Thr Gln Leu Gln Pro Phe Leu Lys
                    85                  90                  95

Leu Lys Gln Lys Gln Ala Asn Leu Val Leu Lys Ile Ile Glu Gln Leu
                    100                 105                 110

Pro Ser Ala Lys Glu Ser Pro Asp Lys Phe Leu Glu Val Cys Thr Trp
                    115                 120                 125
```

Val Asp Gln Ile Ala Ala Leu Asn Asp Ser Lys Thr Arg Lys Thr Thr
          130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
              165                 170                 175

Ser Pro Gly Ser Gly Ile Ser Glu Ala Leu Arg Ala Gly Ala Gly Ser
              180                 185                 190

Gly Thr Gly Tyr Asn Lys Glu Phe Leu Leu Tyr Leu Ala Gly Phe Val
          195                 200                 205

Asp Gly Asp Gly Ser Ile His Ala Arg Ile Lys Pro Thr Gln Gln Val
210                 215                 220

Lys Phe Lys His Val Leu Glu Leu Arg Phe Ser Val Tyr Gln Lys Thr
225                 230                 235                 240

Gln Arg Arg Trp Phe Leu Asp Lys Leu Val Asp Glu Ile Gly Val Gly
              245                 250                 255

Tyr Val Thr Asp Ser Gly Gly Val Ser Phe Tyr Thr Leu Ser Lys Ile
              260                 265                 270

Lys Pro Leu His Asn Phe Leu Thr Gln Leu Gln Pro Phe Leu Lys Leu
              275                 280                 285

Lys Gln Lys Gln Ala Asn Leu Val Leu Lys Ile Ile Glu Gln Leu Pro
          290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
              325                 330                 335

Glu Thr Val Arg Ala Val Leu Asp Ser Leu Ser Glu Lys Lys Lys Ser
          340                 345                 350

Ser Pro

<210> SEQ ID NO 25
<211> LENGTH: 354
<212> TYPE: PRT
<213> ORGANISM: Artificial Sequence
<220> FEATURE:
<223> OTHER INFORMATION: Synthesized

<400> SEQUENCE: 25

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Glu Pro Arg Gln Gln
            20                  25                  30

Ala Lys Phe Lys His Arg Leu Arg Leu Trp Phe Asp Val Thr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Lys Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Arg Ile Lys Pro Thr Gln Gln Thr
    210                 215                 220

Lys Phe Lys His Ser Leu Glu Leu Arg Phe Thr Val Thr Gln Lys Thr
225                 230                 235                 240

Gln Arg Arg Trp Phe Leu Asp Lys Leu Val Asp Glu Ile Gly Val Gly
                245                 250                 255

Tyr Val Val Asp Asp Gly Ser Val Ser Phe Tyr Thr Leu Ser Lys Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 26
<211> LENGTH: 354
<212> TYPE: PRT
<213> ORGANISM: Artificial Sequence
<220> FEATURE:
<223> OTHER INFORMATION: Synthesized

<400> SEQUENCE: 26

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Glu Pro Arg Gln Gln
                20                  25                  30

Ala Lys Phe Lys His Arg Leu Arg Leu Trp Phe Asp Val Thr Gln Lys
            35                  40                  45

Thr Gln Arg Arg Trp Phe Leu Asp Lys Leu Val Asp Glu Ile Gly Val
    50                  55                  60

Gly Tyr Val Tyr Asp Leu Gly Ser Val Ser Arg Tyr Ser Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
```

```
                130                 135                 140
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Arg Ile Arg Pro Ile Gln Val Ser
            210                 215                 220

Lys Phe Lys His Asn Leu Ser Leu His Phe Thr Val His Gln Lys Thr
225                 230                 235                 240

Gln Arg Arg Trp Phe Leu Asp Lys Leu Val Asp Glu Ile Gly Val Gly
                245                 250                 255

Tyr Val Val Asp Asp Gly Ser Val Ser Thr Tyr Thr Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 27
<211> LENGTH: 354
<212> TYPE: PRT
<213> ORGANISM: Artificial Sequence
<220> FEATURE:
<223> OTHER INFORMATION: Synthesized

<400> SEQUENCE: 27

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Gln Pro Arg Gln Glu
                20                  25                  30

Ser Lys Phe Lys His Ser Leu Arg Leu Tyr Phe Asp Val Thr Gln Lys
            35                  40                  45

Thr Gln Arg Arg Trp Phe Leu Asp Lys Leu Val Asp Glu Ile Gly Val
50                  55                  60

Gly Tyr Val Tyr Asp Ser Gly Ser Val Ser Lys Tyr Leu Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
130                 135                 140
```

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Arg Ile Lys Pro Cys Gln Gln Val
            210                 215                 220

Lys Phe Lys His Thr Leu Ser Leu His Phe Thr Val Phe Gln Lys Thr
225                 230                 235                 240

Gln Arg Arg Trp Phe Leu Asp Lys Leu Val Asp Glu Ile Gly Val Gly
                245                 250                 255

Tyr Val Cys Asp Ser Gly Ser Val Ser Ser Tyr Val Leu Ser Lys Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 28
<211> LENGTH: 147
<212> TYPE: PRT
<213> ORGANISM: Artificial Sequence
<220> FEATURE:
<223> OTHER INFORMATION: Synthesized

<400> SEQUENCE: 28

Lys Glu Phe Leu Leu Tyr Leu Ala Gly Phe Val Asp Gly Asp Gly Ser
1               5                   10                  15

Ile Tyr Ala Thr Ile Asn Pro Val Gln Trp Asn Lys Phe Lys His Gln
            20                  25                  30

Leu Arg Leu Thr Phe Ala Val Thr Gln Lys Thr Gln Arg Arg Trp Phe
        35                  40                  45

Leu Asp Lys Leu Val Asp Glu Ile Gly Val Gly Tyr Val Ser Asp Trp
    50                  55                  60

Gly Ser Val Ser Gln Tyr Lys Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140
```

Val Leu Asp
145

<210> SEQ ID NO 29
<211> LENGTH: 147
<212> TYPE: PRT
<213> ORGANISM: Artificial Sequence
<220> FEATURE:
<223> OTHER INFORMATION: Synthesized

<400> SEQUENCE: 29

Lys Glu Phe Leu Leu Tyr Leu Ala Gly Phe Val Asp Gly Asp Gly Ser
1               5                   10                  15

Ile Phe Ala Thr Ile Asp Pro Glu Gln Thr Gly Lys Phe Lys His Lys
            20                  25                  30

Leu Arg Leu Arg Phe Val Val Thr Gln Lys Thr Gln Arg Arg Trp Phe
        35                  40                  45

Leu Asp Lys Leu Val Asp Glu Ile Gly Val Gly Tyr Val Thr Asp Trp
    50                  55                  60

Gly Ser Val Ser Tyr Tyr Arg Leu Ser Glu Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 30
<211> LENGTH: 147
<212> TYPE: PRT
<213> ORGANISM: Artificial Sequence
<220> FEATURE:
<223> OTHER INFORMATION: Synthesized

<400> SEQUENCE: 30

Lys Glu Phe Leu Leu Tyr Leu Ala Gly Phe Val Asp Gly Asp Gly Ser
1               5                   10                  15

Ile Phe Ala Ser Ile Glu Pro Ile Gln Tyr Ser Lys Phe Lys His Arg
            20                  25                  30

Leu Lys Leu Tyr Phe Ala Val Ser Gln Lys Thr Gln Arg Arg Trp Phe
        35                  40                  45

Leu Asp Lys Leu Val Asp Glu Ile Gly Val Gly Tyr Val Thr Asp His
    50                  55                  60

Gly Ser Val Ser Thr Tyr Arg Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

```
Val Leu Asp
145

<210> SEQ ID NO 31
<211> LENGTH: 147
<212> TYPE: PRT
<213> ORGANISM: Artificial Sequence
<220> FEATURE:
<223> OTHER INFORMATION: Synthesized

<400> SEQUENCE: 31

Lys Glu Phe Leu Leu Tyr Leu Ala Gly Phe Val Asp Gly Asp Gly Ser
1               5                   10                  15

Ile Tyr Ala Ala Ile Glu Pro Thr Gln Cys Ala Lys Phe Lys His Lys
            20                  25                  30

Leu Arg Leu Phe Ala Val Thr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Thr Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 32
<211> LENGTH: 147
<212> TYPE: PRT
<213> ORGANISM: Artificial Sequence
<220> FEATURE:
<223> OTHER INFORMATION: Synthesized

<400> SEQUENCE: 32

Lys Glu Phe Leu Leu Tyr Leu Ala Gly Phe Val Asp Gly Asp Gly Ser
1               5                   10                  15

Ile Phe Ala Thr Ile Gln Pro Ser Gln His Arg Lys Phe Lys His Gln
            20                  25                  30

Leu Val Leu Trp Phe Arg Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Tyr Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
```

```
            130                 135                 140
Val Leu Asp
145

<210> SEQ ID NO 33
<211> LENGTH: 147
<212> TYPE: PRT
<213> ORGANISM: Artificial Sequence
<220> FEATURE:
<223> OTHER INFORMATION: Synthesized

<400> SEQUENCE: 33

Lys Glu Phe Leu Leu Tyr Leu Ala Gly Phe Val Asp Gly Asp Gly Ser
1               5                   10                  15

Ile Tyr Ala Thr Ile Arg Pro Asp Gln Val Arg Lys Phe Lys His Gln
            20                  25                  30

Leu Thr Leu Tyr Phe Arg Val Ser Gln Lys Thr Gln Arg Arg Trp Phe
        35                  40                  45

Leu Asp Lys Leu Val Asp Glu Ile Gly Val Gly Tyr Val Asn Asp Cys
    50                  55                  60

Gly Ser Val Ser His Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 34
<211> LENGTH: 147
<212> TYPE: PRT
<213> ORGANISM: Artificial Sequence
<220> FEATURE:
<223> OTHER INFORMATION: Synthesized

<400> SEQUENCE: 34

Lys Glu Phe Leu Leu Tyr Leu Ala Gly Phe Val Asp Gly Asp Gly Ser
1               5                   10                  15

Ile Phe Ala Thr Ile Gln Pro Ser Gln His Arg Lys Phe Lys His Gln
            20                  25                  30

Leu Val Leu Trp Phe Arg Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Tyr Tyr Ser Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

```
Leu Asn Asp Ser Lys Thr Arg Lys Thr Thr Ser Glu Thr Val Arg Ala
    130                 135                 140

Val Leu Asp
145

<210> SEQ ID NO 35
<211> LENGTH: 147
<212> TYPE: PRT
<213> ORGANISM: Artificial Sequence
<220> FEATURE:
<223> OTHER INFORMATION: Synthesized

<400> SEQUENCE: 35

Lys Glu Phe Leu Leu Tyr Leu Ala Gly Phe Val Asp Gly Asp Gly Ser
1               5                   10                  15

Ile Tyr Ala Thr Ile Gln Pro Gly Gln Thr Arg Lys Phe Lys His Gln
            20                  25                  30

Leu Ser Leu Trp Phe Arg Val Thr Gln Lys Thr Gln Arg Arg Trp Phe
        35                  40                  45

Leu Asp Lys Leu Val Asp Glu Ile Gly Val Gly Tyr Val Ser Asp Ala
    50                  55                  60

Gly Ser Val Ser His Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 36
<211> LENGTH: 147
<212> TYPE: PRT
<213> ORGANISM: Artificial Sequence
<220> FEATURE:
<223> OTHER INFORMATION: Synthesized

<400> SEQUENCE: 36

Lys Glu Phe Leu Leu Tyr Leu Ala Gly Phe Val Asp Gly Asp Gly Ser
1               5                   10                  15

Ile His Ala Thr Ile Val Pro Ser Gln Gln Tyr Lys Phe Lys His Arg
            20                  25                  30

Leu His Leu Phe Phe Gly Val Tyr Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Arg Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
            130                 135                 140

Val Leu Asp
145

<210> SEQ ID NO 37
<211> LENGTH: 147
<212> TYPE: PRT
<213> ORGANISM: Artificial Sequence
<220> FEATURE:
<223> OTHER INFORMATION: Synthesized

<400> SEQUENCE: 37

Lys Glu Phe Leu Leu Tyr Leu Ala Gly Phe Val Asp Gly Asp Gly Ser
1               5                   10                  15

Ile His Ala Thr Ile Val Pro Ser Gln Gln Tyr Lys Phe Lys His Arg
            20                  25                  30

Leu His Leu Phe Phe Gly Val Tyr Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Arg Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 38
<211> LENGTH: 147
<212> TYPE: PRT
<213> ORGANISM: Artificial Sequence
<220> FEATURE:
<223> OTHER INFORMATION: Synthesized

<400> SEQUENCE: 38

Lys Glu Phe Leu Leu Tyr Leu Ala Gly Phe Val Asp Gly Asp Gly Ser
1               5                   10                  15

Ile His Ala Thr Ile Val Pro Ser Gln Gln Tyr Lys Phe Lys His Arg
            20                  25                  30

Leu His Leu Phe Phe Gly Val Tyr Gln Lys Thr Gln Arg Arg Trp Phe
        35                  40                  45

Leu Asp Lys Leu Val Asp Glu Ile Gly Ala Gly Tyr Val Tyr Asp Gly
    50                  55                  60

Gly Ser Val Ser Arg Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

-continued

```
                115                 120                 125

Leu Asn Asp Ser Lys Thr Arg Lys Thr Thr Ser Glu Thr Val Arg Ala
    130                 135                 140

Val Leu Asp
145

<210> SEQ ID NO 39
<211> LENGTH: 147
<212> TYPE: PRT
<213> ORGANISM: Artificial Sequence
<220> FEATURE:
<223> OTHER INFORMATION: Synthesized

<400> SEQUENCE: 39

Lys Glu Phe Leu Leu Tyr Leu Ala Gly Phe Val Asp Gly Asp Gly Ser
1               5                   10                  15

Ile His Ala Thr Ile Val Pro Ser Gln Gln Tyr Lys Phe Lys His Arg
                20                  25                  30

Leu His Leu Phe Phe Gly Val Tyr Gln Lys Thr Gln Arg Arg Trp Phe
            35                  40                  45

Leu Asp Lys Leu Val Asp Glu Ile Gly Val Gly Tyr Val Tyr Asp Gly
        50                  55                  60

Gly Ser Val Ser Arg Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 40
<211> LENGTH: 147
<212> TYPE: PRT
<213> ORGANISM: Artificial Sequence
<220> FEATURE:
<223> OTHER INFORMATION: Synthesized

<400> SEQUENCE: 40

Lys Glu Phe Leu Leu Tyr Leu Ala Gly Phe Val Asp Gly Asp Gly Ser
1               5                   10                  15

Ile Tyr Ala Arg Ile Leu Pro Val Gln Val Ala Lys Phe Lys His Gln
                20                  25                  30

Leu Arg Leu Thr Phe Arg Val Gly Gln Lys Thr Gln Arg Arg Trp Phe
            35                  40                  45

Leu Asp Lys Leu Val Asp Glu Ile Gly Val Gly Tyr Val Ser Asp Ser
        50                  55                  60

Gly Ser Val Ser Asn Tyr Glu Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110
```

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
        130                 135                 140

Val Leu Asp
145

<210> SEQ ID NO 41
<211> LENGTH: 147
<212> TYPE: PRT
<213> ORGANISM: Artificial Sequence
<220> FEATURE:
<223> OTHER INFORMATION: Synthesized

<400> SEQUENCE: 41

Lys Glu Phe Leu Leu Tyr Leu Ala Gly Phe Val Asp Gly Asp Gly Ser
1               5                   10                  15

Ile Tyr Ala Arg Ile Gly Pro Gly Gln Thr Tyr Lys Phe Lys His Gln
            20                  25                  30

Leu Lys Leu Thr Phe Ser Val Ser Gln Lys Thr Gln Arg Arg Trp Phe
        35                  40                  45

Leu Asp Lys Leu Val Asp Glu Ile Gly Val Gly Tyr Val Glu Asp Phe
    50                  55                  60

Gly Ser Val Ser Lys Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 42
<211> LENGTH: 147
<212> TYPE: PRT
<213> ORGANISM: Artificial Sequence
<220> FEATURE:
<223> OTHER INFORMATION: Synthesized

<400> SEQUENCE: 42

Lys Glu Phe Leu Leu Tyr Leu Ala Gly Phe Val Asp Gly Asp Gly Ser
1               5                   10                  15

Ile Tyr Ala Arg Ile Gly Pro Gly Gln Thr Tyr Lys Phe Lys His Gln
            20                  25                  30

Leu Lys Leu Thr Phe Ser Val Ser Gln Lys Thr Gln Arg Arg Trp Phe
        35                  40                  45

Leu Asp Lys Leu Val Asp Glu Ile Gly Val Gly Tyr Val Glu Asp Phe
    50                  55                  60

Gly Ser Val Ser Lys Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 43
<211> LENGTH: 147
<212> TYPE: PRT
<213> ORGANISM: Artificial Sequence
<220> FEATURE:
<223> OTHER INFORMATION: Synthesized

<400> SEQUENCE: 43

Lys Glu Phe Leu Leu Tyr Leu Ala Gly Phe Val Asp Gly Asp Gly Ser
1               5                   10                  15

Ile Tyr Ala Arg Ile Leu Pro Val Gln Val Ala Lys Phe Lys His Gln
            20                  25                  30

Leu Arg Leu Thr Phe Arg Val Gly Gln Lys Thr Gln Arg Arg Trp Phe
        35                  40                  45

Leu Asp Lys Leu Val Asp Glu Ile Gly Val Gly Tyr Val Ser Asp Ser
    50                  55                  60

Gly Ser Val Ser Asn Tyr Glu Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 44
<211> LENGTH: 147
<212> TYPE: PRT
<213> ORGANISM: Artificial Sequence
<220> FEATURE:
<223> OTHER INFORMATION: Synthesized

<400> SEQUENCE: 44

Lys Glu Phe Leu Leu Tyr Leu Ala Gly Phe Val Asp Gly Asp Gly Ser
1               5                   10                  15

Ile Cys Ala Gly Ile Gln Pro Ser Gln Tyr Arg Lys Phe Lys His Gly
            20                  25                  30

Leu Trp Leu Gly Phe Tyr Val Val Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Ala Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
```

```
                    100                 105                 110
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 45
<211> LENGTH: 147
<212> TYPE: PRT
<213> ORGANISM: Artificial Sequence
<220> FEATURE:
<223> OTHER INFORMATION: Synthesized

<400> SEQUENCE: 45

Lys Glu Phe Leu Leu Tyr Leu Ala Gly Phe Val Asp Gly Asp Gly Ser
1               5                   10                  15

Ile Tyr Ala Thr Ile Arg Pro Asp Gln Val Arg Lys Phe Lys His Gln
            20                  25                  30

Leu Thr Leu Tyr Phe Arg Val Ser Gln Lys Thr Gln Arg Arg Trp Phe
        35                  40                  45

Leu Asp Lys Leu Val Asp Glu Ile Gly Val Gly Tyr Val Asn Asp Cys
    50                  55                  60

Gly Ser Val Ser His Tyr Ser Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 46
<211> LENGTH: 147
<212> TYPE: PRT
<213> ORGANISM: Artificial Sequence
<220> FEATURE:
<223> OTHER INFORMATION: Synthesized

<400> SEQUENCE: 46

Lys Glu Phe Leu Leu Tyr Leu Ala Gly Phe Val Asp Gly Asp Gly Ser
1               5                   10                  15

Ile Tyr Ala Ser Ile Tyr Pro Arg Gln Ala Ala Lys Phe Lys His Ala
            20                  25                  30

Leu Gln Leu Gly Phe Asp Val Thr Gln Lys Thr Gln Arg Arg Trp Phe
        35                  40                  45

Leu Asp Lys Leu Val Asp Glu Ile Gly Val Gly His Val Tyr Asp Arg
    50                  55                  60

Gly Ser Val Ser Ser Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95
```

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 47
<211> LENGTH: 147
<212> TYPE: PRT
<213> ORGANISM: Artificial Sequence
<220> FEATURE:
<223> OTHER INFORMATION: Synthesized

<400> SEQUENCE: 47

Lys Glu Phe Leu Leu Tyr Leu Ala Gly Phe Val Asp Gly Asp Gly Ser
1               5                   10                  15

Ile Tyr Ala Thr Ile Thr Pro Ser Gln Asn Ser Lys Phe Lys His Lys
            20                  25                  30

Leu Ser Leu Val Phe Asn Val Ser Gln Lys Thr Gln Arg Arg Trp Phe
        35                  40                  45

Leu Asp Lys Leu Val Asp Glu Ile Gly Val Gly Tyr Val Arg Asp Arg
    50                  55                  60

Gly Ser Val Ser Asp Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 48
<211> LENGTH: 147
<212> TYPE: PRT
<213> ORGANISM: Artificial Sequence
<220> FEATURE:
<223> OTHER INFORMATION: Synthesized

<400> SEQUENCE: 48

Lys Glu Phe Leu Leu Tyr Leu Ala Gly Phe Val Asp Gly Asp Gly Ser
1               5                   10                  15

Ile Phe Ala Ser Ile Lys Pro Arg Gln Asn Ala Lys Phe Lys His Lys
            20                  25                  30

Leu Glu Leu Cys Phe Thr Val Gly Gln Lys Thr Gln Arg Arg Trp Phe
        35                  40                  45

Leu Asp Lys Leu Val Asp Glu Ile Gly Val Gly Tyr Val Ala Asp Leu
    50                  55                  60

Gly Ser Val Ser Glu Tyr Arg Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 49
<211> LENGTH: 147
<212> TYPE: PRT
<213> ORGANISM: Artificial Sequence
<220> FEATURE:
<223> OTHER INFORMATION: Synthesized

<400> SEQUENCE: 49

Lys Glu Phe Leu Leu Tyr Leu Ala Gly Phe Val Asp Gly Asp Gly Ser
1               5                   10                  15

Ile Tyr Ala Thr Ile Glu Pro Ser Gln Gly Tyr Lys Phe Lys His Arg
            20                  25                  30

Leu Met Leu Arg Phe Val Thr Gln Lys Thr Gln Arg Arg Trp Phe
        35                  40                  45

Leu Asp Lys Leu Val Asp Glu Ile Gly Val Gly Tyr Val His Asp Trp
    50                  55                  60

Gly Ser Val Ser Ser Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 50
<211> LENGTH: 147
<212> TYPE: PRT
<213> ORGANISM: Artificial Sequence
<220> FEATURE:
<223> OTHER INFORMATION: Synthesized

<400> SEQUENCE: 50

Lys Glu Phe Leu Leu Tyr Leu Ala Gly Phe Val Asp Gly Asp Gly Ser
1               5                   10                  15

Ile Phe Ala Arg Ile Arg Pro Arg Gln Ser Ser Lys Phe Lys His Arg
            20                  25                  30

Leu Thr Leu Ala Phe Thr Val Gly Gln Lys Thr Gln Arg Arg Trp Phe
        35                  40                  45

Leu Asp Lys Leu Val Asp Glu Ile Gly Val Gly Tyr Val Ala Asp Leu
    50                  55                  60

Gly Ser Val Ser Glu Tyr Arg Leu Ser Lys Ile Lys Pro Leu His Asn
65                  70                  75                  80

Phe Leu Thr Gln Leu Gln Pro Phe Leu Lys Leu Lys Gln Lys Gln Ala
```

```
            85                  90                  95
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 51
<211> LENGTH: 147
<212> TYPE: PRT
<213> ORGANISM: Artificial Sequence
<220> FEATURE:
<223> OTHER INFORMATION: Synthesized

<400> SEQUENCE: 51

Lys Glu Phe Leu Leu Tyr Leu Ala Gly Phe Val Asp Gly Asp Gly Ser
1               5                   10                  15

Ile Phe Ala Arg Ile Arg Pro Gly Gln Arg Thr Lys Phe Lys His Lys
            20                  25                  30

Leu Ala Leu His Phe Thr Val Gly Gln Lys Thr Gln Arg Arg Trp Phe
        35                  40                  45

Leu Asp Lys Leu Val Asp Glu Ile Gly Val Gly Tyr Val Ala Asp Leu
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 52
<211> LENGTH: 147
<212> TYPE: PRT
<213> ORGANISM: Artificial Sequence
<220> FEATURE:
<223> OTHER INFORMATION: Synthesized

<400> SEQUENCE: 52

Lys Glu Phe Leu Leu Tyr Leu Ala Gly Phe Val Asp Gly Asp Gly Ser
1               5                   10                  15

Ile Tyr Ala Thr Ile Gln Pro Arg Gln Glu Ser Lys Phe Lys His Ser
            20                  25                  30

Leu Arg Leu Tyr Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Lys Tyr Leu Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 53
<211> LENGTH: 147
<212> TYPE: PRT
<213> ORGANISM: Artificial Sequence
<220> FEATURE:
<223> OTHER INFORMATION: Synthesized

<400> SEQUENCE: 53

Lys Glu Phe Leu Leu Tyr Leu Ala Gly Phe Val Asp Gly Asp Gly Ser
1               5                   10                  15

Ile Phe Ala Thr Ile Glu Pro Arg Gln Gln Ala Lys Phe Lys His Arg
            20                  25                  30

Leu Arg Leu Trp Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Lys Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 54
<211> LENGTH: 147
<212> TYPE: PRT
<213> ORGANISM: Artificial Sequence
<220> FEATURE:
<223> OTHER INFORMATION: Synthesized

<400> SEQUENCE: 54

Lys Glu Phe Leu Leu Tyr Leu Ala Gly Phe Val Asp Gly Asp Gly Ser
1               5                   10                  15

Ile Tyr Ala Thr Ile Glu Pro Arg Gln Gln Ala Lys Phe Lys His Arg
            20                  25                  30

Leu Arg Leu Trp Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Leu
    50                  55                  60

Gly Ser Val Ser Arg Tyr Ser Leu Ser Glu Ile Lys Pro Leu His Asn
65                  70                  75                  80
```

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 55
<211> LENGTH: 147
<212> TYPE: PRT
<213> ORGANISM: Artificial Sequence
<220> FEATURE:
<223> OTHER INFORMATION: Synthesized

<400> SEQUENCE: 55

Lys Glu Phe Leu Leu Tyr Leu Ala Gly Phe Val Asp Gly Asp Gly Ser
1               5                   10                  15

Ile Tyr Ala Thr Ile Gln Pro Arg Gln Glu Ser Lys Phe Lys His Ser
            20                  25                  30

Leu Arg Leu Tyr Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Lys Tyr Leu Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 56
<211> LENGTH: 147
<212> TYPE: PRT
<213> ORGANISM: Artificial Sequence
<220> FEATURE:
<223> OTHER INFORMATION: Synthesized

<400> SEQUENCE: 56

Lys Glu Phe Leu Leu Tyr Leu Ala Gly Phe Val Asp Gly Asp Gly Ser
1               5                   10                  15

Ile His Ala Arg Ile Lys Pro Thr Gln Gln Val Lys Phe Lys His Val
            20                  25                  30

Leu Glu Leu Arg Phe Ser Val Tyr Gln Lys Thr Gln Arg Arg Trp Phe
        35                  40                  45

Leu Asp Lys Leu Val Asp Glu Ile Gly Val Gly Tyr Val Thr Asp Ser
    50                  55                  60

Gly Gly Val Ser Phe Tyr Thr Leu Ser Lys Ile Lys Pro Leu His Asn

```
                65                  70                  75                  80
Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                    100                 105                 110

Pro Asp Lys Phe Leu Glu Val Cys Thr Trp Val Asp Gln Ile Ala Ala
                    115                 120                 125

Leu Asn Asp Ser Lys Thr Arg Lys Thr Thr Ser Glu Thr Val Arg Ala
                    130                 135                 140

Val Leu Asp
145

<210> SEQ ID NO 57
<211> LENGTH: 147
<212> TYPE: PRT
<213> ORGANISM: Artificial Sequence
<220> FEATURE:
<223> OTHER INFORMATION: Synthesized

<400> SEQUENCE: 57

Lys Glu Phe Leu Leu Tyr Leu Ala Gly Phe Val Asp Gly Asp Gly Ser
1               5                   10                  15

Ile Tyr Ala Arg Ile Lys Pro Thr Gln Gln Thr Lys Phe Lys His Ser
                20                  25                  30

Leu Glu Leu Arg Phe Thr Val Thr Gln Lys Thr Gln Arg Arg Trp Phe
            35                  40                  45

Leu Asp Lys Leu Val Asp Glu Ile Gly Val Gly Tyr Val Val Asp Asp
        50                  55                  60

Gly Ser Val Ser Phe Tyr Thr Leu Ser Lys Ile Lys Pro Leu His Asn
65                  70                  75                  80

Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                    100                 105                 110

Pro Asp Lys Phe Leu Glu Val Cys Thr Trp Val Asp Gln Ile Ala Ala
                    115                 120                 125

Leu Asn Asp Ser Lys Thr Arg Lys Thr Thr Ser Glu Thr Val Arg Ala
                    130                 135                 140

Val Leu Asp
145

<210> SEQ ID NO 58
<211> LENGTH: 147
<212> TYPE: PRT
<213> ORGANISM: Artificial Sequence
<220> FEATURE:
<223> OTHER INFORMATION: Synthesized

<400> SEQUENCE: 58

Lys Glu Phe Leu Leu Tyr Leu Ala Gly Phe Val Asp Gly Asp Gly Ser
1               5                   10                  15

Ile Phe Ala Arg Ile Arg Pro Ile Gln Val Ser Lys Phe Lys His Asn
                20                  25                  30

Leu Ser Leu His Phe Thr Val His Gln Lys Thr Gln Arg Arg Trp Phe
            35                  40                  45

Leu Asp Lys Leu Val Asp Glu Ile Gly Val Gly Tyr Val Val Asp Asp
        50                  55                  60
```

Gly Ser Val Ser Thr Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 59
<211> LENGTH: 147
<212> TYPE: PRT
<213> ORGANISM: Artificial Sequence
<220> FEATURE:
<223> OTHER INFORMATION: Synthesized

<400> SEQUENCE: 59

Lys Glu Phe Leu Leu Tyr Leu Ala Gly Phe Val Asp Gly Asp Gly Ser
1               5                   10                  15

Ile Phe Ala Arg Ile Lys Pro Cys Gln Gln Val Lys Phe Lys His Thr
            20                  25                  30

Leu Ser Leu His Phe Thr Val Phe Gln Lys Thr Gln Arg Arg Trp Phe
        35                  40                  45

Leu Asp Lys Leu Val Asp Glu Ile Gly Val Gly Tyr Val Cys Asp Ser
    50                  55                  60

Gly Ser Val Ser Ser Tyr Val Leu Ser Lys Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 60
<211> LENGTH: 2847
<212> TYPE: DNA
<213> ORGANISM: Artificial Sequence
<220> FEATURE:
<223> OTHER INFORMATION: Synthesized

<400> SEQUENCE: 60
tagcactcta tcacggccat attctggcag ggtcagtggc tccaactaac atttgtttgg      60
tactttacag tttattaaat agatgtttat atggagaagc tctcattct ttctcagaag     120 agcctggcta ggaaggtgga tgaggcacca tattcatttt gcaggtgaaa ttcctgagat     180
gtaaggagct gctgtgactt gctcaaggcc ttatatcaag taaacggtag cgctggggct     240
tagacgcagg tgttctgatt tatagttcaa aacctctatc aatgagagag caatctcctg     300
gtaatgtgat agatttccca acttaatgcc aacataccat aaacctccca ttctgctaat     360

```
gcccagccta agttggggag accactccag attccaagat gtacagtttg ctttgctggg    420
cctttttccc atgcctgcct ttactctgcc agagttatat tgctggggtt ttgaagaaga    480
tcctattaaa taaaagaata agcagtatta ttaagtagcc ctgcatttca ggtttccttg    540
agtggcaggc caggcctggc cgtgaacgtt cactgaaatc atggcctctt ggccaagatt    600
gatagcttgt gccttgtcga gacagagaag actcttgcgt ttctgatagg cacctattgg    660
tcttactgac atccactttg cctttctctc cacaggcggc ggtggcgagg cagaggaag    720 tcttctaaca tgcggtgacg tggaggagaa tcccggccct atggcgctcc cagtgacagc    780
cttactttta cctctggcgt tattattgca cgcggctcgt cctgacatac agatgactca    840
gactacctct tccctatctg cttctttagg cgaccgagta acaatatctt gccgggccag    900
ccaggacatc tcaaaatact taaactggta tcagcagaag ccggacggaa cagttaagtt    960
gctcatttac cacacgtcga gattacactc aggcgttcct agccgatttt cgggttccgg   1020
ttccggtacg gactacagcc tgacaatcag taaccttgag caggaggaca tcgccaccta   1080
cttctgtcag cagggcaaca cgctcccgta cacattcggt gggggaacta agctggagat   1140
taccggaggc ggtggcagcg gtggcggcgg cagcgggggt ggcggctcgg aggtcaagtt   1200
acaggagagc ggaccgggct tggtcgcacc tagccagagc ctctcagtca cgtgcactgt   1260
gtctggagtc agtctcccag actacggggt atcatggata cgacagccgc ctagaaaggg   1320
cttagagtgg ctgggggtta tctggggaag tgaaaccaca tactacaact cagctctcaa   1380
gagccgcctc accatcatta aggacaacag taagtcgcag gtttttcttaa agatgaactc   1440 tctccagact gacgacaccg ctatttacta ctgcgcgaag cactactact acggcgggag   1500
ttacgcaatg gactactggg gtcagggcac ttctgtgacc gtatccagca ctactacccc   1560
agccccacgt ccccccacgc cagctccaac gatagcaagt cagcccttat ctcttcgccc   1620
tgaggcttgc aggcccgcgg cgggcggcgc cgttcacacg cgaggactag acttcgcctg   1680
cgacatctac atctgggcac cactagccgg gacttgcgga gtgttgttgt tgagcttggt   1740
aataacgctc tactgcaaag cgagccgcaa aaaagcggcg gcggcggcga aaagcccgtt   1800
tgcgagcccg gcgagcagcg cgcaggaaga agatgccgag agctgccgcg cgccgagcga   1860
agaagaaggc agctgcgaac tgagagtgaa gttctctcgc tccgcggacg caccgctta    1920 ccagcagggt cagaaccagc tatacaacga gttaaacctg gggcgccggg aggagtacga   1980
cgtgttagac aagcgtagag gtagggaccc ggagatggga ggcaagcctc ggagaaagaa   2040
cccccaggag ggcctgtaca acgaactcca gaaggacaag atggctgagg cgtactcgga   2100
gattggtatg aagggcgaga gacgtcgcgg aaagggacac gacggcttat accagggct   2160 ttccaccgcg accaaggaca catacgacgc gctgcacatg caagccttac cacctcgatg   2220
aggtaccagc ggccgcgatc cagacatgat aagatacatt gatgagttg acaaaccac    2280 aactagaatg cagtgaaaaa aatgctttat ttgtgaaatt tgtgatgcta ttgctttatt   2340
tgtaaccatt ataagctgca ataaacaagt taacaacaac aattgcattc attttatgtt   2400
tcaggttcag ggggaggtgt gggaggtttt ttaaagcaag taagtgcctg tccctgagtc   2460
ccagtccatc acgagcagct ggtttctaag atgctatttc ccgtataaag catgagaccg   2520
tgacttgcca gccccacaga gccccgccct tgtccatcac tggcatctgg actccagcct   2580
gggttggggc aaagagggaa atgagatcat gtcctaaccc tgatcctctt gtcccacaga   2640
tatccagaac cctgaccctg ccgtgtacca gctgagagac tctaaatcca gtgacaagtc   2700
```

-continued

| | |
|---|---|
| tgtctgccta ttcaccgatt ttgattctca aacaaatgtg tcacaaagta aggattctga | 2760 |
| tgtgtatatc acagacaaaa ctgtgctaga catgaggtct atggacttca agagcaacag | 2820 |
| tgctgtggcc tggagcaaca aatctga | 2847 |

<210> SEQ ID NO 61
<211> LENGTH: 2847
<212> TYPE: DNA
<213> ORGANISM: Artificial Sequence
<220> FEATURE:
<223> OTHER INFORMATION: Synthesized

<400> SEQUENCE: 61

| | |
|---|---|
| catgctaatc ctccggcaaa cctctgtttc ctcctcaaaa ggcaggaggt cggaaagaat | 60 |
| aaacaatgag agtcacatta aaaacacaaa atcctacgga aatactgaag aatgagtctc | 120 |
| agcactaagg aaaagcctcc agcagctcct gctttctgag ggtgaaggat agacgctgtg | 180 |
| gctctgcatg actcactagc actctatcac ggccatattc tggcagggtc agtggctcca | 240 |
| actaacattt gtttggtact ttacagttta ttaaatagat gttatatgg agaagctctc | 300 |
| atttcttcct cagaagagcc tggctaggaa ggtggatgag gcaccatatt cattttgcag | 360 |
| gtgaaattcc tgagatgtaa ggagctgctg tgacttgctc aaggccttat atcaagtaaa | 420 |
| cggtagcgct ggggcttaga cgcaggtgtt ctgatttata gttcaaaacc tctatcaatg | 480 |
| agagagcaat ctcctggtaa tgtgatagat ttcccaactt aatgccaaca taccataaac | 540 |
| ctcccattct gctaatgccc agcctaagtt ggggagacca ctccagattc aagatgtac | 600 |
| agtttgcttt gccttgtcga gacagagaag actcttgcgt ttctgatagg cacctattgg | 660 |
| tcttactgac atccactttg cctttctctc cacaggcggc agcggcgagg cagaggaag | 720 |
| tcttctaaca tgcggtgacg tggaggagaa tcccggccct atggcgctcc cagtgacagc | 780 |
| cttactttta cctctggcgt tattattgca cgcggctcgt cctgacatac agatgactca | 840 |
| gactacctct tccctatctg cttctttagg cgaccgagta acaatatctt gccgggccag | 900 |
| ccaggacatc tcaaaatact aaactggta tcagcagaag ccggacggaa cagttaagtt | 960 |
| gctcatttac cacacgtcga gattacactc aggcgttcct agccgatttt cgggttccgg | 1020 |
| ttccggtacg gactacagcc tgacaatcag taaccttgag caggaggaca tcgccaccta | 1080 |
| cttctgtcag cagggcaaca cgctcccgta cacattcggt gggggaacta agctggagat | 1140 |
| taccggaggc ggtggcagcg gtggcggcgg cagcggggt ggcggctcgg aggtcaagtt | 1200 |
| acaggagagc ggaccgggct tggtcgcacc tagccagagc ctctcagtca cgtgcactgt | 1260 |
| gtctggagtc agtctcccag actacggggt atcatggata cgacagccgc ctagaaaggg | 1320 |
| cttagagtgg ctgggggtta tctggggaag tgaaaccaca tactacaact cagctctcaa | 1380 |
| gagccgcctc accatcatta aggacaacag taagtcgcag gttttcttaa agatgaactc | 1440 |
| tctccagact gacgacaccg ctatttacta ctgcgcgaag cactactact acggcgggag | 1500 |
| ttacgcaatg gactactggg gtcagggcac ttctgtgacc gtatccagca ctactacccc | 1560 |
| agccccacgt ccccccacgc cagctccaac gatagcaagt cagcccttat ctcttcgccc | 1620 |
| tgaggcttgc aggcccgcgg cgggcggcgc cgttcacacg cgaggactag acttcgcctg | 1680 |
| cgacatctac atctgggcac cactagccgg gacttgcgga gtgttgttgt tgagcttggt | 1740 |
| aataacgctc tactgcaaag cgagccgcaa aaaagcggcg gcggcggcga aaagcccgtt | 1800 |
| tgcgagcccg gcgagcagcg cgcaggaaga agatgcgagc agctgccgcg cgccgagcga | 1860 |
| agaagaaggc agctgcgaac tgagagtgaa gttctctcgc tccgcggacg cacccgctta | 1920 |

```
ccagcagggt cagaaccagc tatacaacga gttaaacctg ggcgccggg aggagtacga   1980 cgtgttagac aagcgtagag gtagggaccc ggagatggga ggcaagcctc ggagaaagaa   2040
cccccaggag ggcctgtaca acgaactcca gaaggacaag atggctgagg cgtactcgga   2100
gattggtatg aagggcgaga gacgtcgcgg aaagggacac gacggcttat accaggggct   2160
ttccaccgcg accaaggaca catacgacgc gctgcacatg caagcctyac cacctcgatg   2220
aggtaccagc ggccgcgatc cagacatgat aagatacatt gatgagtttg acaaaccac   2280 aactagaatg cagtgaaaaa aatgctttat ttgtgaaatt tgtgatgcta ttgctttatt   2340
tgtaaccatt ataagctgca ataaacaagt taacaacaac aattgcattc attttatgtt   2400
tcaggttcag ggggaggtgt gggaggtttt ttaaagcaag taattgctgg gcctttttcc   2460
catgcctgcc tttactctgc cagagttata ttgctgggt tttgaagaag atcctattaa   2520
ataaaagaat aagcagtatt attaagtagc cctgcatttc aggtttcctt gagtggcagg   2580
ccaggcctgg ccgtgaacgt tcactgaaat catggcctct tggccaagat tgatagcttg   2640
tgcctgtccc tgagtcccag tccatcacga gcagctggtt tctaagatgc tatttcccgt   2700
ataaagcatg agaccgtgac ttgccagccc cacagagccc cgcccttgtc catcactggc   2760
atctggactc cagcctgggt tggggcaaag agggaaatga gatcatgtcc taaccctgat   2820
cctcttgtcc cacagatatc cagaacc                                      2847

<210> SEQ ID NO 62
<211> LENGTH: 2229
<212> TYPE: DNA
<213> ORGANISM: Artificial Sequence
<220> FEATURE:
<223> OTHER INFORMATION: Synthesized

<400> SEQUENCE: 62
catgctaatc ctccggcaaa cctctgtttc ctcctcaaaa ggcaggaggt cggaaagaat     60
aaacaatgag agtcacatta aaacacaaa atcctacgga aatactgaag aatgagtctc    120
agcactaagg aaaagcctcc agcagctcct gctttctgag ggtgaaggat agacgctgtg    180
gctctgcatg actcactagc actctatcac ggccatattc tggcagggtc agtggctcca    240
actaacattt gtttggtact ttacagttta ttaaatagat gtttatatgg agaagctctc    300
atttctttct cagaagagcc tggctaggaa ggtggatgag gcaccatatt cattttgcag    360
gtgaaattcc tgagatgtaa ggagctgctg tgacttgcct tgtcgagaca gagaagactc    420
ttgcgttcct gataggcacc tattggtctt actgacatcc actttgcctt tctctccaca    480
ggcggcggtg gcgagggcag aggaagtctt ctaacatgcg gtgacgtgga ggagaatccc    540
ggccctatgg cgctcccagt gacagcctta cttttacctc tggcgttatt attgcacgcg    600
gctcgtcctg acatacagat gactcagact acctcttccc tatctgcttc tttaggcgac    660
cgagtaacaa tatcttgccg ggccagccag gacatctcaa aatacttaaa ctggtatcag    720
cagaagccgg acggaacagt taagttgctc atttaccaca cgtcgagatt acactcaggc    780
gttcctagcc gattttcggg ttccggttcc ggtacggact acagcctgac aatcagtaac    840
cttgagcagg aggacatcgc cacctacttc tgtcagcagg caacacgct cccgtacaca    900 ttcggtgggg gaactaagct ggagattacc ggaggcggtg gcagcggtgg cggcggcagc    960
gggggtggcg gctcggaggt caagttacag gagagcggac cgggcttggt cgcacctagc   1020
cagagcctct cagtcacgtg cactgtgtct ggagtcagtc tcccagacta cggggtatca   1080
```

```
tggatacgac agccgcctag aaagggctta gagtggctgg gggttatctg gggaagtgaa      1140
accacatact acaactcagc tctcaagagc cgcctcacca tcattaagga caacagtaag      1200
tcgcaggttt tcttaaagat gaactctctc cagactgacg acaccgctat ttactactgc      1260
gcgaagcact actactacgg cgggagttac gcaatggact actggggtca gggcacttct      1320
gtgaccgtat ccagcactac taccccagcc ccacgtcccc ccacgccagc tccaacgata      1380
gcaagtcagc cctatctctc tcgccctgag gcttgcaggc ccgcggcggg cggcgccgtt      1440
cacacgcgag gactagactt cgcctgcgac atctacatct gggcaccact agccgggact      1500
tgcggagtgt tgttgttgag cttggtaata acgctctact gcaaagcgag ccgcaaaaaa      1560
gcggcggcgg cggcgaaaag cccgtttgcg agcccggcga gcagcgcgca ggaagaagat      1620
gcgagcagct gccgcgcgcc gagcgaagaa gaaggcagct gcgaactgag agtgaagttc      1680
tctcgctccg cggacgcacc cgcttaccag cagggtcaga accagctata caacgagtta      1740
aacctggggc gccggagga gtacgacgtg ttagacaagc gtagaggtag ggacccggag      1800
atgggaggca agcctcggag aaagaacccc caggagggcc tgtacaacga actccagaag      1860
gacaagatgg ctgaggcgta ctcggagatt ggtatgaagg gcgagacg tcgcggaaag       1920
ggacacgacg gcttatacca ggggctttcc accgcgacca aggacacata cgacgcgctg      1980
cacatgcaag ccttaccacc tcgatgaggt accagcggcc gcgatccaga catgataaga      2040
tacattgatg agtttggaca aaccacaact agaatgcagt gaaaaaatg ctttatttgt       2100
gaaatttgtg atgctattgc tttatttgta accattataa gctgcaataa acaagttaac      2160
aacaacaatt gcattcattt tatgtttcag gttcaggggg aggtgtggga ggttttttaa      2220
agcaagtaa                                                              2229
```

<210> SEQ ID NO 63
<211> LENGTH: 2524
<212> TYPE: DNA
<213> ORGANISM: Artificial Sequence
<220> FEATURE:
<223> OTHER INFORMATION: Synthesized

<400> SEQUENCE: 63

```
gttggccact ccctctctgc gcgctcgctc gctcactgag gccgggcgac caaaggtcgc       60
ccgacgcccg ggctttgccc gggcggcctc agtgagcgag cgagcgcgca gagagggagt      120
ggccaactcc atcactaggg gttcctacgc gtccagcagc tcctgctttc tgagggtgaa      180
ggatagacgc tgtggctctg catgactcac tagcactcta tcacgccat attctggcag       240
ggtcagtggc tccaactaac atttgtttgg tactttacag tttattaaat agatgtttat      300
atggagaagc tctcatttct ttctcagaag agcctggcta ggaaggtgga tgaggcacca      360
tattcatttt gcaggtgaaa ttcctgagat gtaaggagct gctgtgactt gctcaaggcc      420
ttatatcaag taaacggtag cgctgggggct tagacgcagg tgttctgatt tatagttcaa      480
aacctctatc aatgagagag caatctcctg gtaatgtgat agatttccca acttaatgcc      540
aacataccat aaacctccca ttctgctaat gcccagccta agttggggag accactccag      600
attccaagat gtacagtttg ctttgctggg cctttttccc atgcctgcct ttactctgcc      660
agagttatat tgctggggtt tgaagaaga tcctattaaa taaaagaata agcagtatta       720
ttaagtagcc ctgcatttca ggtttccttg agtggcaggc caggcctggc cgtgaacgtt      780
cactgaaatc atggcctctt ggccaagatt gatagcttgt gccttgtcga cagagaag        840
actcttgcgt ttctgatagg cacctattgg tcttactgac atccactttg cctttctctc      900
```

| | | | | |
|---|---|---|---|---|
| cacaggcggc | ggtggcgagg | gcagaggaag | tcttctaaca tgcggtgacg | tggaggagaa | 960 |
| tcccggcccc | atggtgagca | agggcgagga | gctgttcacc ggggtggtgc | ccatcctggt | 1020 |
| cgagctggac | ggcgacgtaa | acggccacaa | gttcagcgtg tccggcgagg | gcagggcga | 1080 |
| tgccacctac | ggcaagctga | ccctgaagtt | catctgcacc accggcaagc | tgcccgtgcc | 1140 |
| ctggcccacc | ctcgtgacca | ccctgaccta | cggagtgcag tgcttcagcc | gctaccccga | 1200 |
| ccacatgaag | cagcacgact | tcttcaagtc | cgccatgccc gaaggctacg | tccaggagcg | 1260 |
| caccatcttc | ttcaaggacg | acggcaacta | caagacccgc gccgaggtga | agttcgaggg | 1320 |
| cgacaccctg | gtgaaccgca | tcgagctgaa | gggcatcgac ttcaaggagg | acggcaacat | 1380 |
| cctggggcac | aagctggagt | acaactacaa | cagccacaac gtctatatca | tggccgacaa | 1440 |
| gcagaagaac | ggcatcaagg | tgaacttcaa | gatccgccac aacatcgagg | acggcagcgt | 1500 |
| gcagctcgcc | gaccactacc | agcagaacac | ccccatcggc gacggccccg | tgctgctgcc | 1560 |
| cgacaaccac | tacctgagca | cccagtccgc | cctgagcaaa gacccccaacg | agaagcgcga | 1620 |
| tcacatggtc | ctgctggagt | tcgtgaccgc | cgccgggatc actctcggca | tggacgagct | 1680 |
| gtacaagtaa | cctaggtacc | gcggccgcga | tccagacatg ataagataca | ttgatgagtt | 1740 |
| tggacaaacc | acaactagaa | tgcagtgaaa | aaaatgcttt atttgtgaaa | tttgtgatgc | 1800 |
| tattgcttta | tttgtaacca | ttataagctg | caataaacaa gttaacaaca | acaattgcat | 1860 |
| tcattttatg | tttcaggttc | agggggaggt | gtgggaggtt ttttaaagca | agtaagtgcc | 1920 |
| tgtccctgag | tcccagtcca | tcacgagcag | ctggtttcta agatgctatt | tcccgtataa | 1980 |
| agcatgagac | cgtgacttgc | cagccccaca | gagccccgcc cttgtccatc | actggcatct | 2040 |
| ggactccagc | ctgggttggg | gcaaagaggg | aaatgagatc atgtcctaac | cctgatcctc | 2100 |
| ttgtcccaca | gatatccaga | accctgaccc | tgccgtgtac cagctgagag | actctaaatc | 2160 |
| cagtgacaag | tctgtctgcc | tattcaccga | ttttgattct caaacaaatg | tgtcacaaag | 2220 |
| taaggattct | gatgtgtata | tcacagacaa | aactgtgcta gacatgaggt | ctatggactt | 2280 |
| caagagcaac | agtgctgtgg | cctggagcaa | caaatctgac tttgcatgtg | caaacgcctt | 2340 |
| caacaacagc | attattccag | aagacacctt | cttccccagc ccaggtaagg | ggaattgatg | 2400 |
| gagttggcca | ctccctctct | gcgcgctcgc | tcgctcactg aggccgcccg | ggcaaagccc | 2460 |
| gggcgtcggg | cgacctttgg | tcgcccggcc | tcagtgagcg agcgagcgcg | cagagaggga | 2520 |
| gtgg | | | | | 2524 |

<210> SEQ ID NO 64
<211> LENGTH: 3262
<212> TYPE: DNA
<213> ORGANISM: Artificial Sequence
<220> FEATURE:
<223> OTHER INFORMATION: Synthesized

<400> SEQUENCE: 64

| | | | | |
|---|---|---|---|---|
| gttggccact | ccctctctgc | gcgctcgctc | gctcactgag gccgggcgac | caaaggtcgc | 60 |
| ccgacgcccg | ggctttgccc | gggcggcctc | agtgagcgag cgagcgcgca | gagagggagt | 120 |
| ggccaactcc | atcactaggg | gttcctacgc | gtccagcagc tcctgctttc | tgagggtgaa | 180 |
| ggatagacgc | tgtggctctg | catgactcac | tagcactcta tcacggccat | attctggcag | 240 |
| ggtcagtggc | tccaactaac | atttgtttgg | tactttacag tttattaaat | agatgtttat | 300 |
| atggagaagc | tctcatttct | ttctcagaag | agcctggcta ggaaggtgga | tgaggcacca | 360 |

```
tattcatttt gcaggtgaaa ttcctgagat gtaaggagct gctgtgactt gctcaaggcc      420
ttatatcaag taaacggtag cgctgggget tagacgcagg tgttctgatt tatagttcaa      480
aacctctatc aatgagagag caatctcctg gtaatgtgat agatttccca acttaatgcc      540
aacataccat aaacctccca ttctgctaat gcccagccta agttggggag accactccag      600
attccaagat gtacagtttg ctttgctggg cctttttccc atgcctgcct ttactctgcc      660
agagttatat tgctggggtt ttgaagaaga tcctattaaa taaaagaata agcagtatta      720
ttaagtagcc ctgcatttca ggtttccttg agtggcaggc caggcctggc cgtgaacgtt      780
cactgaaatc atggcctctt ggccaagatt gatagcttgt gccttgtcga cagagaag       840 actcttgcgt ttctgatagg cacctattgg tcttactgac atccactttg cctttctctc      900
cacaggcggc ggtggcgagg gcagaggaag tcttctaaca tgcggtgacg tggaggagaa      960
tcccggcccc atggcgctcc cagtgacagc cttacttta cctctggcgt tattattgca     1020
cgcggctcgt cctgacatac agatgactca gactacctct tccctatctg cttctttagg     1080
cgaccgagta acaatatctt gccgggccag ccaggacatc tcaaaatact taaactggta     1140
tcagcagaag ccggacggaa cagttaagtt gctcatttac cacacgtcga gattacactc     1200
aggcgttcct agccgatttt cgggttccgg ttccggtacg gactacagcc tgacaatcag     1260
taaccttgag caggaggaca tcgccaccta cttctgtcag cagggcaaca cgctcccgta     1320
cacattcggt gggggaacta agctggagat taccggaggc ggtggcagcg gtggcggcgg     1380
cagcgggggt ggcggctcgg aggtcaagtt acaggagagc ggaccgggct tggtcgcacc     1440
tagccagagc ctctcagtca cgtgcactgt gtctggagtc agtctcccag actacggggt     1500
atcatggata cgacagccgc ctagaaaggg cttagagtgg ctgggggtta tctggggaag     1560
tgaaaccaca tactacaact cagctctcaa gagccgcctc accatcatta aggacaacag     1620
taagtcgcag gttttcttaa agatgaactc tctccagact gacgacaccg ctatttacta     1680
ctgcgcgaag cactactact acggcgggag ttacgcaatg gactactggg gtcagggcac     1740
ttctgtgacc gtatccagca ctactacccc agccccacgt ccccccacgc cagctccaac     1800
gatagcaagt cagcccttat ctcttcgccc tgaggcttgc aggcccgcgg cgggcggcgc     1860
cgttcacacg cgaggactag acttcgcctg cgacatctac atctgggcac cactagccgg     1920
gacttgcgga gtgttgttgt tgagcttggt aataacgctc tactgcaaag cgagccgcaa     1980
aaaagcggcg gcggcggcga aaagcccgtt tgcgagcccg gcgagcagcg cgcaggaaga     2040
agatgcgagc agctgccgcg cgccgagcga agaagaaggc agctgcgaac tgagagtgaa     2100
gttctctcgc tccgcggacg caccgctta ccagcagggt cagaaccagc tatacaacga     2160
gttaaacctg gggcgccggg aggagtacga cgtgttagac aagcgtagag gtagggaccc     2220
ggagatggga ggcaagcctc ggagaaagaa ccccaggag ggcctgtaca acgaactcca     2280
gaaggacaag atggctgagg cgtactcgga gattggtatg aagggcgaga cgtcgcgg       2340 aaagggacac gacggcttat accagggget tccaccgcg accaaggaca catacgacgc      2400
gctgcacatg caagccttac cacctcgatg aggtaccagc ggccgcgatc cagacatgat     2460
aagatacatt gatgagtttg gacaaaccac aactagaatg cagtgaaaaa aatgctttat     2520
ttgtgaaatt tgtgatgcta ttgctttatt tgtaaccatt ataagctgca ataaacaagt     2580
taacaacaac aattgcattc attttatgtt tcaggttcag ggggaggtgt gggaggtttt     2640
ttaaagcaag taagtgcctg tccctgagtc ccagtccatc acgagcagct ggtttctaag     2700
atgctatttc ccgtataaag catgagaccg tgacttgcca gccccacaga gccccgccct     2760
```

```
tgtccatcac tggcatctgg actccagcct gggttggggc aaagagggaa atgagatcat    2820
gtcctaaccc tgatcctctt gtcccacaga tatccagaac cctgaccctg ccgtgtacca    2880
gctgagagac tctaaatcca gtgacaagtc tgtctgccta ttcaccgatt ttgattctca    2940
aacaaatgtg tcacaaagta aggattctga tgtgtatatc acagacaaaa ctgtgctaga    3000
catgaggtct atggacttca agagcaacag tgctgtggcc tggagcaaca atctgactt     3060 tgcatgtgca acgccttca acaacagcat tattccagaa gacaccttct tccccagccc     3120
aggtaagggg aattgatgga gttggccact ccctctctgc gcgctcgctc gctcactgag    3180
gccgcccggg caaagcccgg gcgtcgggcg acctttggtc gcccggcctc agtgagcgag    3240
cgagcgcgca gagagggagt gg                                             3262

<210> SEQ ID NO 65
<211> LENGTH: 2524
<212> TYPE: DNA
<213> ORGANISM: Artificial Sequence
<220> FEATURE:
<223> OTHER INFORMATION: Synthesized

<400> SEQUENCE: 65
gttggccact ccctctctgc gcgctcgctc gctcactgag gccgggcgac caaaggtcgc      60
ccgacgcccg ggctttgccc gggcggcctc agtgagcgag cgagcgcgca gagagggagt     120
ggccaactcc atcactaggg gttcctacgc gtccagcagc tcctgctttc tgagggtgaa     180
ggatagacgc tgtggctctg catgactcac tagcactcta tcacgccat attctggcag      240 ggtcagtggc tccaactaac atttgtttgg tactttacag tttattaaat agatgtttat     300
atggagaagc tctcatttct ttctcagaag agcctggcta ggaaggtgga tgaggcacca     360
tattcatttt gcaggtgaaa ttcctgagat gtaaggagct gctgtgactt gctcaaggcc     420
ttatatcaag taaacggtag cgctggggct tagacgcagg tgttctgatt tatagttcaa     480
aacctctatc aatgagagag caatctcctg gtaatgtgat agatttccca acttaatgcc     540
aacataccat aaacctccca ttctgctaat gcccagccta agttggggag accactccag     600
attccaagat gtacagtttg ctttgccttg tcgagacaga gaagactctt gcgtttctga     660
taggcaccta ttggtcttac tgacatccac tttgcctttc tctccacagg cggcggtggc     720
gagggcagag gaagtcttct aacatgcggt gacgtggagg agaatcccgg ccccatggtg     780
agcaagggcg aggagctgtt caccggggtg gtgcccatcc tggtcgagct ggacggcgac     840
gtaaacggcc acaagttcag cgtgtccggc gagggcgagg gcgatgccac ctacggcaag     900
ctgaccctga gttcatctg caccaccggc aagctgcccg tgccctggcc caccctcgtg     960
accaccctga cctacggagt gcagtgcttc agccgctacc ccgaccacat gaagcagcac    1020
gacttcttca gtccgccat gcccgaaggc tacgtccagg agcgcaccat cttcttcaag    1080
gacgacggca actacaagac ccgcgccgag gtgaagttcg agggcgacac cctggtgaac    1140
cgcatcgagc tgaagggcat cgacttcaag gaggacggca acatcctggg gcacaagctg    1200
gagtacaact acaacagcca caacgtctat atcatggccg acaagcagaa gaacggcatc    1260
aaggtgaact tcaagatccg ccacaacatc gaggacggca gcgtgcagct cgccgaccac    1320
taccagcaga acacccccat cggcgacggc cccgtgctgc tgcccgacaa ccactacctg    1380
agcacccagt ccgccctgag caaagacccc aacgagaagc gcgatcacat ggtcctgctg    1440
gagttcgtga ccgccgccgg gatcactctc ggcatggacg agctgtacaa gtaacctagg    1500
```

```
taccgcggcc gcgatccaga catgataaga tacattgatg agtttggaca aaccacaact    1560
agaatgcagt gaaaaaaatg ctttatttgt gaaatttgtg atgctattgc tttatttgta    1620
accattataa gctgcaataa acaagttaac aacaacaatt gcattcattt tatgtttcag    1680 gttcagggggg aggtgtggga ggttttttaa agcaagtaat tgctgggcct ttttcccatg    1740 cctgcctttaa ctctgccaga gttatattgc tggggttttg aagaagatcc tattaaataa    1800
aagaataagc agtattatta agtagccctg catttcaggt ttccttgagt ggcaggccag    1860
gcctggccgt gaacgttcac tgaaatcatg gcctcttggc caagattgat agcttgtgcc    1920
tgtccctgag tcccagtcca tcacgagcag ctggtttcta agatgctatt tcccgtataa    1980
agcatgagac cgtgacttgc cagccccaca gagccccgcc cttgtccatc actggcatct    2040
ggactccagc ctgggttggg gcaaagaggg aaatgagatc atgtcctaac cctgatcctc    2100
ttgtcccaca gatatccaga accctgaccc tgccgtgtac cagctgagag actctaaatc    2160
cagtgacaag tctgtctgcc tattcaccga ttttgattct caaacaaatg tgtcacaaag    2220
taaggattct gatgtgtata tcacagacaa aactgtgcta gacatgaggt ctatggactt    2280
caagagcaac agtgctgtgg cctggagcaa caaatctgac tttgcatgtg caaacgcctt    2340
caacaacagc attattccag aagacacctt cttccccagc ccaggtaagg ggaattgatg    2400
gagttggcca ctccctctct gcgcgctcgc tcgctcactg aggccgcccg ggcaaagccc    2460
gggcgtcggg cgacctttgg tcgcccggcc tcagtgagcg agcgagcgcg cagagaggga    2520
gtgg    2524
```

<210> SEQ ID NO 66
<211> LENGTH: 3262
<212> TYPE: DNA
<213> ORGANISM: Artificial Sequence
<220> FEATURE:
<223> OTHER INFORMATION: Synthesized

<400> SEQUENCE: 66

```
gttggccact ccctctctgc gcgctcgctc gctcactgag gccgggcgac caaaggtcgc      60
ccgacgcccg ggctttgccc gggcggcctc agtgagcgag cgagcgcgca gagagggagt     120
ggccaactcc atcactaggg gttcctacgc gtccagcagc tcctgctttc tgagggtgaa    180
ggatagacgc tgtggctctg catgactcac tagcactcta tcacggccat attctggcag    240
ggtcagtggc tccaactaac atttgtttgg tactttacag tttattaaat agatgtttat    300
atggagaagc tctcatttct ttctcagaag agcctggcta ggaaggtgga tgaggcacca    360
tattcatttt gcaggtgaaa ttcctgagat gtaaggagct gctgtgactt gctcaaggcc    420
ttatatcaag taaacggtag cgctgggggct tagacgcagg tgttctgatt tatagttcaa    480
aacctctatc aatgagagag caatctcctg gtaatgtgat agatttccca acttaatgcc    540
aacataccat aaacctccca ttctgctaat gcccagccta agttggggag accactccag    600
attccaagat gtacagtttg cttttgccttg tcgagacaga gaagactctt gcgtttctga    660
taggcaccta ttggtcttac tgacatccac tttgccttc tctccacagg cggcggtggc    720
gagggcagag gaagtcttct aacatgcggt gacgtgagg agaatcccgg ccccatggcg    780
ctcccagtga cagccttact tttacctctg gcgttattat tgcacgcggc tcgtcctgac    840
atacagatga ctcagactac ctcttcccta tctgcttctt taggcgaccg agtaacaata    900
tcttgccggg ccagccagga catctcaaaa tacttaaact ggtatcagca gaagccggac    960
ggaacagtta agttgctcat ttaccacacg tcgagattac actcaggcgt tcctagccga    1020
```

-continued

```
ttttcgggtt ccggttccgg tacggactac agcctgacaa tcagtaacct tgagcaggag    1080
gacatcgcca cctacttctg tcagcagggc aacacgctcc cgtacacatt cggtggggga    1140
actaagctgg agattaccgg aggcggtggc agcggtggcg cggcagcgg gggtggcggc     1200
tcggaggtca agttacagga gagcggaccg ggcttggtcg cacctagcca gagcctctca    1260
gtcacgtgca ctgtgtctgg agtcagtctc ccagactacg gggtatcatg gatacgacag    1320
ccgcctagaa agggcttaga gtggctgggg gttatctggg gaagtgaaac cacatactac    1380
aactcagctc tcaagagccg cctcaccatc attaaggaca acagtaagtc gcaggttttc    1440
ttaaagatga actctctcca gactgacgac accgctattt actactgcgc gaagcactac    1500
tactacggcg ggagttacgc aatggactac tggggtcagg gcacttctgt gaccgtatcc    1560
agcactacta ccccagcccc acgtcccccc acgccagctc caacgatagc aagtcagccc    1620
ttatctcttc gccctgaggc ttgcaggccc gcggcgggcg cgccgttca cacgcgagga     1680
ctagacttcg cctgcgacat ctacatctgg gcaccactag ccgggacttg cggagtgttg    1740
ttgttgagct tggtaataac gctctactgc aaagcgagcc gcaaaaaagc ggcggcggcg    1800
gcgaaaagcc cgtttgcgag cccggcgagc agcgcgcagg aagaagatgc gagcagctgc    1860
cgcgcgccga gcgaagaaga aggcagctgc gaactgagag tgaagttctc tcgctccgcg    1920
gacgcacccg cttaccagca gggtcagaac cagctataca acgagttaaa cctggggcgc    1980
cgggaggagt acgacgtgtt agacaagcgt agaggtaggg acccggagat gggaggcaag    2040
cctcggagaa agaacccca ggagggcctg tacaacgaac tccagaagga caagatggct     2100
gaggcgtact cggagattgg tatgaagggc gagagacgtc gcggaaaggg acacgacggc    2160
ttataccagg ggcttccac cgcgaccaag gacacatacg acgcgctgca catgcaagcc     2220
ttaccacctc gatgaggtac cagcggccgc gatccagaca tgataagata cattgatgag    2280
tttggacaaa ccacaactag aatgcagtga aaaaaatgct ttatttgtga aatttgtgat    2340
gctattgctt tatttgtaac cattataagc tgcaataaac aagttaacaa caacaattgc    2400
attcatttta tgtttcaggt tcaggggggag gtgtgggagg ttttttaaag caagtaattg    2460
ctgggccttt ttcccatgcc tgcctttact ctgccagagt tatattgctg gggttttgaa    2520
gaagatccta ttaaataaaa gaataagcag tattattaag tagccctgca tttcaggttt    2580
ccttgagtgg caggccaggc ctggccgtga acgttcactg aaatcatggc ctcttggcca    2640
agattgatag cttgtgcctg tccctgagtc ccagtccatc acgagcagct ggtttctaag    2700
atgctatttc ccgtataaag catgagaccg tgacttgcca gccccacaga gccccgccct    2760
tgtccatcac tggcatctgg actccagcct gggttggggc aaagagggaa atgagatcat    2820
gtcctaaccc tgatcctctt gtcccacaga tatccagaac cctgaccctg ccgtgtacca    2880
gctgagagac tctaaatcca gtgacaagtc tgtctgccta ttcaccgatt tgattctca    2940
aacaaatgtg tcacaaagta aggattctga tgtgtatatc acagacaaaa ctgtgctaga    3000
catgaggtct atggacttca agagcaacag tgctgtggcc tggagcaaca atctgactt     3060
tgcatgtgca aacgccttca acaacagcat tattccagaa gacaccttct tccccagccc    3120
aggtaagggg aattgatgga gttggccact ccctctctgc gcgctcgctc gctcactgag    3180
gccgcccggg caaagcccgg gcgtcgggcg acctttggtc gcccggcctc agtgagcgag    3240
cgagcgcgca gagagggagt gg                                             3262
```